United States Patent [19]

Bouton et al.

[11] 4,045,772
[45] Aug. 30, 1977

[54] AUTOMATIC FOCUSING SYSTEM

[75] Inventors: John C. Bouton, Doylestown; Melvin E. Partin, Newtown Square, both of Pa.; Robert C. Hilghman, Willingboro, N.J.

[73] Assignee: Geometric Data Corporation, Wayne, Pa.

[21] Appl. No.: 679,259

[22] Filed: Apr. 22, 1976

Related U.S. Application Data

[62] Division of Ser. No. 465,390, April 29, 1974, Pat. No. 4,012,634.

[51] Int. Cl.² .............................................. G06K 9/08
[52] U.S. Cl. ..................... 340/146.3 B; 340/146.3 F; 235/92 PC; 356/39
[58] Field of Search .......................... 235/92 PC, 151.3; 340/146.3 D, 146.3 B, 146.3 F, 146.3 AH; 356/39, 71

[56] References Cited

U.S. PATENT DOCUMENTS

| | | | |
|---|---|---|---|
| 3,315,229 | 4/1967 | Smithline | 235/92 PC |
| 3,819,913 | 6/1974 | Carter et al. | 235/92 PC |
| 3,824,393 | 7/1974 | Brain | 356/39 |
| 3,827,804 | 8/1974 | Miller et al. | 356/39 |
| 3,873,974 | 3/1975 | Bouton et al. | 340/146.3 B |

Primary Examiner—Joseph M. Thesz
Attorney, Agent, or Firm—Caesar, Rivise, Bernstein & Cohen, Ltd.

[57] ABSTRACT

A white blood cell classification system is provided for detecting and classifying white blood cells in a peripheral blood smear. The system includes optical scanning means for scanning the blood smear, a microscope for directing the optical scanning means on the blood smear and means responsive to the scanning means for generating a signal corresponding to the color of the blood smear at the positions scanned. Color processing means are provided which are responsive to the signal for providing a signal representative of the relative darkness of the areas scanned. Detection means are provided which are responsive to the signal. The detection means includes a mask which is normally enabled by the nucleus of of all the white cells but which is not enabled by either platelets, foreign material or red cells in the blood smear. Finally, focusing means responsive to the detection means are provided for moving the position of the focus of the microscope to the optimum position after each white cell is detected.

11 Claims, 31 Drawing Figures

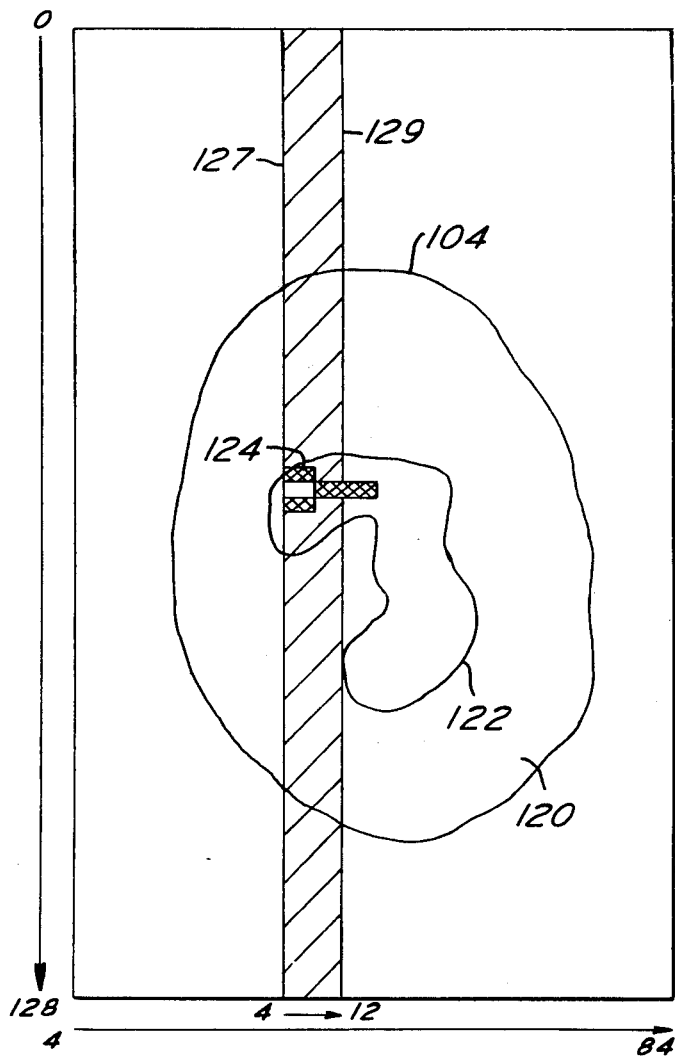
FIG. 4
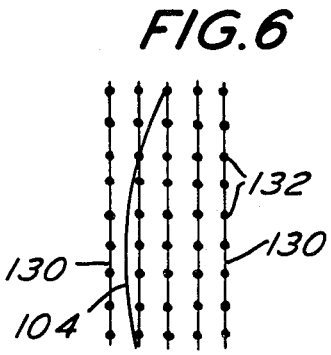
FIG. 6
FIG. 8
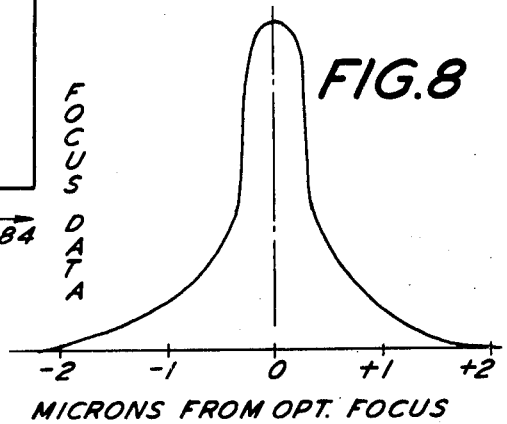
MICRONS FROM OPT. FOCUS
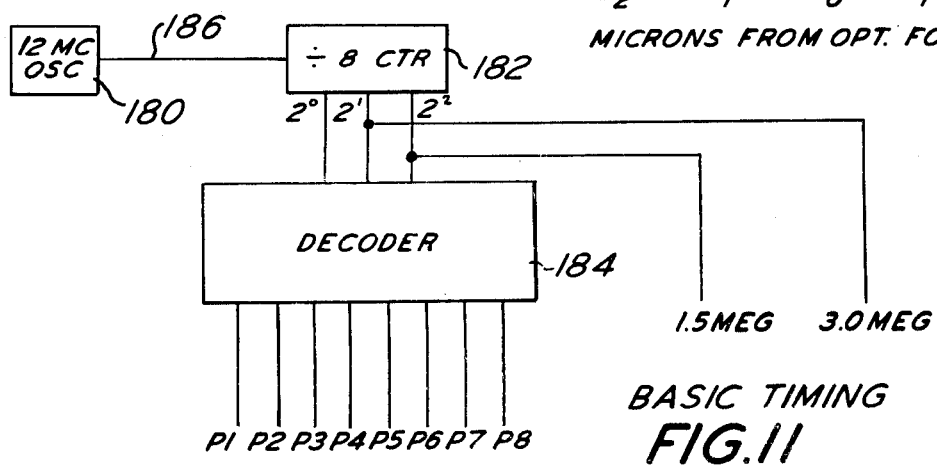
BASIC TIMING
FIG. 11

FAST SCAN TIMING

MODE CONTROL

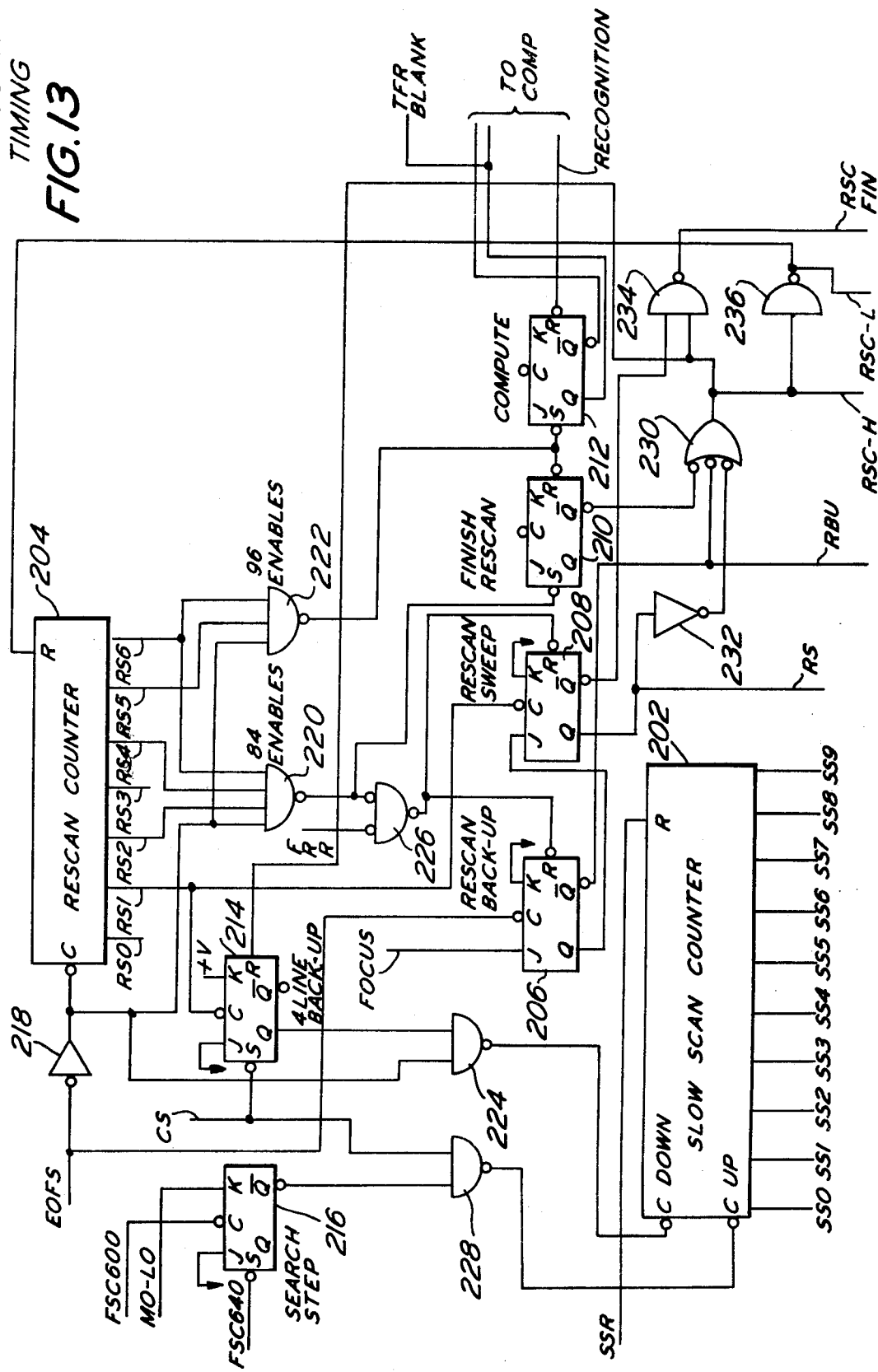
FIG.13 SLOW SCAN TIMING

COLOR PROCESSOR

FAST SCAN CONTROL

PATTERN CAPTURE

WINDOW CONTROL

SLOW SCAN CONTROL

RECYCLE AND BLANKING CONTROL

FIG. 21 AUTOMATIC FOCUS

FIG. 23 DATA COUNTER, COMPARATOR & MEMORY

DECISION LOGIC FIG. 24

POSITION CONTROL

AUTOMATIC FOCUSING SYSTEM

This application is a division of application Ser. No. 465,390, filed on Apr. 29, 1974, now U.S. Pat. No. 4,012,634.

TABLE OF CONTENTS

TITLE
Abstract of the Disclosure
Specification
Background of Invention
The Invention
Figures of the Drawing
Pattern Recognition System with Automatic Focus
Main Shift Register
System Timing
Fast Scan Timing
Slow Scan Timing
Mode Control
Color Processor and Quantizer
Pattern Capture
Window Control
Fast Scan Control
Slow Scan Control
Recycle and Blanking Control
Automatic Focus
Focus Data Counter, Comparator and Memory
Focus Decision Logic
Focus Position Control
Focus Control of Microscope Focus
Operation of the Fine Focus Assembly This invention relates generally to optical scanning instruments and more particularly to an automatic focusing system for a microscopic instrument.

BACKGROUND OF INVENTION

In optical pattern and character recognition systems where microscopic lens systems are required for directing a beam from a flying spot scanner at an extremely small object to be examined, it has been found that there exists the need for automatic focusing systems which enable the microscopic lens assembly to bring the object into optimum focus. For example, in optical pattern recognition systems which are utilized for the purpose of providing a differential white cell count of the blood of a patient, a sample of the whole blood is smeared and dried on a slide and a strain is used to enhance the contrast. In order to make an automatic differential white cell count of the blood, the slide is then used in combination with a microscopic lens assembly in an optical pattern recognition system.

After the slide has been placed in the microscopic instrument, it is then necessary to bring the slide into focus prior to starting the pattern recognition system. However, after the initial white cell is examined and the slide is moved so that the next white cell can be examined, quite often the next white cell is out of focus. It should be noted that when the human eye is used, the eye can tolerate a slightly out of focus microscope because of the fact that the eye can adjust. However, in an automatic system such as a character or pattern recognition system, the microscopic lens assembly must be in substantially exact focus because the circuitry responsive to the light focused through the lens system is not as adaptable as the human eye.

In view of the fact that substantially imperceptible flaws in a slide can require a change of focus of the optical instrument, it is necessary that the pattern recognition system utilized in a white blood cell differential count be constantly focused after each white cell is captured within the field of view of the microscopic lens assembly.

In the absence of an automatic focusing system, after the first cell has been analyzed by a pattern recognition system, each succeeding cell would have to be examined with the probability that the microscopic lens assembly had shifted out of focus. The disadvantage of course is that a cell not in optimum focus of the microscopic lens assembly is not as easy to recognize because of the fact that the transitions between the nucleus and cytoplasm of a white cell and the cytoplasm and the clear portions of the smear of the cell become more gradual as the distance from optimum focus increases. Thus, the recognition of the nucleus portion and the cytoplasm of the white cells is greatly diminished as a result of the blurred images caused by an optical instrument out of focus.

THE INVENTION

It is therefore an object of this invention to overcome the problems experienced in the prior art.

Another object of the invention is to provide an automatic focusing system for use in a microscope.

Another object of the invention is to provide a new and improved automatic focusing system which utilizes movement of the objective lens assembly to change the focus of the microscopic lens system.

Another object of the invention is to provide a new and improved automatic focusing system which utilizes a flying spot scanner in combination with light responsive means for generating a signal for enabling the microscopic instrument to obtain optimum focus.

Another object of the invention is to provide a new and improved automatic focusing system for a microscopic instrument for use in pattern and character recognition systems.

Yet another object of the invention is to provide a new and improved automatic focusing system which utilizes binary quantization at a plurality of levels and accumulation of a weighted count based on the quantization levels present in the field scanned in order to determine optimum focus.

These and other objects of the invention are achieved by providing a new and improved automatic focusing system for a microscopic instrument having a lens assembly and a platform for supporting an object. The system includes a flying spot scanner, the light from which is directed through the lens assembly at the object. Means are provided which are responsive to the light directed at the object for generating a signal representative of the color density of the object. Means are also provided which are responsive to the signal and connected to the instrument for focus of the instrument. The means responsive to the signal act to change the focus of the instrument a plurality of times and include decision means responsive to the signal for determining the optimum focus and move the instrument to the optimum focus.

In the preferred embodiment, the means responsive to the signal for changing the focus of the instrument is initiated upon the capture within the field of view of the microscopic lens assembly of a white blood cell. The objective lens assembly is then caused to be moved at least one micron from its former position so that a small portion of the object to be scanned can be scanned a plurality of times, each at a different position of the objective lens with respect to the optimum focus position. That is, the objective lens, after it has been moved one micron from its former optimum focus position, is moved one half micron during which time a first scan of a portion of the object is made. During this period, a weighted count of the quantization levels present in the signal is made and stored. The objective lens is then moved an additional half micron in the same direction at which time the quantization levels are again weighted and counted to determine whether a greater or lesser count is achieved. If a greater count is achieved during this second half micron movement, then the objective lens is moved again toward the optimum focus. During the third half micron of movement of the objective lens assembly, another weighted count is made of the quantization levels present in the signal and it is again compared to the previous highest count. If the count is again higher, the objective lens assembly is again moved in the same direction.

As soon as the weighted count during a one half micron movement is less that the highest previous weighted count, it means that the optimum focus point has been reached and passed, whereupon the objective lens is moved in the reverse direction until the optimum focus point is reached again. The position of the optimum focus is stored by the system so that it can be located when the movement of the lens assembly is reversed.

FIGURES OF THE DRAWINGS

These and other objects of the invention can be readily appreciated as the same become better understood by reference to the following detailed description when considered in connection with the accompanying drawings wherein:

FIG. 4 is an enlarged top plan view of a portion of the field in FIG. 2 including a neutrophillic band white cell;

FIG. 6 is an enlarged top plan view of a portion of the field shown in FIG. 5 with the path traversed by the beam superimposed thereon;

FIG. 8 is a graphic representation of the weighted quantization data count plotted against the distance of the focus from optimum focus;

FIG. 11 is a schematic block diagram of the basic timing unit, the signals of which are used throughout the system;

FIG. 13 is a schematic block diagram of the slow scan timing unit;

PATTERN RECOGNITION SYSTEM WITH AUTOMATIC FOCUS

Figure 1:
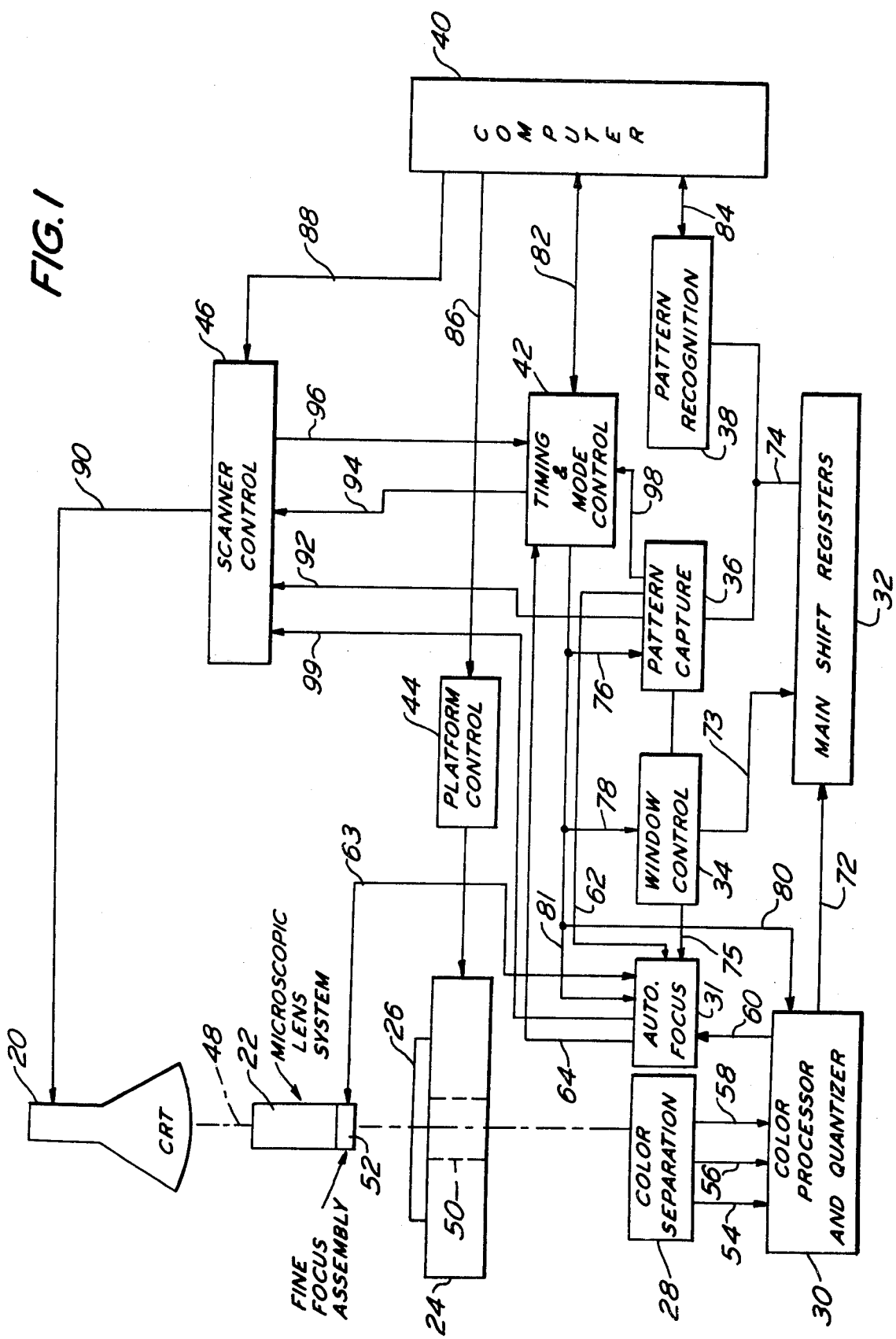
FIG. 1 is a schematic block diagram of a pattern recognition system embodying the invention.

Referring now in greater detail to the various figures of the drawings wherein like reference numerals refer to like parts, a pattern recognition system embodying the invention in automatic focusing is shown generally in FIG. 1. The preferred embodiment of the automatic focusing system has particular application in a pattern recognition system having a scanning system for location and classification of patterns which is the subject of U.S. Pat. No. 3,873,974 issued on Mar. 25, 1975 to the Assignee herein.

The pattern recognition system in FIG. 1 is adapted to provide a differential white cell count from a whole blood smear. The system includes a flying spot scanner optical system which includes a cathode ray tube 20, a microscopic lens system 22, a platform 24 for supporting a glass slide 26 having a whole blood smear thereon, a light component spearator 28, a color processor and quantizer 30, automatic focus circuits 31, a main shift register 32, a window control 34, a pattern capture 36, pattern recognition circuitry 38, a computer 40, timing and mode control 42, platform control 44 and scanner control 46. The cathode ray tube (CRT) 20 and the microscopic lens system 22 are preferably mounted within a housing which is light sealed so that a beam of light 48 can be directed through the microscopic lens system for focusing on slide 26. Similarly, the platform 24 and the light component separator 28 are also encased in a housing to prevent light, other than the beam of light 48, from entering the light component separator 28. The platform 24 includes an opening 50 through which the beam 48 is directed to the light component separator.

Microscopic lens system 22 includes a fine focus assembly 52 to facilitate the automatic focusing. The fine focus assembly 52 is the subject of U.S. Pat. No. 3,915,560 issued on Oct. 28, 1975 to the Assignee herein for Fine Focus Assembly. The disclosure in said application is incorporated by reference herein.

The beam of light 48 is produced by the cathode ray tube 20 which provides the beam in approximately a 3 × 3 inch scan raster on the face of the cathode ray tube which is directed and focused by the microscopic lens system down to a field of the size approximately 300 microns × 300 microns. Thus, a scan raster of light is directed at the slide 26 to traverse approximately a 300 × 300 micron field in the blood smear. The light passing through the slide 26 is directed to the light component separator 28 which filters the incoming beam and provides light through three spectral channels. The red, green and blue channels are chosen in accordance with the spectral absorbence of the component dyes in the Wright Stain which is conventionally used on a whole blood smear to facilitate visibility of the blood cells therein.

The light component separator 28 and the color processor and quantizer are the subjects of U.S. Pat. No. 3,827,804 issued on Aug. 6, 1974 to the Assignee herein for Color Separation for Discrimination in Pattern Recognition Systems. The disclosure in said last named application is incorporated by reference herein.

The light beam 48 which passes through the blood smear on glass slide 26 enters the light component separator 28. Dichroic mirrors are provided for splitting the light into blue, red and green components of the light spectrum. Photomultipliers are provided which are responsive to each of the light components. The three photomultipliers convert the three light components (blue, red and green) into electrical signals which are generated on lines 54, 56 and 58 which are connected to the color processor and quantizer 30. Each of the signals corresponds to the color density of the light spectrum which the particular photomultiplier is responsive. The color processor and quantizer 30 preprocesses the signals on lines 54, 56 and 58 and quantizes the signals for providing the signals in binary form to the main shift register 32, as well as to the automatic focusing circuitry 31.

The automatic focus circuitry 31 is responsive to the quantized signals received on lines 60 from the color processor and quantizer 30. The automatic focus system is initiated after a white cell has been captured within the field of view of the microscopic lens system. The signals indicating a capture are provided on lines 62 from pattern capture 36 to automatic focus 31. The automatic focus system is connected via line 63 to the fine focus assembly for automatically focusing the lens system prior to classification of each white cell. The automatic focus system also provides signals to the timing and mode control 42 via lines 64.

Window control unit 34 provides shift pulses on line 72 to the main shift register 32. The data received by main shift register 32 and automatic focus circuitry 31 from the color processor and quantizer 30 is determined by window control 34 which is connected to the main shift register via line 73 and automatic focus circuitry via line 75.

The pattern capture unit 36 and the pattern recognition unit are connected to the output of the main shift register via lines 74. The timing and mode control 42 is connected via lines 76, 78, 80 and 81 to the pattern capture unit, the window control unit, the color processor and quantizer 30 and the automatic focus 31, respectively. The mode control basically alternates the system between two modes of operation. The first mode is the search mode in which the scanner quickly traverses a field in the blood smear for determining where white cells are located. The second mode of operation is the rescan or classification mode wherein an area in which a white blood cell has been found is re-examined more closely so that the type of white blood cell that is being examined can be determined. It is during the rescan mode that the automatic focus is initiated immediately after a white cell is captured and prior to classification. The timing and mode control is also connected via lines 82 to the computer 40. Computer 40 is connected via lines 84 to the pattern recognition unit to the platform 44 via lines 86 and to the scanner control 46 via lines 88.

The scanner control 46 is connected via lines 90 to the CRT and is also connected to the output line 92 of the pattern capture unt 36. The platform control 44 is mechanically connected to the platform 24 and moves the platform 24 after a 300 micron × 300 micron field has been completely examined for white cells.

The platform control includes a stepping motor for moving the platform 24 in a predetermined pattern to assure that a separate and distinct field is viewed in each of the succeeding scans of the slide 26. The recycling of the beam 48 is controlled by the scanner control 46 which is connected to the timing and mode control 42 via lines 94 and 96. The pattern capture is connected via line 98 to the mode control 42. The mode control portion of the timing and mode control unit 42 causes the scanner control to operate the CRT in accordance with the mode that the system is operating. The automatic focus is connected to the scanner control by line 99.

Figure 2:
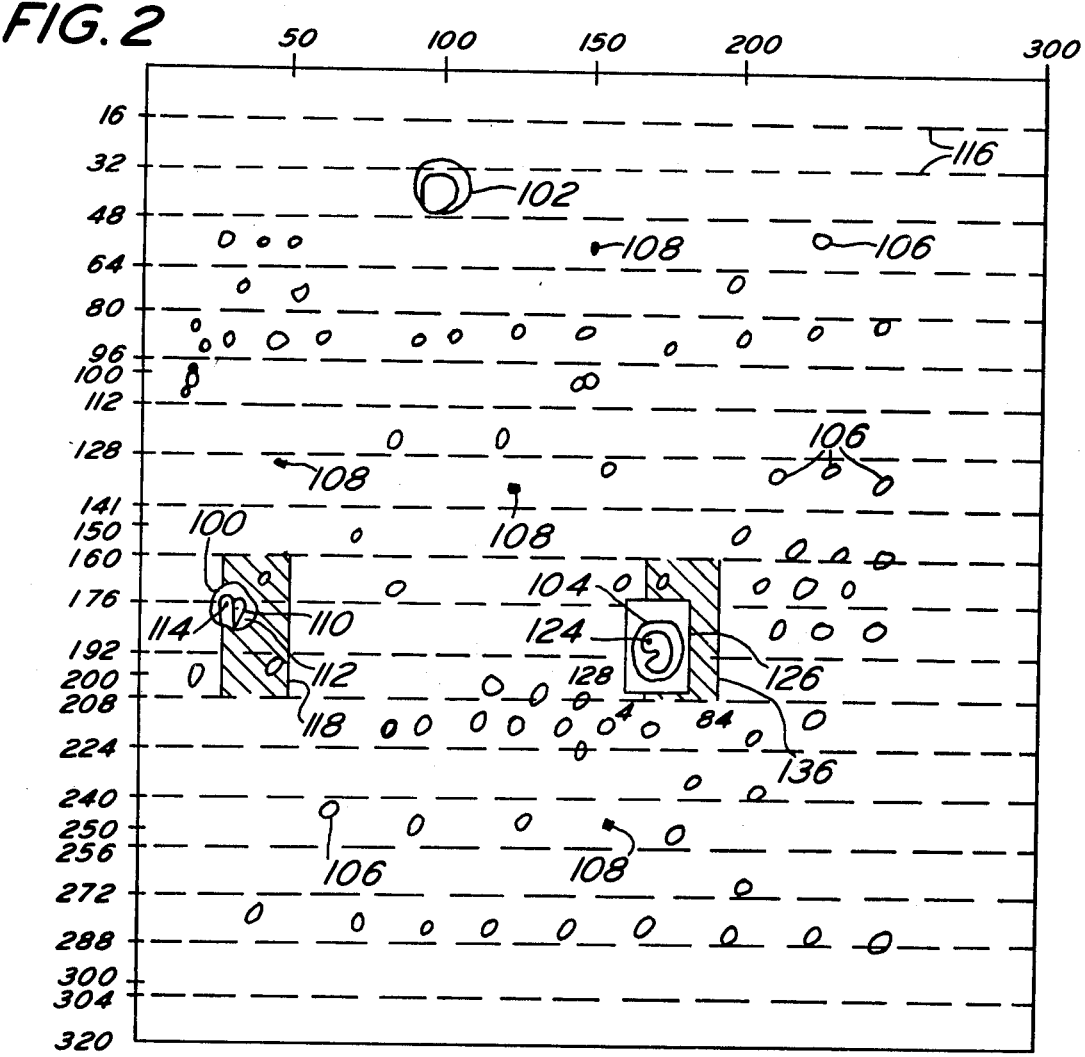
FIG. 2 is an enlarged top plan view of a rectangular portion of a field in a whole blood smear.

A 300 × 300 micron field of a whole blood smear is diagrammatically shown in FIG. 2. There are various classes of patterns within a blood smear. A first class of patterns in the blood smear are the white blood cells which include cells 100, 102, and 104. Cell 100 is an eosinophil white cell. Cell 102 is a lymphocyte white cell and cell 104 is a banded neutrophil white cell. A second class of patterns found throughout the blood smear around and adjacent the white cells are the red cells 106. In addition, there is a third class of patterns which are comprised of platelets 108 which are also scattered throughout the blood smear.

Among other things, the red cells can be differentiated from the white cells by the fact that not only are the red cells smaller, but the red cells are also different in color from the white cells. That is, the red cells appear red whereas the white cells, as a result of the absorption of the component dye in the Wright Stain appear bluish or a deep purple. The platelets 78 are also a deep purple or blue in color but are much smaller than the white blood cells.

During the search mode of the pattern recognition system shown in FIG. 1, the beam 48 starts in the field shown in FIG. 2 at the upper lefthand corner, proceeds to the bottom of the field and is then moved one micron to the right and starts at the top of the field one micron spaced from the leftmost edge of the field. Thus, the fast scan direction of the beam in FIG. 2 is from top to bottom and the slow scan direction is from left to right. As will hereinafter be seen, the beam actually traverses approximately 300 microns in the fast scan direction.

In the search mode, the beam progresses from left to right in the slow scan direction at a rate of one micron per fast scan sweep. Accordingly, the first white cell which is reached by the scanner is white cell 100. The white cell 100 includes a nucleus 110. The nucleus is surrounded by a cytoplasm 112. It should be noted that there is a dark point 114 in the nucleus 110 of the white cell 100 which indicates the point at which a pattern mask in the pattern capture 36 is enabled because a nucleus of a white cell has been scanned by the scanner. The pattern mask is diagrammatically shown in FIG. 3. The pattern mask in FIG. 3 actually represents an AND gate which is connected to the output line of the main shift register stages which correspond to the point in the field shown at 114 in FIG. 2. When this mask is enabled, the pattern capture 36 enables the timing and mode control, via line 98, to cause a rescan of the area including the white cell 114.

The timing and mode control provides a signal to the scanner control which causes the slow scan control signal to first move the beam back to the leading edge at which the detection of the capture was made for the purpose of determining optimum focus. After the best focus is found, the beam is moved back to a point approximately seven microns from the leading edge of the point at which the detection or the capture of the white cell was made.

During focusing and classification, the fast scan sweep continues to extend from the top of the field to the bottom of the field and the scanner progresses from left to right at the slower rate of a quarter micron per fast scan line or at a speed of ¼ the slow scan speed in the search mode.

It should be noted that superimposed over the field in FIG. 2 is a plurality of discontinuous lines 116 which extend from left to right and which divide the field into twenty areas from top to bottom. That is, the fast scan direction is broken up into twenty distinct areas. After the beam has progressed twenty microns in the rescan, the pattern recognition circuitry 38 has completed classification of the white cell which has been scanned and provides the signal to computer 40. The computer 40 then provides a completion of recognition signal on line 82 to the timing and mode control 42 which initiates the scanner control 46 to cause the scanner to start another search mode beginning at the point 114 at which a white cell was detected. Thus, a fast scan line starting at the top of the field in FIG. 2 starts at the slow scan position in which point 114 is detected.

To prevent capturing of the cell 100 again, the pattern capture circuitry 36 inhibits the pattern mask from detecting a white cell in the area in which the white cell 100 was captured. Thus, since the white cell 100 was captured with the capture point being in the area between 176 and 192 microns in the fast scan direction the pattern mask is inhibited for 24 microns of movement in the slow scan direction from detecting any white cell in the area between 176 and 192 microns in the fast scan direction. In addition, the pattern mask is also inhibited in the adjacent areas on each side of the area in which the pattern was detected so that between the points 160 and 208 microns in the fast scan direction the pattern mask is inhibited. This is shown by the shaded rectangle 118 which encompasses the white cell 100, Thus, if a white cell were disposed directly adjacent to cell 100 with its nucleus within the shaded rectangle 118 then the cell would not be counted during the cell classification.

Figure 3:
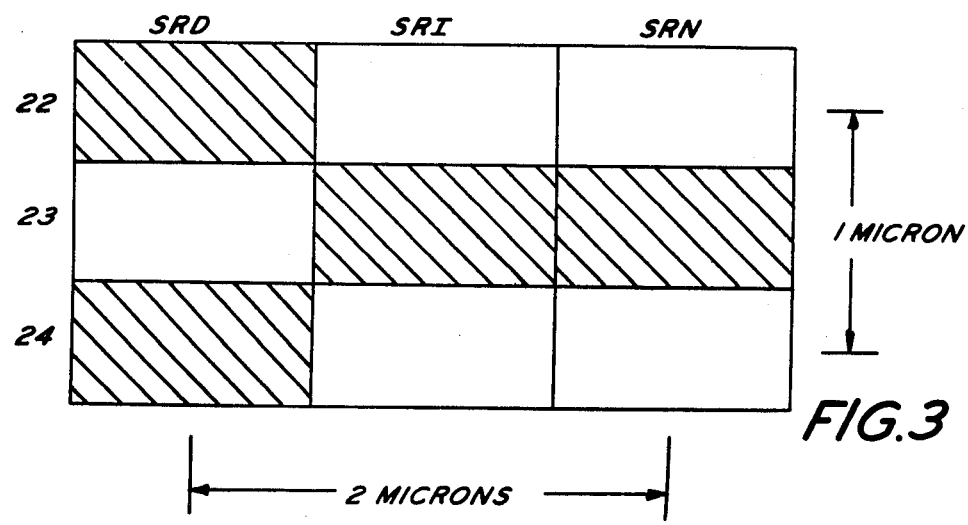
FIG. 3 is a diagrammatic representation of a pattern mask which is utilized in detecting the presence of a white blood cell in a whole blood smear.

As the search scan proceeds, the next cell in FIG. 2 that would be detected would be the lymphocyte white cell 102. The microscopic lens system is again focused and then the white cell 102 is classified. After the lymphocyted white cell is classified and the search scan proceeds, the next cell that is detected by the pattern mask in the capture circuitry 36 is white cell 104. White cell 104 includes a cytoplasm 120 and a nucleus 122. As the quantized data from the color processor and quantizer 30 which is the binary representation of the signals from the photomultiplier tubes is shifted in said register past the pattern capture 36, the pattern shown in FIG. 3 is superimposed over the binary quantization in the mains shift register. The pattern shown in FIG. 3 is being superimposed over the top lefthand corner of the nucleus 122 of the white cell 104 which is the first portion of the nucleus which passes underneath the capture pattern. As seen in FIG. 3, the mask or capture pattern is two microns by one micron wide. It is also in a generally Y-shape. This pattern is large enough and of a specific shape which avoids the capture mask from being enabled by platelets, but which fits into the nucleus of substantially all well formed white cells and thus enables capture of white cells while excluding platelets.

The color processor and quantizer provide signals on lines 72 to the main shift registers which effectively filters out all red cells information provided on slide 26 and the quantizing level is set high enough so that the cytoplasm information is also rejected so that only the nucleus of the white cell is examined by the pattern capture mask.

The numbers 22, 23 and 24 on the left side of FIG. 3 indicate the bit positions respectively of the shift register aperture which is examined as the binary quantization is shifted through the main shift registers 32. The legends SRD, SRI and SRN indicate the specific shift registers of the aperture in which the capture gate is connected.

Referring to FIG. 4, which is an enlarged diagrammatic plan view of the area of the field containing white cell 104, the pattern 124 is superimposed over the nucleus 122 to indicate the point at which capture is made of the white cell 104. Surrounding the white cell 104 is a border line 126 which diagrammatically represents the frame or window of the field in FIG. 2 which is examined during the rescan mode.

Two vertical lines 127 and 129 are also provided within the window 126. The area between lines 127 and 129 represents the area within the window which is examined during the focus cycle of the rescan mode. It should be noted that line 127 is on the leading edge of the pattern 124 and line 129 is spaced approximately eight fast scan lines or two microns therefrom.

That is, when the mask in the pattern capture 36 senses the nucleus 122 of white cell 104, a signal is applied via line 92 to the scanner control 46 which causes a beam to move backward in a slow scan direction so that it moves first to a point at the leading edge of the pattern at which capture is made in the nucleus 122 of cell 104. A plurality of focus scans is then initiated which travel between lines 127 and 129. After the best focus of the system is achieved, a signal is provided from the automatic focus circuitry to the scanner control circuitry 46 to enable the signals applied via line 192 to the scanner control 46 to cause the beam to move backward in the slow scan direction again so that the beam moves to a point seven microns to the left of capture point 124 at which capture was made in the nucleus 122 of cell 104.

The seven microns backup corresponds to the leftmost border of rectangle 126 which encircles the white cell 104. In addition, the point of capture 124 is placed approximately half way between the upper and lowermost edges of the rectangle 126 which represent the points in the fast scan between which the data fed to the main shift register is accepted for classification by the pattern recognition circuitry 38. This will be explained in greater detail with respect to the window control.

Figure 5:
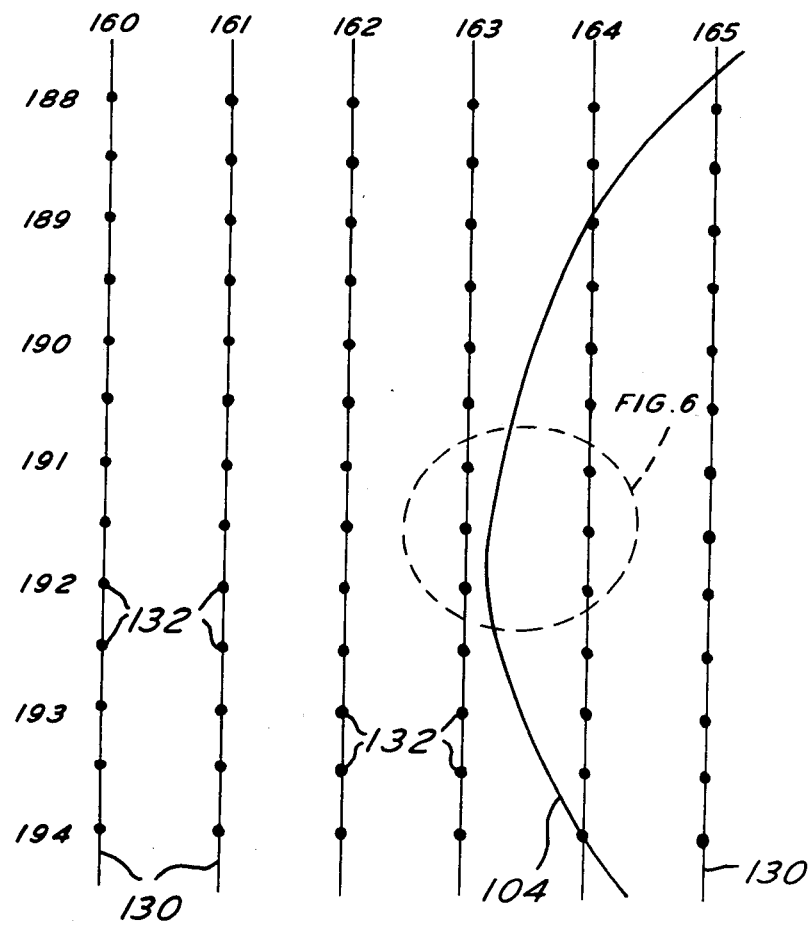
FIG. 5 is an enlarged top plan view of a small area of the whole blood smear shown in FIG. 2 with the path traversed by the scanning beam superimposed thereover.

For the purposes of illustration, however, FIG. 5 is a diagrammatic representation of the field adajcent to cell 104 between the areas 188 to 194 microns in the fast scan direction and 160 to 165 microns in the slow scan direction. The vertical lines 130 indicate the position over which the beam passes the field in a search scan mode. The points 132 represent the sampling points along the fast scan lines. As can be seen in FIG. 5, the samples are taken one half micron apart in the fast scan direction. In the slow scan direction there is only one line per micron in the search scan mode. Thus, the scan raster moves one micron in the slow direction after each fast scan.

FIG. 6 shows the portion of the field in FIG. 5 within the dotted lines labeled FIG. 6 and shows the field when the beam is in the rescan mode which includes both the focus cycle and classification cycle. Lines 130 are now a quarter of a micron apart in the slow scan direction and the samples 132 are taken one quarter micron apart in the fast scan direction.

Referring back to FIG. 4 the legend 0 to 128 from top to bottom on the lefthand side of said FIG. 4 indicates that the rectangle 126 represents 128 samples which are taken of the field within the window in the fast scan direction durig the rescan mode.

Below the bottom line of the rectangle 126 two sets of numbers, each having an arrow between them, are provided. The arrow between legends 4 and 12 indicates that eight lines in the fast scan direction pass over the area between lines 127 and 129 or that eight fast scan lines are sampled in the slow scan direction during each focus scan. The counts 4 to 12 represent the counts in a rescan counter which keeps track of the number of fast scan lines which are utilized in the slow scan direction during a focus cycle.

As will hereinafter be seen, the fast scan line, during the count of 12 in the rescan counter, is not used. Thus the eight fast scan lines are actually represented by the counts 4 to 11 in the rescan counter and on the count of 12 the rescan counter is reset during the focus cycle.

The arrow between 4 and 84 indicates that 80 samples are taken in the slow scan direction during a classification cycle. The counts 4 to 84 represent the counts in the rescan counter which keeps track of the number of fast scan lines which are utilized in the slow scan direction during classification of a pattern.

A shaded rectangle 136 is provided about the cell 104 in FIG. 2 which is analogous to the shaded rectangle 118 provided around cell 100. This indicates that during the next search scan a white cell cannot be detected within the three areas from 160 to 280 microns in the fast scan direction over the next 24 microns traversed in the slow scan direction. Since there are only three cells shown in the field in FIG. 2, the beam would progress to the end of the field at the right side of FIG. 2 and then be recycled. During the recycle the computer provides on line 86 to the platform control a signal causing the platform control to move the platform to the next position so that the next field can be scanned in the blood smear on slide 26.

Figure 7:
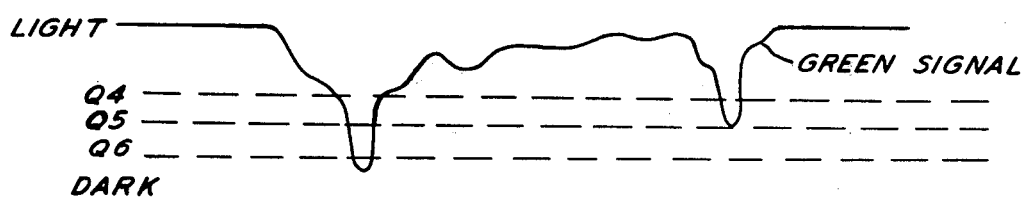
FIG. 7 is a graphic representation of a signal generated by the photomultiplier in the color separation unit in response to the green light spectrum of the light passing through the whole blood smear on slide 26.

FIG. 7 is a diagrammatic graphical representation of the green signal generated on line 58 from the color separation unit 28. As will hereinafter be seen, the green signal is used for analysis to determine optimum focus of the microscopic lens system. As the beam of light from the cathode ray tube traverses the field in the whole blood smear, the amount of light that passes through the slide 26 is dependant on the color density of the field at which the beam is located. Thus, in the portions of the blood smear between blood cells, the signal generated by the photomultiplier responsive to the green signal will be highest. At the leftmost side of FIG. 7 there are the legends LIGHT and DARK which are at the top and the bottom of the FIG. 7, respectively.

Thus, at the leftmost and rightmost portion of the green signal, the signal is lightest indicating that the beam is traversing a point in the field at which there is no blood cell present. As the beam traverses from left to right, the green signal goes down indicating that the beam is passing through a white cell. The legends on the left also include the legends Q4, Q5 and Q6, each of which is adjacent a dotted line, which extends at a different horizontal level in the figure.

Q4, Q5 and Q6 represent three different binary quantization threshold levels. The levels of Q4, Q5 and Q6 are so chosen that only the nucleus of a white cell or a platelet that is in substantially optimum focus exceeds the darkness level Q6 in the darkness direction. The Q5 level is chosen so that a nucleus of a white cell or platelet which is only slightly out of focus exceeds the Q5 darkness level. Similarly, Q4 is chosen at a next lighter level of darkness or color density which can be achieved by a nucleus of a white cell or a platelet which is out of focus by more than a micron, but not much more than 2 microns.

In addition to quantization levels Q6, Q5 and Q4, lighter quantization levels Q3, Q2 and Q1 are also used for purposes of focusing and pattern classification but are not shown herein for purposes of clarity. With the ligher quantization levels focus ranges are increased. That is, the amount of distance that the focus can be from the optimum position but which is correctable by the focusing system is increased.

Thus, the quantizer representative of Q6 is only enabled when the green signal on line 58 of the color separation unit is dark enough to dip below the level of Q6. The same is true of both quantizers Q5 and Q4 with respect to their levels, respectively. It should also be noted that any signal which exceeds the darkness of level Q6 also causes quantizers Q5 and Q4 to also generate a signal indicative of the fact that its quantization level has been exceeded.

FIG. 8 is a grahical representation of focus data plotted against microns from optimum focus of the fine focus assembly. The focus data is generated by the taking of weighted binary quantization counts at a plurality of distances from the optimum focus. That is, during the focus scan, three quantizers in the color processor and quantizer 30 which are respectively biased at the Q6, Q5 and Q4 levels are responsive to the green signal on line 58 from the color separation unit 28.

The focus data is generated by counting each Q6 level during a fast scan count as worth a count of six. Each time the green signal exceeds the Q5 level but not Q6, it is counted as a value of three. Each time the signal exceeds the Q4 level, but not the Q5 level, it is counted as a value of one.

An accumulator is provided in the automatic focus circuitry 31 which makes a weighted count at each sampling position 132 within window 126 between lines 127 and 129 in FIG. 4. Thus, an accumulation of this weighted quantization data at each of the positions indicated in FIG. 8 from optimum focus causes a focus data response chart which shows the data count to be highest at zero microns from optimum focus or at optimum focus. As the distance from the optimum focus increases upwardly or downwardly by the lens system, the focus data quickly drops off as a result of very few threshold levels exceeding the Q6 level and then exceeding the Q5 level. At approximately 2 microns from optimum focus in either direction the focus data drops off substantially.

Utilizing this knowledge, it will hereinafter be seen that the fine focus assembly has the objective lens therein moved to a plurality of positions at which a focus scan is made for accumulating a weighted quantization data count.

Assuming that the lens assembly moved from minus 2 microns to plus 2 microns, it can be seen that the focus data increases as the lens assembly approaches the optimum focus. As the lens assembly moves past optimum focus, the focus data starts to decrease.

In summary, the system of FIG. 1 operates as follows. The scanner control 46 causes the beam 48 in the cathode ray tube 20 to be focused on the blood smear on slide 26 to move approximately 300 microns in a fast scan direction taking samples at one half micron intervals. The beam is moved one micron in the slow scan direction for each fast scan line until the mask in the pattern capture 36 is enabled. The pattern capture 36 provides a signal to the timing and mode control 42 which changes the mode to a rescan and also provides a signal to the window control based on the point at which the capture mask was enabled. The timing and mode control 42 causes the scanner control to move the beam backwards to the point at which capture was made.

At the same time, the automatic focus 31 is initiated by the pattern capture via line 62. The automatic focus circuit 31 then provides a signal to the microscopic lens systems fine focus assembly 52 which causes the lens to be moved 1 micron from the optimum focus position during the previous classification. After the objective lens assembly in fine focus assembly 52 has been moved one micron from the previous optimum focus, the direction of movement of the lens then proceeds in the reverse direction towards the previous optimum focus. During the movement in the first half micron, a first focus scan is made over eight lines in the window in which the white cell has been captured. This data count is stored and a second data count is made during the interval of movement during the second half micron. This is compared against the data count made during the first half micron to determine whether the data count is increasing.

A third focus scan is made during the third half micron interval and the data count generated during the interval is compared against the previous high data count. As long as the data count increases during the half micron intervals, it means that optimum focus is still being approached. As soon as the data count taken in a half micron interval is less than the previously high stored data count, this indicates that the optimum focus point has been passed. If a predetermined number of half micron intervals of movement of the lens is achieved, prior to the passing of the optimum focus point, the direction of movement of the lens assembly in the fine focus assembly 52 is reversed and returned to the optimum focus point. If the predetermined number (3) of intervals of increasing counts is not reached, the movement is reversed after four consecutive decreased counts and data counting during half micron movements are made in the reverse direction. The direction of movement is reversed again and moved to the optimum focus point.

At the time that the optimum focus point has been reached, the automatic focus circuitry provides a signal on line 99 to the scan control 46 which causes the scanner control to move the beam backwards approximately seven microns to the left of the point at which capture was made.

The sampling of the fast scan continues at a one quarter micron interval during the classification cycle in a portion of the field determined by the point at which capture was made. Thus, as seen in FIG. 4, the top of the rectangular frame 126 starts approximately 60 samples above the point at which capture of the pattern was made. The window control causes the 128 sampled bits from each fast scan line to be entered into the main shift register 32 during the 80 fast scan lines 4 through 84 of the rescan mode. When pattern recognition has been made by pattern recognition circuitry 38, signals are provided to the computer with the information gathered by the recognition system circuitry 38 and the computer provides a recognition signal on line 88 to the scanner control 46 which causes the search mode to be reinstituted thereby causing a fast scan to start at the line in the slow scan direction at which the point of capture was made.

The pattern capture circuitry 36 includes inhibiting means which then prevent recapturing of the white cell within the three discrete areas of the fast scan direction in which the white cell was captured during the next 24 fast scan lines of the search mode.

A preferred pattern recognition system for use in, classification of the white cells is shown in U.S. Pat. No. 3,832,687 issued on Aug. 27, 1974 to the Assignee herein.

MAIN SHIFT REGISTER

Figure 9:
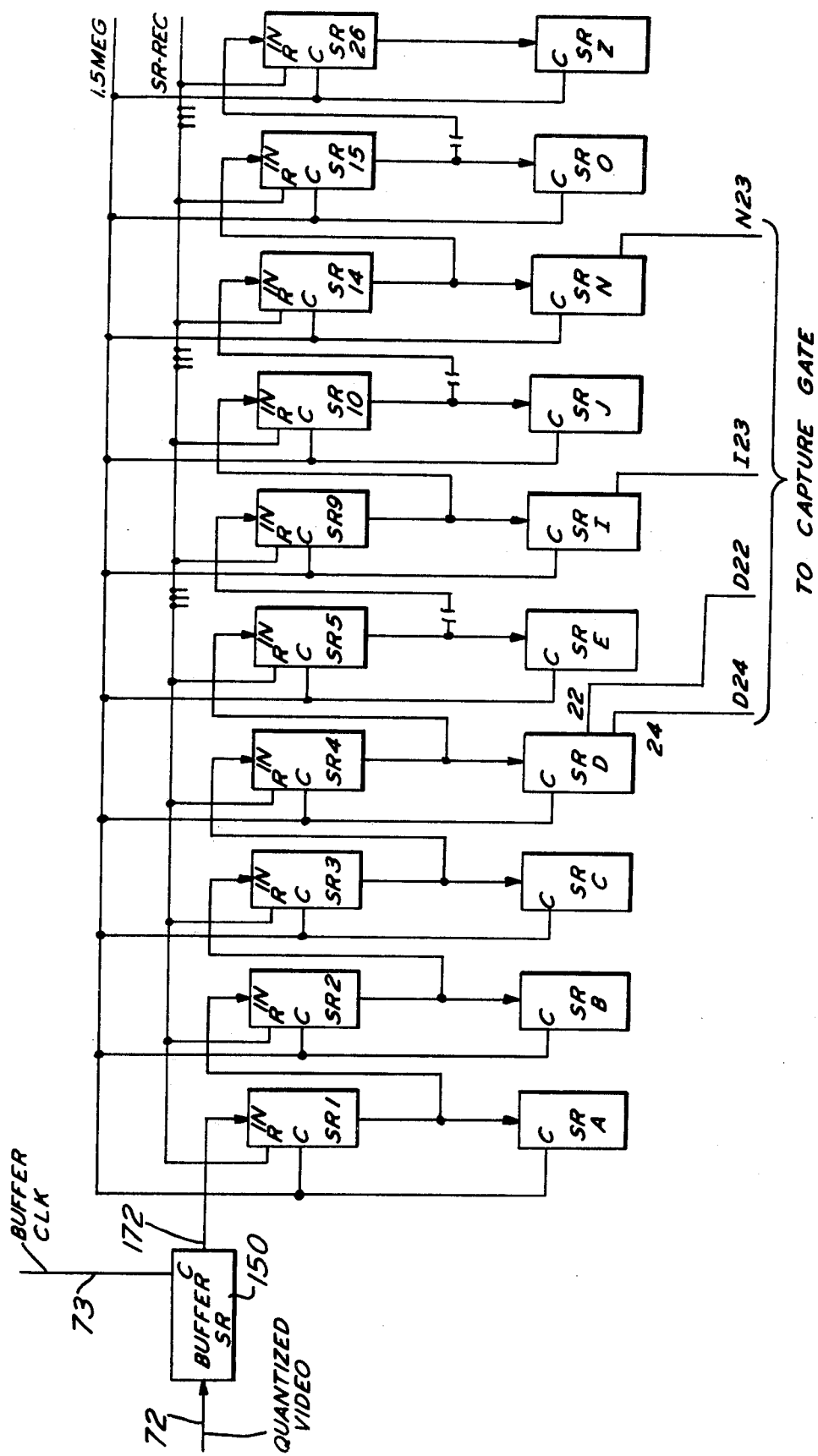
FIG. 9 is a schematic block diagram of a portion of the main shift register.

The main shift registers 32 are shown in FIG. 9. The main shift registers include a buffer shift register 150. 26 shift registers SR1 through SR26, and 26 shift registers SRA through SRZ. Shift registers SR1 through SR26 all include the circuitry shown in FIG. 10.

Figure 10:
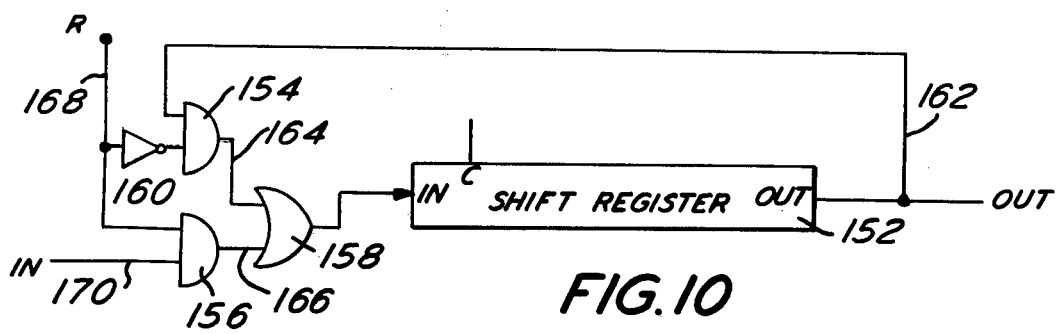
FIG. 10 is a schematic block diagram of a shift register circuit utilized in the main shift register.

As seen in FIG. 10, the shift registers SR1 through SR26 each include a 128 bit shift register 152 and control gating which comprises a pair of AND gates 154 and 156, an OR gate 158 and an inverter 160. Shift register 152 has an output line which is connected via line 162 to a first input of AND gate 154. In addition, the shift register 152 also has an input line which is connected to the output of OR gate 158. One input of OR gate 158 is connected to the output of AND gate 154 via line 164 and the other input line 166 of OR gate 158 is connected to the output of AND gate 156. Line 168 which is the R input line of the circuit is connected to one input of AND gate 156 and the second input of AND gate 154 via the inverter 160. Line 170 is the IN line of the circuit and is connected to the second input of AND gate 156.

When the input signal to line 168, the R input line of the circuit, is low, the information in the 128 bit shift register 152 recirculates via line 162 through AND gate 154 and OR gate 158 to the input line of the shift register 152. When the signal on line 168 is high, the AND gate 154 is disabled. However, AND gate 156 becomes enabled to pass signals on line 170 to the input of the shift register 152.

The C input line of the shift register 152 receives clock pulses and shifts the data from the input line to the output line one bit at a time for each pulse received on the clock input line.

Referring back to FIG. 7, it can be seen that 26 of the shift register circuits shown in FIG. 8 are utilized in the main shift register. For purposes of clarity the stages SR6 to SR8, SR11 to SR13 and SR16 through SR25 have not been shown in FIG. 7. The input to the buffer shift register 150 is line 72 from the color processor and quantizer and provides quantized video signals to the buffer shift register 150. The buffer shift register 150 receives shift pulses from the BUFFER-CLK line 73 which shifts data into the buffer shift register and effectively samples the quantized pattern at the rate of the shift pulses provided on line 73. The buffer shift register 150 is connected at its output line to the input of shift register SR1. The output line of shift register SR1 is connected via line 174 to the input of shift register SR2 and also via line 176 to the input of the 24 bit shift register SRA. Similarly, the output lines of the shift registers SR2 through SR26 are each connected to the input of shift registers SRB to SRZ, respectively.

The output lines of shift registers SR2 through SR25 are connected to the input lines of shift registers SR3 to SR26, respectively. As can be seen, the clock input of each of registers SR1 through SR26 and SRA to SRZ are connected to the 1.5 MEG line which receives shift pulses at a 1.5 megacycle rate. The R input to each of the shift registers SR1 through SR26 are connected to the SR-REC line. This signal on the SR-REC line controls whether the shift registers SR1 through SR26 recirculate and therefore reject data from the buffer shift register or receive data from the buffer shift register. When the SR-REC line is high, the information is accepted from the buffer shift register 150.

The buffer shift register 150 is also a 128 bit shift register. When the system is in a search mode, the SR-REC line is high all the time and the clock pulses on line 73 to the buffer shift register are constantly at a 1.5 megacycle rate. Thus, during the search scan all of the binary quantized video that is received by the buffer shift register 150 is passed into the shift registers SR1 through SR26 which is serially fed from the beginning of shift register SR1 to the end of shift register SR26. The shift registers SRA through SRZ represent an aperture in which data in the shift register comprised of shift registers SR1 through SR26 can be sampled. That is, the shift register SR1 through SR26 are preferably MOS shift registers which have taps only at the input and output thereof. The shift registers SRA through SRZ are 24 bit shift registers, but each of the 24 bits of the shift register can be sampled. Thus, for pattern classification, as well as pattern capture, even through the information comes in at one end of the shift registers and goes out the other end without being recirculated, nonetheless, all of the data that is fed through shift registers SR1 through SR26 ultimately passes through shift registers SRA to SRZ and can therefore be used for examining the entire pattern that goes therethrough.

It should be noted that the shift registers SRD, SRI and SRN each have output lines. The output lines for shift registers SRD which are labelled, respectively, D22 and D24 represent output bits 22 and 24 of shift register D. The output line I23 connected to shift register SRI represents the output of bit 23 of shift register SRI. Similarly, output line N23 of shift register SRN represents the output of bit 23 of shift register SRN. Lines D22, D24, I23 and N23 are connected to the capture gate of the pattern capture circuitry 36.

Referring to FIG. 3, it can therefore be seen that the pattern mask represents the output of bits 22 and 24 of shift register SRD, bit 23 of shift register SRI and bit 23 of shift register SRN which must each be in the one state in order to capture a white cell. It should be noted that the lines for the capture mask are tapped off of shift registers SRD, SRI and SRN which are respectively connected to shift registers SR4, SR9 and SR14 which are five shift registers apart. This is because each fast scan line represents 640 1.5 megacycle pulses. Accorindgly, it requires five 128 bit shift registers to store an entire line of samples in a fast scan direction.

During the rescan mode, the SR-REC line receives a low signal for all but 128 counts of the fast scan counter which controls the fast scan lines. The buffer shift register receives shift pulses from line 73 at a 1.5 megacycle rate during the time that the count in the fast scan counter goes from 640 to 767, but line 73 receives pulses at a 3.0 megacycle rate during the time that the window is open to pass data from the quantized video to the buffer shift register representative of the information in the area including the white cell which had been captured. After the 128 bits of each fast scan line from the window area have been placed in the buffer shift register 150 the signal on line SR-REC goes high and the 1.5 megacycle clock pulses start in the buffer shift register 150 to cause a readout of the information into the shift register SRI. During the next fast scan line the data shift register 150 is fed to SR1 and the data in SR1 is fed to SR2 and so on. In this way, only the information within the window 126 is fed into the shift registers SR1 through SR26. As the information is passed into the shift registers SR1 through SR26 during the classification scan, the information is passed off to shift registers SRA to SRZ and examined by the pattern recognition circuitry 38 which gives the information to the computer 40 for processing and as soon as a recognition of a white cell is completed, the computer provides a recognition signal which enables the scanner control to return to the search mode of operation.

It should be noted that during the focus scan, even though the information from the window is placed into the shift register stages SR1 through SR26, as in the classification scan, the quantized data is fed directly from the quantizers in the color processor and quantizer 30 to the automatic focus circuitry 31. The only data that is accepted by the automatic focus circuitry is still controlled by the window control 34 which enables the quantized data to be entered into the automatic focus circuitry only during the fast scan window.

It should also be noted that although the main shift registers have been shown as a serially progressing single bit wide shift register in FIG. 9, the main shift registers are actually plural bit stages. That is, the main shift register receives a plurality of levels of quantized data on lines 72 to the buffer shift register. Each of the stages of the buffer shift register 150 is capable of storing a plurality of bits dependent on the number of quantization levels and different color quantizations provided to the main shift register. Similarly, each of the shift registers SR1 through SR26 is also a plural bit shift register which is capable of storing simultaneously the plurality of bits in accordance with the number of quantization levels required by the pattern recognition circuitry.

SYSTEM TIMING

The basic system timing or the timing control of the circuitry is shown in FIG. 11. The basic timing circuitry includes a 12 megacycle oscillator 180, a divide by eight counter 182 and a decoder 184. The output of the 12 megacycle oscillator is connected via line 186 to divide by eight counter 182. The divide by eight counter 182 is a three stage binary counter having output lines which are labelled, respectively, $2^0$, $2^1$ and $2^2$. These output lines are connected to the decoder 184 which decodes the binary input on the lines from the divide by eight counter and provides signals on eight lines which are respectively labelled P1 through P8. The $2^1$ output line provides the clock pulses at a 3.0 megacycle rate on the 3.0 MEG line and the $2^2$ output line provides clock pulses at the rate of 1.5 megacycles which is provided on line 1.5 MEG. The lines P1 through P8 are each pulsed once for each 1.5 megacycle pulse. Thus, the decoder 184 breaks each 1.5 megacycle count into eight phases. The P1 through P8 signals are each of very short duration and are generated by the binary counts of 000 through 111 (0 through 7), respectively.

FAST SCAN TIMING

Figure 12:
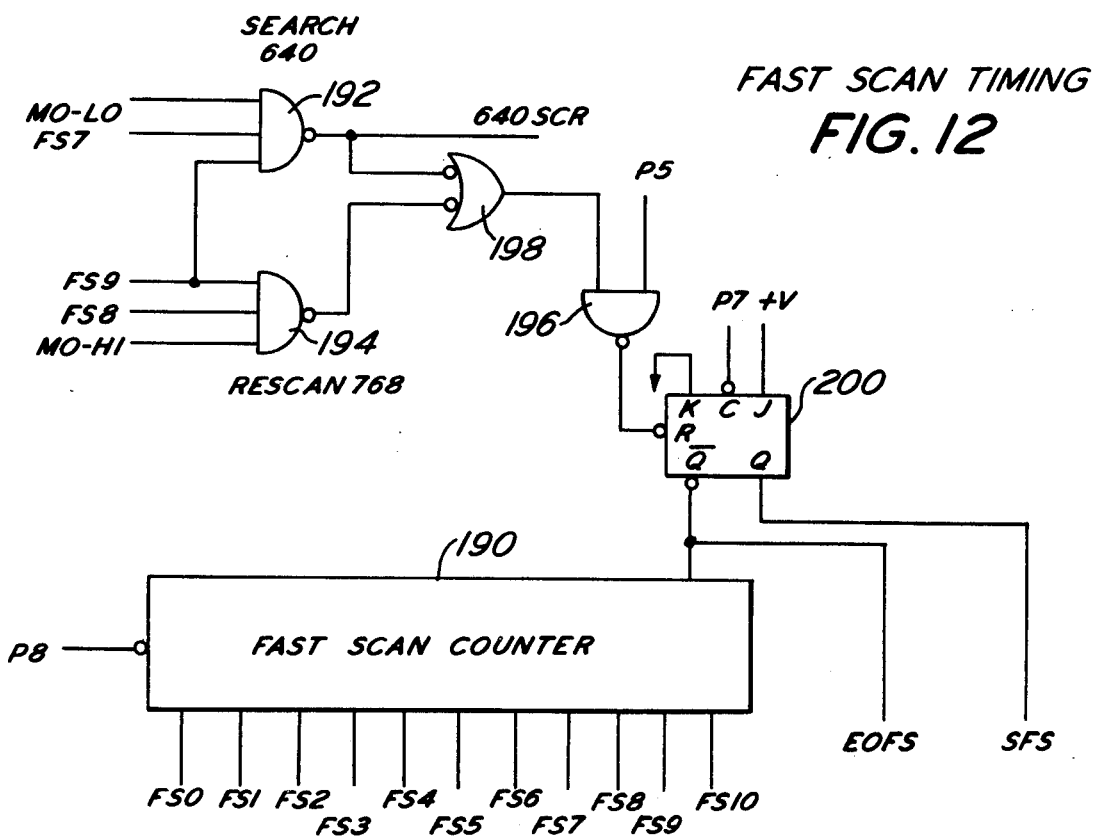
FIG. 12 is a schematic block diagram of the fast scan timing circuitry.

The fast scan timing is shown in FIG. 12. The fast scan timing circuitry includes the fast scan counter 190 and the control circuitry for recirculating the fast scan counter including AND gates 192, 194 and 196, OR gate 198 and flip flop 200. With respect to the logic circuitry shown throughout the drawings, it should be noted that the half circles represent AND gates and the crescent shaped gates represent OR gates. Where circles are used at the inputs of the AND gates or OR gates, it means that the ground signal is required to enable the gate. Where circles are used on the output lines of the gates, it means that when the gate is enabled, the output is ground. Similarly, where a circle is used as an input to a module such as a counter module it means that the module is clocked on the negative going pulse. With respect to the flip flops, conventional JK flip flops are used throughout for the flip flops.

The fast scan counter 190 is a conventional binary counter. The fast scan counter is stepped at a 1.5 megacycle rate by the signal at its clock input which is connected to output line P8 of the decoder. Thus, the P8 signals step the fast scan counter at a 1.5 megacycle rate. The fast scan counter includes eleven output lines which are labelled FS0 through FS10, respectively. The output lines are connected to each of the first 11 stages of the fast scan counter and correspond to the $2^0$ through $2^{10}$ output lines of the binary counter. Output line FS9 is connected to a first input of both AND gates 192 and 194. Output line FS8 of fast scan counter 190 is connected to the input of AND gate 194. The second input to AND gate 192 is the output line FS7 of the fast scan counter. The third input to AND gate 192 is the line MO-LO which is high during the search mode of operation. The third input to AND gate 194 is the MO-HI line. The signal on the MO-HI line is high during the rescan mode of the system. The output of the AND gate 192 is connected to a first input of OR gate 198 and is also connected to the 640 SCR line. The AND gate 194 is connected to the second input of OR gate 198. The output of OR gate 198 is connected to a first input of the AND gate 196 and the second input to gate 196 is connected to the P5 line. The output of AND gate 196 is connected to the reset line of flip flop 200. The K input of flip flop 200 is connected to ground and the J input of flip flop 200 is connected to +V. The clock input is connected to output line P7 of the timing decoder. The $\overline{Q}$ output line is connected to the reset of the fast scan counter 190 and also to an output line EOFS which indicates the end of the fast scan. The Q output line is connected to the SFS line.

In operation the fast scan counter is clocked by the phase 8 pulses P8 at a rate of 1.5 megacycles. When the fast scan counter is in a search mode the MO-LO signal is high thereby allowing gate 192 to be enabled when the count in the fast scan counter reaches 640. When AND gate 192 is enabled it causes the OR gate 198 to be enabled as the output of gate 192 is low and thereby allows the enabling of OR gate 198. When OR gate 198 is enabled the AND gate 196 is enabled by the first P5 pulse from the timing decoder. Thus, gate 196 is enabled for a shirt spike causing a low signal on its output line which resets the flip flop 200 which remains reset until the P7 pulse goes low and thereby sets the flip-flop as a result of the +V applied to the J input of flip flop 200. During the period that the flip flop 200 is reset it causes the $\overline{Q}$ output line to reset the fast scan counter after the fast scan counter reaches 640. During the rescan mode of operation the MO-HI signal is high thereby enabling gate 194 to be enabled when the fast scan counter reaches the count of 768. When AND gate 194 is enabled it causes the enabling of OR gate 198 which in turn causes AND gate 196 to be enabled on the next P5 high signal which therey causes the resetting of flip-flop 200 for a short period of time between P5 and P7 pulse. As soon as P7 goes low the flip flop 200 is set again and the fast scan counter which was reset is again stepped during each P8 pulse.

It should therefore be noted that the fast scan counter, during the search mode, counts from 0 to 640 and during the rescan mode (including both the focus cycle and the classification cycle) from 0 to 768.

SLOW SCAN TIMING

The slow scan timing circuitry is shown in FIG. 13. The slow scan timing includes slow scan counter 202, rescan counter 204, the rescan backup flip flop 206, a rescan sweep flip flop 208, a finish rescan flip flop 210, a compute flip flop 212, a four line backup flip flop 214 and the search step flip flop 216. The EOFS line from the fast scan timing is connected to the C input of the rescan counter 204 via an inverter 218. The rescan counter 204 is a binary counter having seven output lines which are labelled RS0 through RS6 and represent the $2^0$ through $2^6$ output lines of the respective stages of the binary counter. The output of inverter 218 is conncted to a first input of each of the pair of AND gates 220 and 222. The remaining input lines of AND gate 220 are connected respectively, to the output lines RS2, RS4, and RS6 of the rescan counter 204. The remaining inputs of AND gate 222 are connected to the output lines RS5 and RS6 of the rescan counter 204.

The rescan counter 204 keeps track of the number of fast scan lines that have been completed during a rescan mode. The output of inverter 218 is also connected to the first input of an AND gate 224. The second input to AND gate 224 is the Q output line of flip flop 214. The set input line of the four line backup flip flop 214 is connected to input line CS. The CS line goes low when the capture mask in the pattern capture circuitry has detected a white cell. The CS line is also connected to an input of AND gate 228. The J input of flip flop 214 is connected to ground, the K input is connected to +V and the reset input is connected to the RSC-H line which is the output line of OR gate 230.

The input line connected to the K input of the search step flip flop 216 is the MO-LO line. The clock input of the flip flop 216 is the FSC 600 line which goes low when the count in the fast scan counter goes to 600. The J input of flip flop 216 is connected to ground and the set input is connected to the FSC 640 line which goes low when the count in the fast scan is 640. The MO-LO line to the K input of flip flop 216 inhibits the flip flop 216 from being reset then set at the end of each fast scan line during the rescan mode. The $\overline{Q}$ output line of flip flop 216 is connected to the second input of AND gate 228. The output of AND gate 228 is connected to the C up input of the slow scan counter 202. The output of AND gate 224 is connected to the C down input of slow scan counter 202. The reset input of slow scan counter 202 is connected to the slow scan reset line SSR. The slow scan counter 202 is a binary counter and has ten output lines, each of which is connected to a different stage of the slow scan counter. The outputs lines which represent the outputs of the $2^0$ through $2^9$ stages are labelled, respectively, as SS0 through SS9.

The slow scan counter directly controls the location of the beam in the slow scan direction. The C input of the rescan backup flip flop 206 is connected to the EOFS line. The K input is connected to ground, the J input is connected to the FOCUS line from the output of the focus circuitry 31. This signal goes high as soon as CS goes low and the signal stays high until the end of the focus cycle. The Q output line of rescan backup flip flop 206 is connected to the J input of rescan sweep flip flop 208, the $\overline{Q}$ output of flip flop 206 is connected to the input of OR gate 230 and to output line RBU. The R input of flip flop 206 is connected to the output of AND gate 226. The rescan sweep flip flop 208 has its C input connected to the output of the $2^1$ stage of the rescan counter 204. The K input is connected to ground, the J input is connected to the Q output line of flip flop 206. The R input line of flip flop 208 is connected to the output of AND gate 226. The Q output line of flip flop 208 is connected via inverter 232 to the input of OR gate 230 and to the RS output line. The $\overline{Q}$ output line of flip flop 208 is connected to the input of AND gate 234. The inputs to AND gate 226 are the outputs from AND gate 220 and the FRR line which is connected to the automatic focus and has a low signal generated thereon at the end of each focus scan.

The finish rescan flip flop 210 has its set input connected to the output of AND gate 220, its reset input connected to the output of AND gate 222 and its $\overline{Q}$ output connected to the input of OR gate 230. The output of OR gate 230 is connected to the input of AND gate 234 and to output line RSC-H as well as to the reset input of flip flop 214. The compute flip flop 212 has its set input line connected to the output of AND gate 222 and its reset input line connected to the recognition line which goes to the computer. The Q output line goes to the computer as well as to the output line TFR-BLANK. The $\overline{Q}$ output line of flip flop 212 goes to the computer. The output of OR gate 230 also is connected via output line RSC-H to an inverter 236. The output of inverter 236 goes to output line RSC-L as well as to the reset input of the rescan counter 204. The output of AND gate 234 is connected to the RSC-FIN line.

The operation of the slow scan timing is as follows:

During the search mode of operation, the MO-LO line is high thereby causing the search step flip flop 216 to be reset when FSC 600 goes low on the counter of 600 in the fast scan counter. Flip flop 216 is set when the count of 640 is reached in the fast scan counter and thereby causes FSC 640 to go low at the set input. The $\overline{Q}$ output line of the flip flop 216 disables the AND gate 228 and thereby causes the slow scan counter to be stepped up one each time a fast scan line is completed. As soon as the capture mask in the pattern capture circuitry is enabled, the CS line goes low thereby causing the AND gate 228 to remain disabled during the period when the fast scan counter goes from 600 to 640 and thus not enabling the slow scan counter to count up. At the time the CS signal goes low, the focus line also goes high which causes the four line backup flip flop to be primed to be set by the next EOFS signal. As soon as there has been a white cell capture it causes AND gate 224 to be enabled to pass pulses to the C down input of the slow scan counter at the end of the fast scan count which generates the EOFS signal pulse which is passed to the C down input of Counter 202 by gate 224. When the rescan backup flip flop 206 is set on the EOFS signal going low, it causes the OR gate 230 to be enabled and thereby allows the reset signal to the rescan counter 204 to be released so that the rescan counter can count up during the rescan mode of operation. The four line backup flip flop 214 remains in the set position until the count in the rescan counter 204 changes from 3 to 4 thereby causing a negative going signal on the C input line which resets the flip flop 214 as a result of the K input being connected to +V.

Thus, four pulses are enabled to be passed by AND gate 224 to the slow scan counter. The lowering of the count by the number 4 in the slow scan counter effectively places the slow scan counter at the position where the start of the scanning of the captured pattern began. That is, because the main shift registers must receive three lines of data in order to recognize the capture pattern for a white cell and an additional scan line is completed, after the capture pulse is generated, the slow scan counter must be stepped down, 4 counts, in order to initiate a complete fast scan line when the search mode is restarted. With both gates 224 and 228 disabled when the count of 4 is reached in the rescan counter, the slow scan counter remains at the stepped down count for the remaining portion of the rescan mode of the pattern scanner.

When the rescan counter is stepped from a count of 3 to 4, the RS1 line goes low and causes the rescan sweep flip flop 208 to be set as a result of the priming of the J input thereof by the high signal on the Q output line of the rescan backup flip flop 206. The rescan backup flip flop 206 stays set from the end of the fast scan line immediately following the generation of the capture pulse until the rescan counter reaches the count of 12 during each of the plurality of focus scans and is set at the beginning of the classification cycle until the rescan counter reaches the count of 84. The $\overline{Q}$ output line of the rescan backup flip flop 206 is connected to the output line RBU which is utilized to move the slow scan location of the beam an additional seven microns back so that the start of rescan will start sufficiently back that the entire cell will be included in the rescan. However, a gate is in the slow scan control to prevent the seven micron backup during the focus cycle. The seven micron backup is thus initiated at the start of the classification cycle.

The rescan sweep flip flop remains set during the period that the rescan counter reaches the count of four until the rescan counter reaches the count of 12 during the focus cycle and the count of 84 during the classification cycle. The rescan sweep flip flop is reset by the enabling of gate 226 which is connected to the reset input of the flip flop 206 and thereby causes the reset thereof as the output of gate 226 goes low. The Q line of the rescan flip flop 208 is connected to output line RS which is utilized to start a ramp generator which moves the beam in the slow scan direction ¼ micron in the period that the fast scan counter recycles. The ramp generator thus moves the beam 2 microns for each focus scan and 20 microns during the single classification scan.

The finish rescan flip flop 210 is set at the count of 84 in rescan counter 204. The setting of flip flop 210 enables gate 230 and thereby prevents the resetting of the rescan counter 204 until it reaches the count of 96 at the end of the classification cycle. At the time that the counter reaches the count of 96, AND gate 222 is enabled and thereby causes the finished rescan flip flop 210 to be reset thereby disabling gate 230 and resetting the rescan counter 204. The compute flip flop 212 is set by the enabling of AND gate 222. The compute flip flop remains set until the transfer time required for the transfer of information from the pattern recognition unit to the computer. This is indicated by a signal on the recognition line which resets the compute flip flop 212.

It can therefore be seen that, in summary, the slow scan timing accomplishes the following:

After a search scan has been completed, the slow scan counter 202 is backed up four counts to enable the scan to proceed in the slow scan direction from the initial point of a captured pattern. As soon as the rescan mode is started, the focus cycle is initiated thereby causing the rescan counter to recycle each time that it reaches the count of 12. During the counts of 4 through 12, the rescan sweep flip flop 208 is enabled which causes the narrow focus scan of eight lines during which time data counts are taken of the weighted quantization data.

As soon as the last focus scan is completed, and the focus cycle is thus completed, the rescan backup flip flop is set for the last time and thereby enables at the count of four the rescan sweep to be enabled which thereby causes the 20 micron classification scan in the slow scan direction during which time the pattern is classified. At the end of the 84 scan line during the classification cycle, the finish rescan flip flop is set to prevent the rescan counter from being reset until the count of 96 is reached. As soon as the counter 96 is reached, the classification mode is completed and the starch mode is started again.

MODE CONTROL

Figure 14:
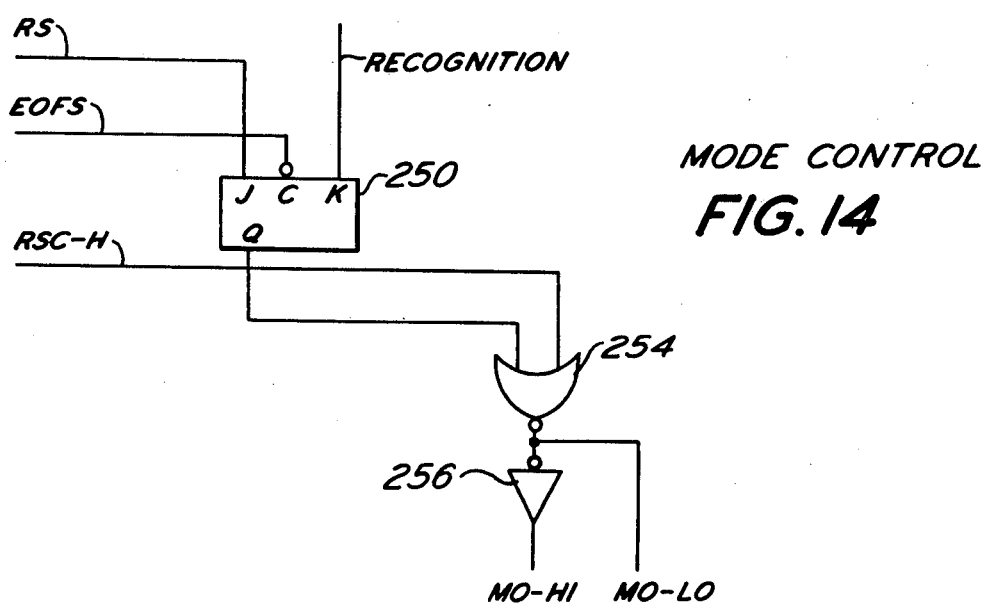
FIG. 14 is a schematic block diagram of the mode control unit.

Mode control circuitry is shown in FIG. 14. The mode control circuitry includes flip flop 250, an OR gate 254 and an invertor 256. The C input of the flip flop 250 is connected to the EOFS line, the J input is connected to the RS line, the K input is connected to the recognition line from the computer, and the Q output line is connected to the input of AND gate 252. The RS line is also connected to an input of OR gate 254. The RSC-H line is connected to the other input of OR gate 254. The output of the OR gate 254 is connected to an invertor 256 and to the MO-LO line. The output of invertor 256 is the MO-HI line.

The operation of the mode control is as follows:

During a search mode, flip flop 250 is in the reset state and the signal of the RSC-H line is low. Accordingly, OR gate 254 is disabled causing the MO-LO line to be high and the MO-HI line to be low. The RSC-H line goes high when the first EOFS pulse is received after a capture is made. This high signal on RSC-H enables OR gate 254 causing the Mo-HI line to go high and the MO-LO line to go low. The flip flop 250 remains in the reset condition until the line RS goes high when the count of four is reached in the rescan counter and the pulse signal on line EOFS is generated at the end of a fast scan causing the setting of flip flop 250. When flip flop 250 is set it continues to enable OR gate 254 until the mode flip flop 250 is reset by receipt of the recognition signal which is received on the K input of flip flop 250. Thus, if a recognition signal is not received before the count of 96 is reached in the rescan counter 204 (FIG. 11), the MO-LO signal stays low and prevents a search mode from being started.

COLOR PROCESSOR AND QUANTIZER

Figure 15:
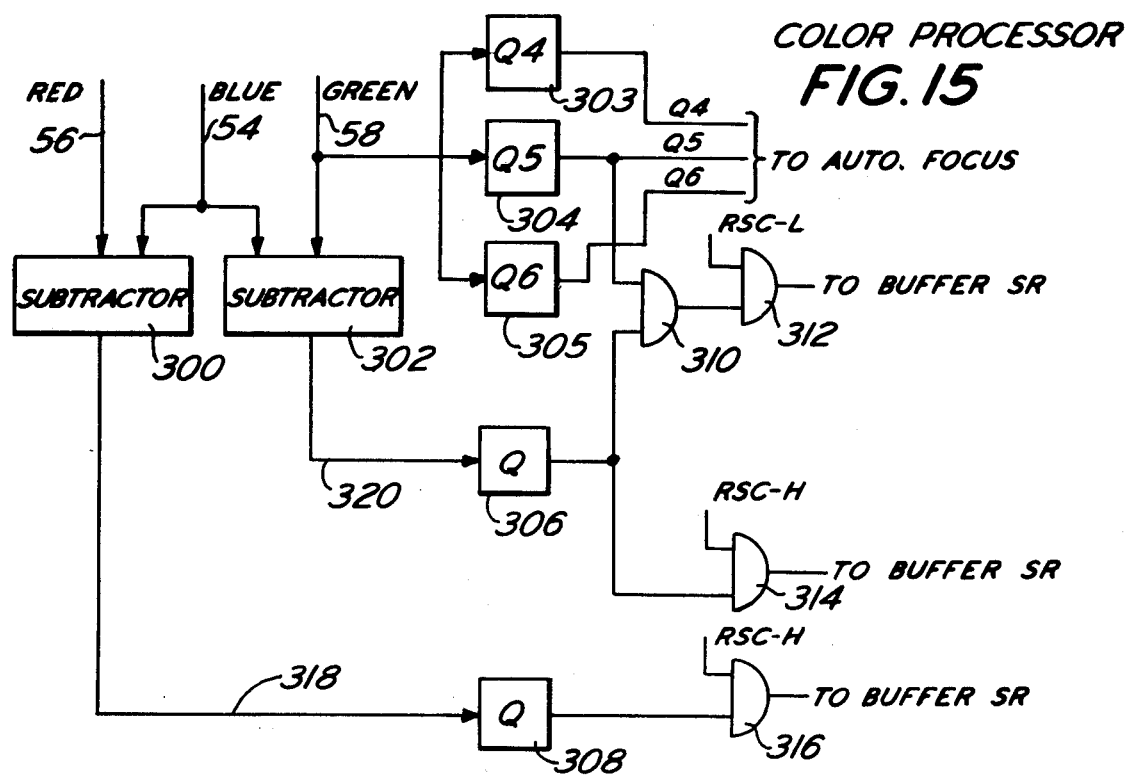
FIG. 15 is a schematic block diagram of the color processor and quantizer circuitry.

The color processor and quantizer is shown in FIG. 15. The color processor and quantizer includes a pair of subtractors 300, 302, five quantizers 303, 304, 305, 306 and 308 and four AND gates 310, 312, 314 and 316. The subtractor 300 receives the red and blue signals from lines 56 and 54 of the light component separator, subtractor 302 receives the blue signal and the green signal on lines 54 and 58, respectively. The difference signal from subtractor 300 is applied to the input of the quantizer 308 via line 318, the difference signal from subtractor 302 is provided via line 320 to quantizer 306, the output signal from the green input line 58 is also provided to quantizers 303, 304 and 305. The quantizer 304 and quantizer 306 are connected to the input of AND gate 310, the output of AND gate 310 is connected to the input of AND gate 312.

The outputs of the quantizers 303, 304 and 305 are connected to the Q4, Q5 and Q6 lines respectively. The Q4, Q5 and Q6 lines are connected to the automatic focus circuitry. The remaining input to AND gate 312 is the RSC-L input line. Quantizer 306 is connected to the input of AND gate 314 as well as AND gate 310. The AND gate 314 also includes an input line from RSC-H. Quantizer 308 is connected to the input of AND gate 316. The remaining input line is also connected to RSC-H. In operation the color processor enables preprocessing of the signals from the photomultiplier prior to their use by the pattern capture a pattern recognition circuitry.

During the search mode of operation the line RSC-L is high thereby passing the signal from AND gate 310. AND gate 310, in order to be enabled, requires that the quantizer 304 and quantizer 306 have reached their threshold level. The blue-green subtractor 302 provides a difference signal which substantially reduces the amount of red cell information present in the signal. Thus, the reaching of the threshold level in quantizer 306 indicates that a red blood cell is not present. The reaching of the quantizing threshold level in quantizer 304 indicates that this signal is dark enough to be a nucleus of a white blood cell but not the cytoplasm. This threshold level can also be reached by platelets. Thus, substantially the only information which would be provided via gate 310 to the AND gate 312 is that which is generated by the scanning of a white blood cell nucleus or a platelet. When the system is in the rescan mode the RSC-H signal is high. For classification the preferred quantized signal is the blue-green differential which is provided by the quantizer 306. Thus, the signal is pased via AND gate 314 to the buffer shift register during rescan for classification purposes by the pattern recognition system.

It should be understood that not only is the blue-green signal utilizable but also the green signal as well as the red-blue differential signal provided at the output of subtractor 300 and quantized by quantizer 308 and, as indicated at the bottom of FIG. 13, the signal from AND gate 316 is provided to the Buffer shift register. It should also be understood that more than one MOS shift register comprised of a plurality of 128 bit shift registers are provided. Also, as is also well known in the art, a plural parallel bit main shift register is provided wherein plural levels of quantized signals can be simultaneously examined by the pattern recognition circuitry. Thus, each of the color signals and difference color signals may be processed simultaneously during rescan.

PATTERN CAPTURE

Figure 16:
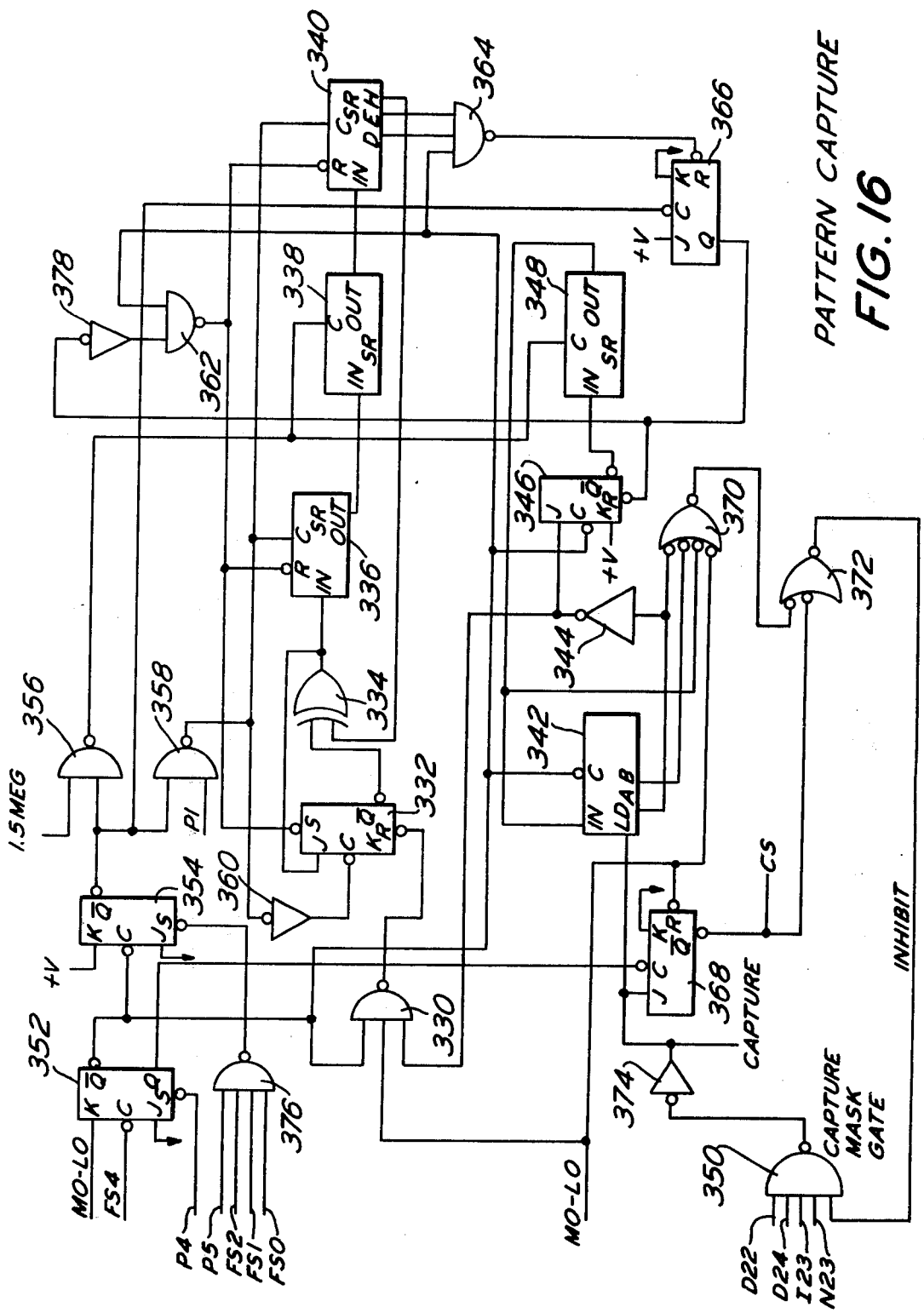
FIG. 16 is a schematic block diagram of the pattern capture circuitry.

The pattern capture circuitry is shown in FIG. 16. The pattern capture circuitry includes a capture location store and counter which is comprised of AND gate 330, flip flop 332, an EXCLUSIVE OR gate 334 and three shift registers 336, 338 and 340. The pattern capture also includes a fast scan area divider which is comprised of a shift register 342, an inventor 344, a flip flop 346 and shift register 348.

The pattern capture circuitry further includes the capture mask gate which is comprised of an AND gate 350. The timing circuitry associated with the capture location store and counter comprises flip flop 352, flip flop 354, AND gate 356, AND gte 358 and invertor 360. The circuitry for determining and causing the end of the pattern capture circuitry cycle includes AND gate 362, AND gate 364 and flip flop 366. The circuitry which inhibits a capturing of either the same cell or another cell within the same area that the previous white cell was captured or in adjacent areas includes a capture storage flip flop 368, OR gate 370, OR gate 372 and invertor 374. Cooperating with the timing circuitry is an AND gate 376.

The MO-LO line is connected to the K input of flip flop 352, an input of AND gate 330 and also to the reset inputs of flip flop 368 and an input of OR gate 370. The C input of flip flop 352 is connected to the output of the fast scan counter line FS4. The signal on FS4 goes low every 32 counts of the fast scan counter. Thus, since a search scan is 640 fast scan counts, the flip flop 352 is set twenty times during a fast scan sweep in the search mode. The set input of flip flop 252 is connected to the P4 line from the decoder which causes the flip flop 352 to be set immediately upon the next 1.5 megacycle pulse on line P4. The $\overline{Q}$ output line of flip flop 352 is connected to an input of AND gate 330, the clock input of flip flop 354, the clock input of shift register 342, the clock input of flip flop 346 and an input of AND gate 362.

The $\overline{Q}$ output line of flip flop 352 is connected to the clock input of flip flop 368. The J input of flip flop 352 is connected to ground. Flip flop 354 has its K input connected to +V, the clock input is connected to the $\overline{Q}$ output line of flip flop 352, the J input is connected to ground, the set input of flip flop 354 is connected to the output of AND gate 376 and the $\overline{Q}$ output line of flip flop 354 is connected to an input of AND gate 356, an input of AND gate 358 and to the clock input of flip flop 366. The second input to AND gate 356 is the 1.5 megacycle pulses which are used to shift the main shift register. The second input of AND gate 358 is the P1 pulse from the output line of the decoder in the basic timing which provides 1.5 megcycle pulses during phase 1. The output of AND gate 356 is connected to the clock input of both shift registers 338 and 348. The output of AND gate 358 is connected to the input of inverter 360, the clock input of shift register 336 and the clock input of shift register 340.

The inputs of AND gate 376 are connected to the output line P5 of the decoder of the basic timing and to output lines FS0, FS1 and FS2 of the fast scan counter. Since the output of AND gate 376 is connected to the input of flip flop 354, the flip flop 354 is opened up for a period of seven 1.5 megacycle pulses since the fast scan counter is counted at a 1.5 megacycle rate. The AND gate 330 receives not only the $\overline{Q}$ output line of flip flop 352 and the MO-LO signal on the MO-LO input line but also receives an input from the output of inverter 344. The output of AND gate 330 is connected to the reset input of flip flop 332. AND gate 352 receives its inputs from the Q output line of flip flop 366 and the $\overline{Q}$ output line of flip flop 352. The flip flop 332 of the capture location shore and counter has its C input connected to the output of invertor 360, its J input connected to the output of EXCLUSIVE OR gate 334, its rest input connected to the output of AND gate 330 and its $\overline{Q}$ output line connected to the input of the EXCLUSIVE OR gate 334. The EXCLUSIVE OR gate receives a second input from the H output line of shift register 340. In addition to feeding out one of its output lines to the J input of flip flop 332 the EXCLUSIVE OR gate output line is also connected to input line of shift register 336. Shift register 336 is a five bit shift register which receives its input pulses from the output line of EXCLUSIVE OR gate 334. The clock input line of the shift register 336 is connected to the output of AND gate 358. The output line of shift register 336 is connected to the input line of shift register 338. Shift register 338 receives the output signals from shift register 336 and its clock input line is connected to the output line of AND gate 356. The shift register 338 is a 128 bit shift register and the output line is connected to the input of shift register 340.

Shift register 340, in addition to receiving the output signals from shift register 338, has its reset input connected to the output of AND gate 362, its clock input connected to the output of AND gate 358, its D and E output lines are connected to the input of AND gate 364 and its H output line is connected to the second input of EXCLUSIVE OR gate 334. The shift register 340 is an eight bit shift register with the output lines D and E representing the fourth and fifth stages respectively of the shift register and the H output line representing the eighth stage output line of the shift register. The remaining input of AND gate 364 is the $\overline{Q}$ output line of flip flop 352.

The shift register 342 is connected as a two bit serial shift register. The input line to shift register 342 is connected to the output line of shift register 348. The load input line (LD) of shift register 342 is connected to the output of invertor 374. The clock input line is connected to the $\overline{Q}$ output line of flip flop 352. The A output line which represents the first stage of the shift register 342 is connected to a first input of OR gate 370 and to the inverter 344. The B output line of the shift register 342 is connected to another input of the OR gate 370. The output of invertor 344 is connected to the J input line of flip flop 346 and to the input of AND gate 330. Flip flop 346, in addition to receiving the output of inverter 344 at the J input, has the C input line connected to the $\overline{Q}$ output of flip flop 352, the K input connected to $+V$ and the $\overline{Q}$ output line is connected to the input line of shift register 348. Shift register 348 is a 128 bit shift register which receives its clock pulses from the output of AND gate 356. The output line of shift register 348 is connected to the input line of shift register 342. The output of shift register 348 is also connected to the third input of the OR gate 370. The fourth input of the OR gate 370 is connected to the MO-LO line. The output of OR gate 370 is connected to an input of OR gate 372. OR gate 372 also receives the input from the $\overline{Q}$ output line of the capture flip flop 368. The J input line of flip flop 368 is connected to the output of invertor 374. The C input line of flip flop 368 is connected to the Q output line of flip flop 352. The K input of flip flop 368 is connected to ground and the reset input of flip flop 368 is connected to the MO-LO line.

The output of OR gate 372 is connected to an input of the capture mask gate 350. The remaining input lines to the AND gate 350 are output lines D22, D2;4, I23 and N23 from the aperture shift register of the main shift register in FIG. 7.

The flip flop 366 which is used to terminate the pattern capture cycle is connected as follows:

The Q output line is connected to the input of AND gate 362 and to the rest input of flip flop 346. The J input is connected to $+V$, the C input is connected to the $\overline{Q}$ output line of flip flop 354 and the K input is connected to ground. The reset input is connected to the output of AND gate 364.

The operation of the pattern capture circuitry is as follows:

During the search mode of operation the MO-LO line is high which thereby causes the flip flop 352 to be reset every 32 counts in the fast scan counter. That is, the fast scan counter line FS4 goes low every 32 1.5 megacycle counts. The flip flop remains set only until the next 1.5 megacycle pulse on line P4 during phase 4 of the 1.5 megacycle pulses. When the system is in a rescan mode of operation, the MO-LO line is low thereby preventing the flip flop 352 from being reset and causing pulses every 32 counts in the fast scan counter. Each time flip flop 352 is set, the $\overline{Q}$ output line goes low thereby causing the flip flop 354 to be reset. The flip flop 354 stays reset for 7 counts until the AND gate 376 is enabled 7 fast scan counts later and causes the flip flop 354 to be reset.

The AND gates 356 and 358 are enabled seven times during the time that flip flop 354 is in the reset state. The 1.5 megacycle pulses to AND gate 356 cause a different enabling period than the P1 pulses to gate 358 because the P1 pulses are positive in a different phase of the 1.5 megacycle pulse.

Shift registers 336, 338 and 340 are effectively a 140 bit shift register which is constantly recirculated. Normally, the shift register comprising shift registers 336, 338 and 340 have zeros recirculating throughout the 140 bits of the shift register. Each 7 bits of the 140 bit shift register effectively represent an area of 32 counts in the fast scan direction. Thus, when information is put into any one of the 20 7 bit locations, that information in the 7 bits represents the location of the capture which is stored as the shift register is recirculated. The flip flop 332, in combination with the EXCLUSIVE OR gate 334 effectively increment the count in the seven bits each time the seven bits are recirculated completely through the 140 bits represented by shift registers 336, 338 and 340.

There is thus a complete recirculation of the 140 bit shift register for each complete fast scan cycle in the search mode. The 140 bit shift register is thus synchronized with the fast scan counter.

The fast scan area divider is also effectively a 140 bit shift register as a result of the operation of shift registers 342 and 348. Shift register 342 normally has ones recirculating through the shift register as a result of the fact that the input line to the J input of flip flop 346 is normally low in the search mode until a capture has occured. Until that time, the output signal on the $\overline{Q}$ output line of flip flop 346 is normally high which thereby causes the shift pulses to shift register 348 on the clock input line to shift ones through the 128 bit shift register 348. As soon as the capture mask gate 350 is enabled, the shift registers 342 and 348 operate to divide the fast scan into the twenty discrete areas so that the capture mask can be inhibited from making any further detections of white cells in the area in which capture is made or the adjacent areas during the next 24 lines in the slow scan direction. When AND gate 350 is enabled it causes the output line thereof to go low which is inverted to a high input pulse on the J input of flip flop 368 and to the load input of shift register 342. As soon as a zero is put into the first stage of the shift register 342, output line A causes the J input of flip flop 346 to go high and also causes AND gate 330 to be enabled as soon as the flip flop 352 is reset.

Upon the first resetting of flip flop 352 after capture has occurred, the Q output line first goes negative and thereby causes the capture storage flip flop 368 to be set. The $\overline{Q}$ output line of flip flop 352 then goes low when the next P4 pulse sets the flip flop 352 again causing shift register 342 to shift the zero from the first stage to the second stage thereby causing the B output line to go low and the flip flop 346 to be primed to be set, on the next negative going pulse from the $\overline{Q}$ output line of flip flop 352. The setting of flip flop 352 also causes the enabling of AND gate 330 which causes the resetting of flip flop 332. When the flip flop 332 is reset the $\overline{Q}$ output line thereof goes high which causes the enabling of EXCLUSIVE OR gate 334 since the remaining input to the OR gate is a low input from the shift register 340. The high output signal on the output line of EXCLUSIVE OR gate 334 thus provides a one input to the first stage of shift register 336 when the next 1.5 megacycle pulse during phase 1 enables gate 358 and thereby causes the setting of flip flop 332 and the placement of a one input in the first stage of shift register 336.

The setting of the flip flop 346 in the fast scan area divider causes the $\overline{Q}$ output line of flip flop 346 to go low and thus seven zero bits are placed into shift register 348 as the clock input thereof receives seven pulses from AND gate 356 until the next resetting of flip flop 352 causes the flip flop 346 to be reset. The seven zero bits are then shifted through the shift register 348.

Although shift register 348 is only 128 bits long and the shift register 342 is only two bits long, there is nonetheless the operation of a shift register of 140 bits long simulated thereby. The reason is that shift register 342 effectively adds seven bits to shift register 348 since the shift register 342 is shifted only once every 32 counts instead of seven times every 32 counts as is shift register 348. Thus, the effective length of shift register 348 and 342 is 135 bits long. Even though 128 pulses are required to shift all of the information through shift register 348, it only requires one bit at the output of shift register 348 to load a zero into the shift register 342. That is, since the shift register 342 had information shifted in by the negative going pulse on the clock input line from the switching of flip flop 352, only the last bit in the shift register 348 must be a zero in order to accomplish this since the negative going signal to the clock input line of shift register 342 occurs during the first of the seven 1.5 megacycle clock pulses which shift the shift register 348.

As soon as the zero has been inserted into shift register 342 it remains there for seven counts prior to being placed into the flip flop 346 to provide the second set of counts in the first seven stages of the shift register 348. Thus, the shift registers 342 and 348 act to effectively divide the fast scan direction into 20 discrete areas. In addition, each time that the seven bits corresponding to the location of the capture in the shift registers 336, 338 and 340 is recirculated, it is recirculated through the EXCLUSIVE OR gate 340 which is connected to the input of shift register 336.

Thus, after the one bit in the seven bits is recirculated through shift registers 336, 338 and 340, the one bit is applied to the EXCLUSIVE OR gate 334 after it has been recirculated through the 140 bits of the shift register. However, since the zero bits in the shift register 348 have been provided to the input of shift register 342 in synchronism with the seven bits floating through shift register 338 and 340, the A output of shift register 342 causes the AND gate 330 to be enabled via the invertor 334. The enabling of AND gate 330 causes the flip flop 332 to be reset and thereby causes a one to be provided at the other input of EXCLUSIVE OR gate 334 at the time that the first bit of the shift register has recirculated to the EXCLUSIVE OR gate 334. Since the EXCLUSIVE Or gate is enabled only when one of the inputs is at a high level, a zero is then placed in the first stage of the shift register 336 by the clock pulse from AND gate 358. Also, because the output of the EXCLUSIVE OR gate is low, the flip flop 332 does not set upon the clock pulse being applied by the invertor 360 to the clock input of flip flop 332.

Since the one bit has been shifted out of shift register 340, the first input to the EXCLUSIVE OR gate 334 now goes low. However, since the input from the $\overline{Q}$ output line of flip flop 332 remains high the EXCLUSIVE OR gate shifts a one bit into the shift register 336 during the next clock pulse from AND gate 358 thereby providing a one in the second bit of the seven bits which are representative of the location of the capture of a white cell in the fast scan direction. After another complete recirculation of the 140 bits in the shift registers 336, 338 and 340, the first bit of the seven bits provided to the EXCLUSIVE OR gate 334 is a zero and therefore since the flip flop 332 has been reset again the high signal on the $\overline{Q}$ output line of flip flop 332 causes the enabling of the EXCLUSIVE OR gate and a placement of a one in the first position of the seven bits into shift register 336.

The second bit of the seven bits provided by shift register 340 is a one bit thereby providing a high signal to the EXCLUSIVE OR gate 334 from shift register 340 but, since the flip flop 332 was set by the high output previously on the output of EXCLUSIVE OR gate 334, the second input to the EXCLUSIVE OR gate is a low input and thereby causes a second enabling of the EXCLUSIVE OR gate 334 thereby providing two ones in the first two bits of the seven bits representative of the capture location.

During the next 140 bit recycling of the shift registers 336, 338 and 340, the first bit of the seven bits causes the occurence of a high signal on both input lines of the EXCLUSIVE OR gate as the flip flop 332 is reset again by the location of a zero in the first stage of shift register 342. Thus during the first bit applied to shift register 336 the output of EXCLUSIVE OR gate is low thereby providing a zero bit to the first of the seven bits provided to the shift register 336. During the second bit the Q output line remains high since the flip flop has not been set by enabling of the EXCLUSIVE OR gate 334 thereby causing the second bit to be placed into the shift register 336 by EXCLUSIVE OR gate 334 to be another zero. Since only two ones were present in the last stages of shift register 340 the next bit provided to the last stage of shift register 340 causes a low signal to be applied to the first input of EXCLUSIVE OR gate 334 and only a single high signal is provided from the $\overline{Q}$ output line of flip flop 332 thereby enabling EXCLUSIVE OR gate 334 and putting a one into the third bit of shift register 336. The count in the seven bits of the shift register 336 is now 001 which is the binary representation of a decimal 4 indicating that this is the fourth recirculation of the seven bits representative of the capture location being shifted through shift register 336, 338 and 340.

When the count has reached 24 in the seven bits, during the twenty fourth circulation of these seven bits, the shift register 340 ultimately receives the count of 24 in the last seven bits of the shift register 340 which causes the AND gate 364 to be enabled when the count of 24 is in shift register 340 at the time that the flip flop 352 is reset by the FS4 line. When AND gate 364 is enabled, the flip flop 366 is reset thereby enabling the resetting of flip flop 346 and the enabling of AND gate 362 via invertor 378. When AND gate 362 is enabled the shift register 340 is reset thereby removing the count of 24 from the seven bits in shift register 340 and the resetting of flip flop 346 causes a loading of ones into the shift register 348, instead of receiving the zeros from shift register 342. Thus, effectively, the shift register 348 is reset to its original condition in a search mode after the seven bits representative of the capture location have been circulated through shift registers 336, 338 and 340 24 times.

During the time that the zeros are recirculating through the shift register 348 and shift register 342 comprising the fast scan area divider, the zeros at the location of the pattern capture cause the OR gate 370 to be enabled which in turn causes OR gate 372 to be enabled which causes the inhibit signal on the capture mask gate 350 which prevents an additional capture during the twenty-four fast scan lines of search. It should be noted that the capture mask gate is inhibited not only during the area that the capture mask was enabled, but also in the adjacent areas on each side of the area in which the capture was made. That is, the OR gate 370 is enabled not only by a zero in the first stage of shift register 342 but also the second stage output line B is also connected to OR gate 370 which thereby causes the enabling of the OR gate 370 when the zero is in the second stage of shift register 342. In addition, prior to the zero being loaded into shift register 342, the output of the last stage of shift register 348 is also connected to the OR gate gate 370 thereby disabling the OR gate 370 in the area prior to the area in which the capture is made.

When capture is originally made and AND gate 350 is enabled, the capture storage flip flop 368 is set upon the first resetting of flip flop 352. As soon as the capture flip flop 368 is set, the $\overline{Q}$ output line thereof goes low causing the OR gate 372 to be enabled to inhibit the capture mask gate 350 from being enabled as long as the capture storage flip flop remains set. What this means is that if a cell is captured in the upper portion of the fast scan line direction, no further capture can be made for the entire fast scan line. Thus, for example, in FIG. 2, the white cell 102 is in the area of the fast scan direction between the 30 and 48 micron distance in the fast scan direction. Thus, the fast scan counter would have only reached somewhere between 60 and 96 when the white cell 102 is detected. As soon as the capture storage flip flop 368 is set by the capturing of the pattern in the area between 64 and 96 of the fast scan count, the storage flip flop 368 enables the OR gate 372 and thereby inhibits the further capture of a pattern during the entire time that is required to complete the count of 640 in the fast scan counter.

As soon as the fast scan count reaches 640 the rescan mode of operation is initiated thereby causing the MO-LO signal to go low and thereby reset the flip flop 368. Thus, the function of the capture storage flip flop 368 is to prevent a second capture during the fast scan line that must be completed after capture is made.

There is thus a partial circulation of the seven bits representing the capture location in the shift registers 336, 338 and 340 when the low signal on the MO-LO line to flip flop 352 causes no further pulses to be provided to either of the capture location storage registers and counter and the fast scan area divider until the rescan mode of operation has been completed and classification of the white cell has been made. Thus, during the next 24 lines no further white cells can be captured in the area where the previous white cell was captured. It should also be understood that the fast scan area divider and the capture location store and counter can simultaneously process more than one capture. That is, if a second white cell is captured or detected in another area of the fast scan direction within the next twenty-four lines, seven bits representative of the capture location store comprising shift registers 336, 338 and 340 would be incremented to a one and a zero would be loaded into shift register 342 in another portion of the 140 bits circulating through the shift register.

Thus, while the count in the seven bits representative of the first cell scanned would be incremented by the flip flop 332 in combination with EXCLUSIVE OR gate 334, the second seven bits which represent the area that the second cell was captured in would also be incremented by the flip flop 322 in combination with EXCLUSIVE OR gate 334 as these bits are recirculated in the capture location storage register. In view of the fact that 20 discrete areas are defined by the fast scan area divider, the pattern capture circuitry could simultaneously process several captures. That is, each capture inhibits three areas. Thus, six captures, each spaced two areas apart, inhibits eighteen total areas and thereby prevents any further capture in these areas.

WINDOW CONTROL

Figure 17:
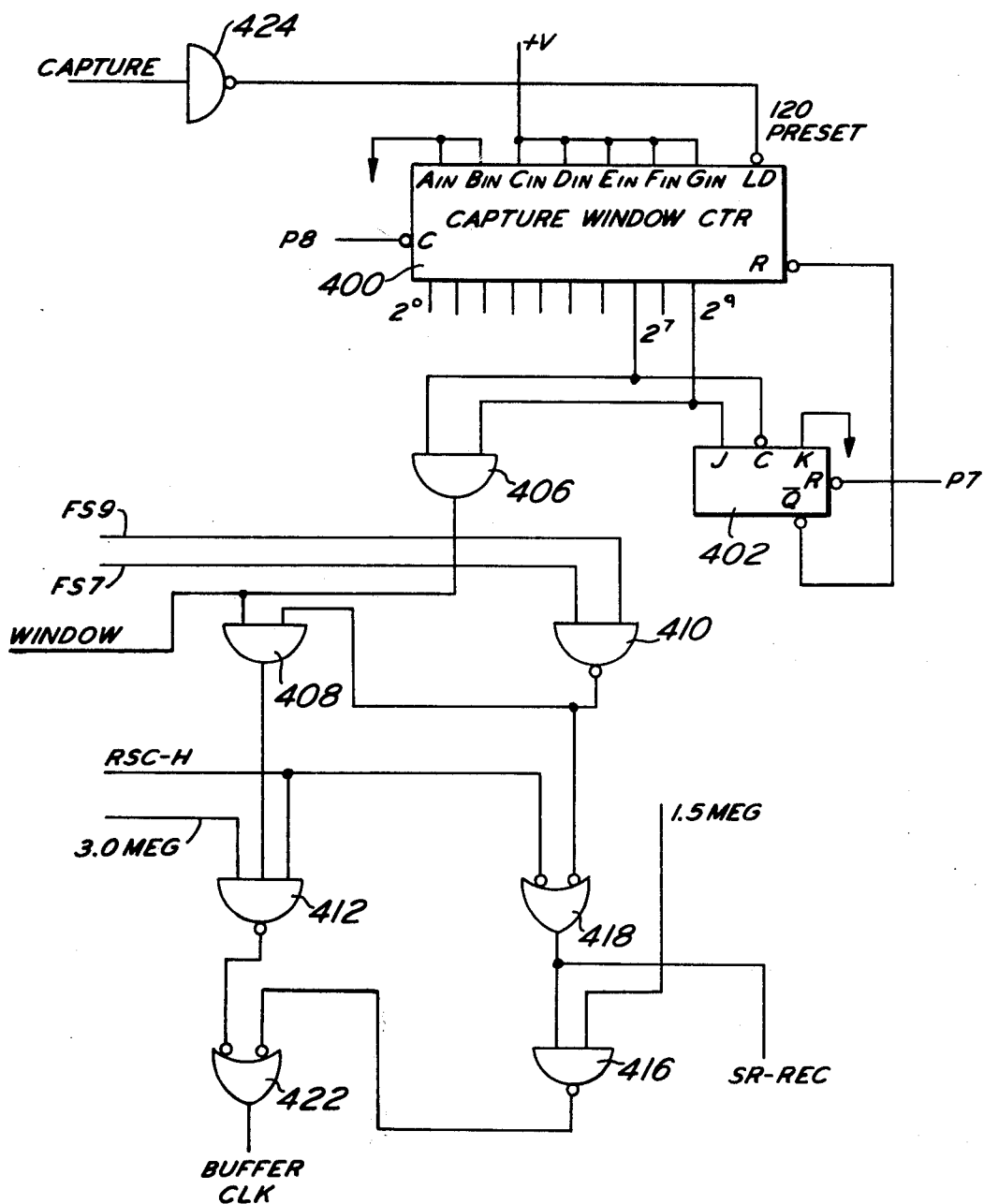
FIG. 17 is a schematic block diagram of the window control circuitry.

The window control circuitry is shown in FIG. 17. The window control basically comprises a capture window counter 400, flip flop 402, AND gates 406, 408, 410, 412 and 416 and OR gates 418 and 422,. The window control also includes an invertor 424. The input of the invertor 424 is the capture signal from the output of invertor 374 in the pattern capture circuitry of FIG. 14. The capture signal goes high immediately upon the detection of a white cell. The output line of invertor 424 is connected to the load input of the capture input counter 400 and causes the capture window counter to be present to a count of 120 as soon as the capture is made. The capture window counter includes inputs to the first and second stages which are labelled AIN and BIN, respectively, which are connected to ground. The capture window counter also includes inputs CIN, DIN, EIN, FIN and GIN which are connected to the third through seventh stages of the capture window counter and each of these inputs are connected to $+V$.

The capture window counter is a conventional binary counter which can be present in accordance with the signals provided on the input lines to the stages thereof. Thus, when the low input is provided to the load input of the capture window counter it presets each of the stages in the counter in accordance with the input signal provided to the stages. Thus, effectively, a one is placed into the stages 3 through 7 by the high input signal on lines CIN through GIN and a zero is placed in the first two stages by the ground input to AIN and BIN when the low signal is applied to the load input of the capture window counter. This provides a binary count of 120 in the capture window counter.

The capture window counter also includes a C input which is connected to the output line P8 of the timing decoder. The capture window counter is thus stepped at a rate of 1.5 megacycles by the signal on line P8. The capture window counter also includes a reset input which resets the capture window counter to zero at the reaching of the count of 767 in the counter.

The output lines of the capture window counter are respectively labelled $2^0$ through $2^9$. The $2^7$ output of the capture window counter is connected to an input of AND gate 406 and to the C input of the flip flop 402. The $2^9$ output of the capture window counter 400 is connected to the other input of AND gate 406 and to the J input of flip-flop 402. The output of AND gate 406 is connected to the input of AND gate 408 via a line which is labelled WINDOW. The reasons for the labelling of the WINDOW line as such is due to the fact that the AND gate 406 is enabled during the count of 640 to 767 in the capture window counter. That is, the $2^7$ and $2^9$ output lines of capture window counter both go high at the count of 640. The $2^7$ line stays high for another 127 counts and then goes low thereby disabling gate 406 and thereby causing the end of the high signal on the window line. This signal, when it is high, effectively enables the transfer of data from the buffer shift register into the main shift registers for classification analysis by the pattern recognition system. The Window signal also enables the weighted binary quantization count during each focus scan so that only data generated in the window surrounding the captured white cell is counted.

The flip-flop 402, in addition to receiving clock pulses from the $2^7$ output line of the window counter has its J input connected to the output line $2^9$ of capture window counter 400. The K input is connected to ground and the R input is connected to output line P7 of the timing decoder. The $\overline{Q}$ output line of flip flop 402 is connected to the reset input of capture window counter 400.

Gate 408 has one of its input lines connected to the window line and a second input connected to the output of AND gate 410. The output line of AND gate 408 is connected to an input of AND gate 412. The AND gate 410 has both of its inputs connected to the outputs of the fast scan counter and specifically to lines FS9 and FS7 thereof. Gate 410 is thus enabled during the count of 640 to 767 in the fast scan counter. The output of gate 410 is connected to the input of gate 408 which thus causes a disabling of the gates 408 by the low signal on the output of gate 410 when the period in the fast scan counter from 640 to 767 coincides with a portion of the period from 640 to 767 in the capture window counter.

Gate 410 is thus provided to inhibit the transfer of information to the main shift register if a capture of a pattern has been obtained too close to the lowermost edge of the field in the fast scan direction to prevent the classification of an incomplete pattern. The output of AND gate 410 is also connected to an input of OR gate 418.

The RSC-H line from OR gate 230 in FIG. 13 is also connected to an input of OR gate 418 and an input of AND gate 412. The third input to AND gate 412 is the 3.0 MEG line which provides pulses at a 3.0 megacycle rate to the AND gate 412. The output of AND gate 412 is connected to an input of OR gate 422. The output of OR gate 418 is connected to an input line of gate 4116. The other input of AND gate 416 is then 1.5 megacycle line. The output of both AND gate 412 AND gate 416 are provided to the input lines of the Or gate 422 which is connected to the BUFFER-CLK line which is fed to the clock input of the buffer shift register. The output line of the OR gate 418 is connected to the SR-REC line which is connected to the R input line of shift register SR1 through SR26.

The capture window counter 400 is stepped at a rate of 1.5 megacycles as is the fast scan counter 190. In fact, both are stepped in the same phase by the P8 pulses from the decoder in the main timing. The purpose of the capture window counter is to establish a coordinate set to allow sampling and scanning of the white cell for the purpose of automatic focusing and classification. It will be remembered that at the time the capture pulse is generated, not only is the capture window counter present to 120, but also, as set forth above in the slow scan direction, the scan is backed up four lines to correspond to the distance of the capture mask and the slow scan counter is then fixed. During the rescan a plurality of focus scans which traverse only two microns are generated and another minor scan which traverses 20 microns for classification purposes is generated about this slow scan position. As will hereinafter be seen, these minor scans are generated by a slow scan ramp generator which moves to the right in the slow scan direction from the point of capture for 2 microns in each focus scan and from a point 7 microns to the left of the four line backup position for 20 microns during the classification scan.

In the fast scan direction the presetting of the capture window counter to 120 causes the pattern captured to be at the center of the field sampled and scanned in the rescan mode. The reason is that a 128 count additional period is utilized for the blanking interval between the counts of 640 and zero. This enables the capture window counter to be decoded to establish a window for sampling and shifting the data in the quantized video into the shift register during the rescan mode for cell classification.

It will be remembered that a pattern is captured in the aperture shift register comprises of shift registers SRA to SRZ. The center position in the fast scan direction of the capture pattern in the aperture is position 23 of shift registers SRD, SRI and SRN. This position in combination with the extra eight bits (the capture window counter is set to 120 rather than 128) means the bottom of the window is 31 counts from the point of capture.

Since the cell capture window is 64 counts wide, this places the cell in the approximate center of this window. That is, in the rescan mode the cell window appears to be 128 bits long because there are two samples for each count. The two samples for each count is caused by the 3.0 megacycle rate of sampling which is provided to the buffer register via the AND gate 412 and OR gate 422 to BUFFER-CLK line. Although the window line which enables the AND gate 412 is 128 counts long and therefore enables 256 3 megacycle pulses to be fed to the clock input of the buffer shift register in FIG. 7, the first 128 bits provided to the buffer shift register 150 are shifted out on line 172 and are not used since the shift register SR1 through SR26 has a low input pulse on the R input line to prevent any reception of data from input line 172 to the shift register. The second 128 bits are stored in the buffer shift register and are then fed out to the shift register SR1 at a 1.5 megacycle rate after the window is terminated and during the count of 640 to 767 in the fast scan counter. Shift register SR1 receives the data from the buffer shift register since the SR-REC line goes high during the fast scan count of 640 to 767.

Referring back to the window control circuitry in FIG. 17, it can therefore be seen that the window signal, when it is high, causes the enabling of AND gate 412 via AND gate 408 unless AND gate 410 is enabled by the fast scan counter during the same time that the window is generated by the capture window counter. Thus during the window, the AND gate 412 is enabled by the RSC-H line which is high during rescan to pass the 3.0 megacycle pulses to the buffer shift register via OR gate 422.

When the RSC-H is low during the search mode of operation, the OR gate 418 is enabled thereby enabling the AMD gate 416 to pass 1.5 megacycles pulses to the buffer shift register via OR gate 422 during the search mode of operation. The flip flop 402 controls the recycling of the capture window counter 400. At the count of 640, the $2^9$ output line goes high thereby providing a positive voltage at the J input of flip flop 402. The $2^7$ output line of the capture window counter then goes negative after the count of 767 has been reached thereby causing the flip flop 402 to be set causing the output signal on $\overline{Q}$ output line of flip flop 402 to go low and cause the resetting of the capture window counter to zero.

The flip flop 402 remains set for only a short period of time because the next pulse on line P7 causes the flip flop 402 to be reset and thereby removes the reset signal from the capture window counter 400 and enables the next pulse of the P8 line to set a one into the capture window counter. The output line SR-REC which controls the shift registers SR1 through SR26 is high during the entire search mode as a result of OR gate 418 being enabled by the low signal on the RSC-H line during the search mode. The SR-REC signal is high during the rescan mode of operation only at the time that AND gate 410 is enabled which is during the time that the fast scan counter goes from 640 to 767. It can therefore be seen that the enabling of OR gate 418 during both the search mode and the period of 640 to 767 of the fast scan count means that 1.5 megacycle shift pulses are provided to the buffer shift register only during a search mode or during the period of time that the count goes from 640 to 767 in the fast scan counter. The only other pulses that are fed to the shift register during the rescan mode is during the period that the window is open and the 3.0 megacycle pulses are fed by the enabling of AND gate 412 and the passing by OR gate 422 of the pulses to the buffer shift register.

FAST SCAN CONTROL

Figure 18:
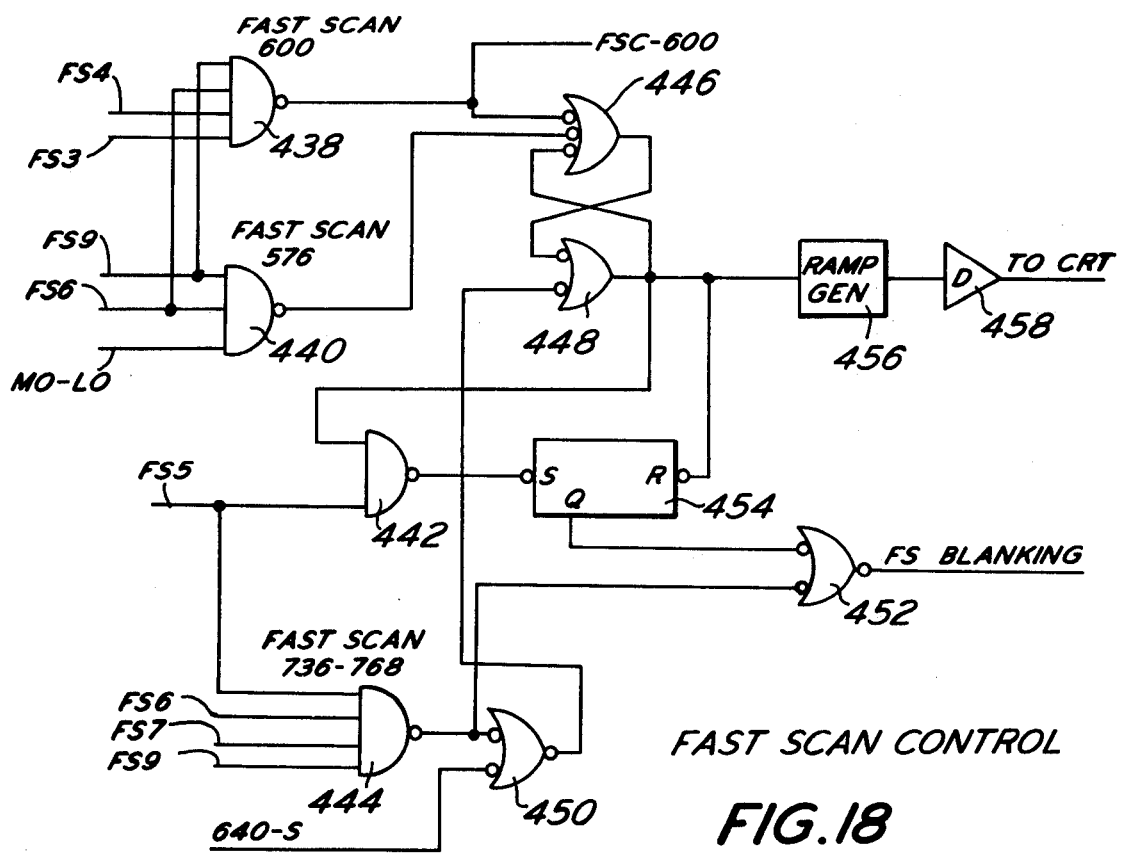
FIG. 18 is a schematic block diagram of the fast scan control circuitry.

The fast scan control circuitry is shown in FIG. 18. Basically, the fast scan control circuitry comprises AND gates 438, 440, 442 and 444, OR gates 446, 448, 450 and 452, a flip flop 454 and a ramp generator 456 and a drive amplifier 458. The AND gate 438 has its four inputs connected to output lines FS3, FS4. FS6 and FS9 of the fast scan counter. Thus AND gate 438 is enabled when the fast scan counter reaches the count of 600. The output line of AND gate 438 is connected to output line FSC-600 and to an input of OR gate 446. AND gate 440 is connected to two outputs of the fast scan counter, output lines FS9, and FS6. The remaining input of AND gate 440 is connected to the MO-LO line which is high only during the search mode. Thus during the search mode the AND gate 440 is enabled when the fast scan counter reaches the count of 576. The output of AND gate 440 is connected to another input of OR gate 446. OR gate 446, in addition to having inputs from the output lines of AND gates 438 and 440, also has an input line connected to the output of OR gate 448. The output of OR gate 446 is connected to the input of OR gate 448. The second input of OR gate 448 is connected to the output of OR gate 450. The output of OR gate 448 is connected to ramp generator 456. The output of the ramp generator 456 is connected to the input of the drive amplifier 458 which is connected to the vertical deflection coil of the cathode ray tube.

AND gate 442 has an input line connected to the output line FS5 of the fast scan counter which goes high when the fast scan counter reaches the count of 32. The other input of AND gate 442 is connected to the output of OR gate 448. The output of AND gate 442 is connected to the set input of flip flop 454. The output of AND gate 442 is enabled only when OR gate 448 has been enabled and the FS5 line goes high. The output of AND gate 442 is connected to the set input of flip flop 454. The R input of flip flop 454 is connected to the output of OR gate 448. The Q output line of flip flop 454 is connected to an input of OR gate 452. The remaining input of OR gate 454 is connected to the output of AND gate 444. The output of OR gate 452 is connected to the FS BLANKING line. AND gate 444 is connected to the FS5, FS6, FS7 and FS9 output lines of the fast scan counter. The output of AND 444 is connected to the input of OR gate 450. The remaining input to OR gate 450 is connected to the output of the AND gate 192 in the fast scan timing of FIG. 10 labelled the 640-S line. The 640-S line is high whenever the fast scan counter reaches the count of 640 in the search mode.

The OR gates 446 and 448 form a flip flop with the output of the flop flop connected from the output line of OR gate 448 being connected to the ramp generator 456. When the output of OR gate 448 goes high the ramp generator 456 starts a sawtooth wave or ramp voltage generation which is fed via the driver amplifier 458 to the vertical deflection beam of the cathode ray tube and thereby causes a vertical sweep in the fast scan direction.

When the output of OR gate 448 goes low, the voltage on the output of the ramp generator immediately goes towards zero and continues to go to zero until the voltage is high at the output of OR gate 448 and thereby starts another ramp.

During the search mode, the ramp generator causes a vertical sweep during the fast scan count of zero to 576. At the count of 576 AND gate 440 is enabled thereby causing the enabling of OR gate 446 which thereby causes the OR gate 448 to be disabled and thereby to provide a low signal to the ramp generator causing a retrace. In the search scan when the count of 640 is reached the 640-S line goes low thereby enabling the OR gate 450 and thereby enabling in turn OR gate 448. When OR gate 448 is enabled the ramp generator 456 starts another ramp at the count of zero in the fast scan counter. The ramp continues until the count of 576 is reached, then there is a retrace at the count of 640 in the fast scan counter is zero, because the fast scan counter is reset at 640 the ramp generator again begins another sawtooth wave to cause another vertical sweep.

In the rescan mode the OR gate 446 is enabled when AND gate 438 is enabled at the fast scan count of 600. Thus, there is a retrace of the scan line starting at the count of 600. The OR gate 448 remains disabled until the fast scan count reaches the count of 736 which thereby causes AND gate 444 to be enabled which in turn enables the OR gate 450 which enables OR gate 448. Thus, the retrace is terminated at the count of 736 and the ramp generator is again started. The OR gate 448 remains enabled until the fast scan counter again reaches 600 when a retrace line is started by the voltage going towards zero at the output of ramp generator 456.

The reason that the OR gate 448 is enabled at the count of 736 in the fast scan counter during the rescan mode of operation is that the starting of the ramp voltage when the count is 736 enables much greater linearity of the ramp between the count of zero and 600 in the fast scan counter.

Flip flop 454 is reset whenever the OR gate 448 is disabled. When the flip flop 454 is in the reset mode, the OR gate 452 is enabled, which enabling signal is utilized for the purpose of blanking the CRT tube during the retrace time. After the OR gate 448 is enabled, it primes AND gate 442 to be enabled when the count in the fast scan counter reaches the count of 32. In the search mode, flip flop 454 is not set until the fast scan counter reaches the count of 32 and thus between the count of 576 in the fast scan counter until the fast scan counter reaches the count of 32 the beam remains blank. In the rescan mode of operation, the OR gate 452 is controlled by the AND gate 44 which is enabled during the period that the fast scan counter counts from 736 to 768. Until the fast scan counter reaches 736 the OR gate is enabled by the flip flop 454. Thus, the CRT remains blank between the time that the fast scan counter is between the counts of 600 and 768.

SLOW SCAN CONTROL

Figure 19:
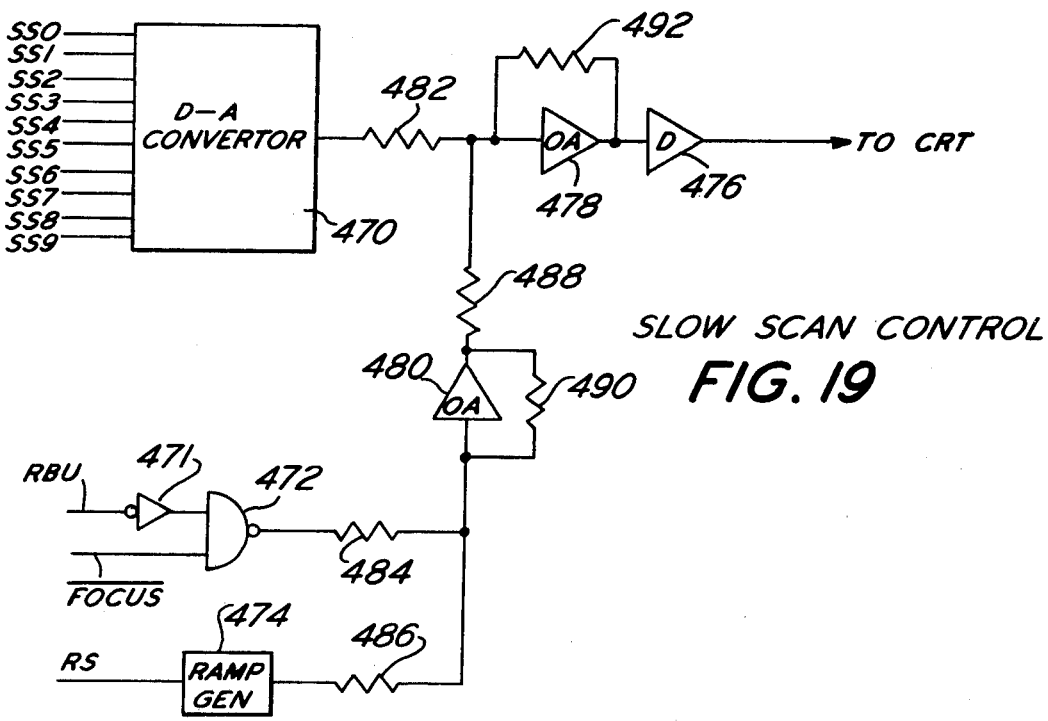
FIG. 19 is a schematic block diagram of the slow scan control circuitry.

The slow scan control circuitry is shown in FIG. 19. The slow scan control includes a digital to analog convertor 470, an inverter 471, an AND gate 472, a ramp generator 474, a driving amplifier 476, a pair of operational amplifirs 478 and 480, resistors 482, 484, 486, 488, 490 and 492. The digital to analog converter has inputs which are connected to the output lines SS0 through SS9 of the slow scan counter 202 in FIG. 11. The digital to analog converter converts the digital inputs on lines SS0 through SS9 to an analog signal which is provided on its output lines which is connected to resistors 482. Resistor 482 is connected to the input of an operational amplifier 478. The operational amplifier has a feed back resistor 492 connected across its input and output terminal.

The operational amplifier 478 is connected to the input of a driving amplifier 476, the output of which is connected to the horizontal deflection coil of the cathode ray tube. The inputs of AND gates 472 are connected via inverter 471 to the output line RBU which is connected to $\overline{Q}$ output of the rescan backup flip flop 206 in FIG. 13 and to the $\overline{FOCUS}$ line from the automatic focus circuitry. The output of the AND gate 472 is connected to a summing resistor 484. Summing resistor 484 is connected to the input of operational amplifier 480. The operational amplifier 480 has a resistor 490 connected across its input and output terminal for feedback. The output of the operational amplifier is connected to the input of operational amplifier 478 by a summing resistor 488. The RS output line from the Q output line of the rescan sweep flip flop 208 in FIG. 13 is connected to the input of ramp generator 474. The output of ramp generator 474 is connected to the input of operational amplifier 480 via the summing resistor 486.

The horizontal deflection coil of the cathode ray tube which controls the location of the beam along the slow scan direction is bascially controlled by the slow scan counter 202 in FIG. 13. As the count in the slow scan counter is increased, the voltage applied from the digital to analog converter to the operational amplifier 478 is also increased. In the search mode of operation, the slow scan counter is incremented one step for each fast scan and thus the digital to analog converter provides discrete voltage step up for each movement of the beam in the slow scan direction. For each step up of the count in the slow scan counter the beam is translated 1 micron on the field of the blood smear. When the system is in the rescan mode, the output voltage from the digital to analog convertor, representative of the point at which a cell was found, remains constant.

The beginning of the rescan mode requires that the beam be moved back only to the leading edge of the point at which capture is made so that the focus scans are over the point at which the pattern capture was made. In order to prevent the signal on the RBU line from initiating a seven micron backup, the $\overline{FOCUS}$ signal provides a disabling input to AND gate 472 until the focus cycle is complete. At the completion of the focus cycle, the focus signal goes high thereby enabling AND gate 472 and the beam is thus caused to be moved back approximately seven microns. This is accomplished by the output voltage from AND gate 472 which goes to ground and thereby causes a lowering of the voltage to the driver 476 when the gate is enabled. A classification scan is then caused to start from that point seven microns to the left of the position stored by the slow scan counter 202 by the application of a positive voltage on output line RS of the rescan sweep flip flop 208 to ramp generator 474. The voltage applied from the ramp generator via summing resistor 486 and ultimately to the driver 476 causes a movement of the beam in the slow scan direction 20 microns along the field in the blood smear during the period that 80 fast scan lines are completed. As soon as 80 scan lines are complete during the count of 4 to 84 in the rescan counter, the rescan sweep flip flop 208 in FIG. 13 is reset thereby causing the voltage at the input of the ramp generator 474 to be relinquished and thereby enabling voltage at the output of the ramp generator to go towards ground.

Also, when the rescan counter reaches the count of 84, the positive voltage is again applied to the RBU line thereby disabling AND gate 472 which causes the output voltage thereof to go high and thereby returning the bias via resistor 484 to the operational amplifier 480 and via summing resistor 488 which enables the beam to return to its original position in the slow scan direction so that a search mode can be resumed at the fast scan line in which a pattern capture of a white blood cell was obtained before the rescan.

RECYCLE AND BLANKING CONTROL

Figure 20:
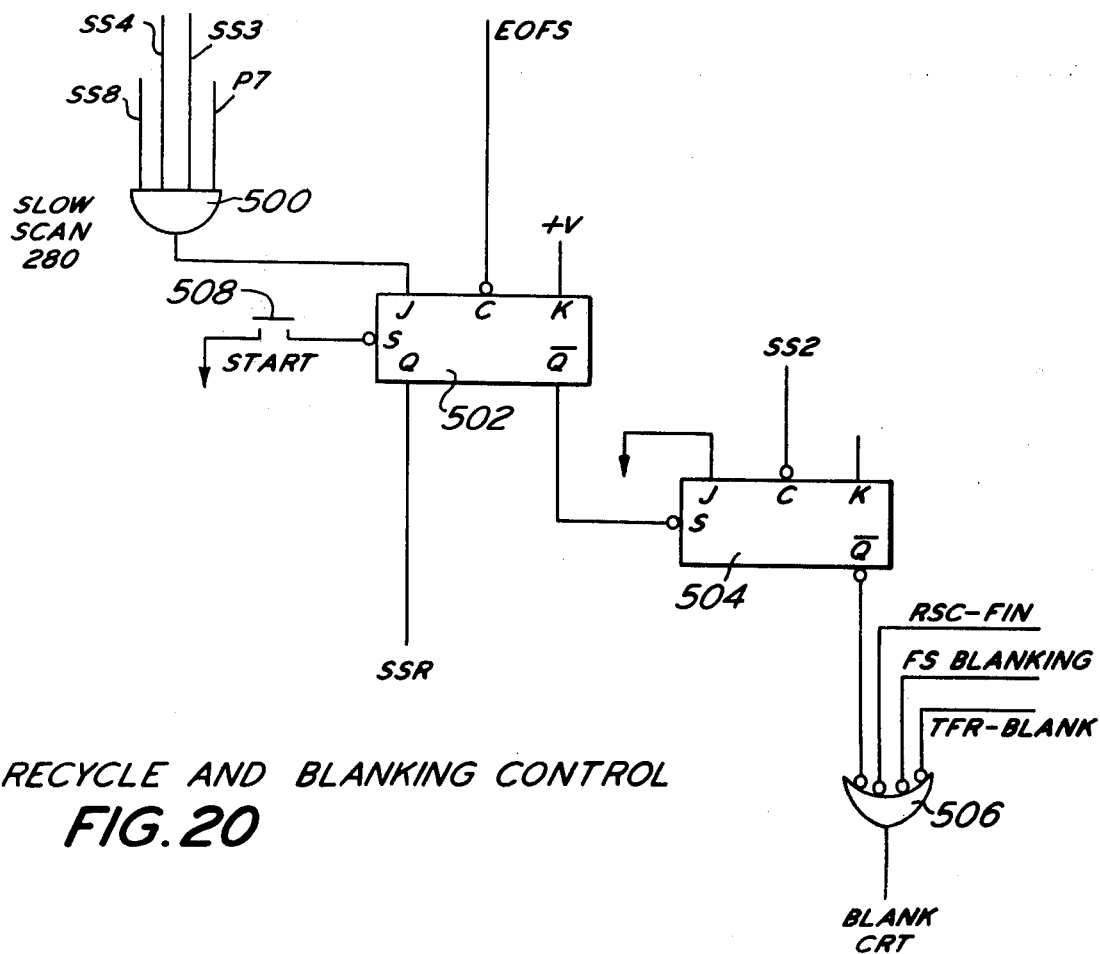
FIG. 20 is a schematic block diagram of the recylce and blanking control circuitry.

The recycle and blanking control circuitry is shown in FIG. 20. This circuitry includes an AND gate 500, a flip flop 502, a flip flop 504 and an OR gate 506. The flip flop 502, in combination with flip flop 504 and AND gate 500, acts to recycle the slow scan counter 202 in FIG. 13. The input line to AND gates 500 are connected to the output lines SS3, SS4 and SS8 of the slow scan counter 202. The fourth input line to AND gate 500 is the output line P7 of the basic timing decoder. The output of AND gate 500 is connected to the J input of flip flop 502. The flip flop 502, in addition to receiving the signal from the AND gate 500 on the J input is connected to and receives the EOFS signal from the output of the $\overline{Q}$ line of flip flop 200 in the fast scan timing circuitry of FIG. 12.

The K input of flip flop 502 is connected to $+V$, the Q output of flip flop 502 is connected to the SSR output line which is connected to the reset of the slow scan counter 202 and the $\overline{Q}$ output line is connected to the S input of flip flop 504. Flip flop 504 has its J input line connected to ground, the C input line is connected to line SS2 which is the third stage output line of the slow scan counter. The $\overline{Q}$ output line of the flip flop 504 is connected to OR gate 506. The OR gate 506 is also connected to the RSC-FIN output line which is connected to the output of gate 234 in FIG. 13, the FS blanking line which is connected to the output of OR gate 452 of the fast scan control circuitry in FIG. 18 and the TFR-BLANK line which is connected to the $\overline{Q}$ output line of the compute flip flop 212 in FIG. 13.

AND gate 500 is enabled when the count of 280 is reached in the slow scan counter. When the AND gate 500 is enabled, it causes the flip flop 502 to be set at the end of the 280 fast scan line. When the flip flop 502 is set it causes flip flop 504 to be reset as the $\overline{Q}$ goes low. When the Q output line goes high it resets the slow scan counter 202 to zero. The setting of the flip flop 502 causes the setting of flip flop 504. The setting of flip flop 504 causes the $\overline{Q}$ output line to go low which thereby enables the OR gate 506. The output of OR gate 506 is connected to the cathode ray tube and a high signal thereon causes a blanking of the cathode ray tube. Thus, the cathode ray tube is blank from the period of time that the slow scan counter reaches the count of 280 until the flip flop 504 is reset. The flip flop 504 is reset when the slow scan counter goes from the count of 7 to 8 thereby causing the SS2 output line thereof to go low. When the output line SS2 goes low, it causes the flip flop 504 to be reset.

It should also be noted that the cathode ray tube is blank whenever any of the RSC-FIN, FS-BLANKING and TFR-BLANK lines go low. These have been explained above. The set input of the flip flop 502 is connected via a manual push-button switch 508 so that the push button is pressed to initiate a scanning. The flip flop 502 is set to cause the slow scan counter to be reset to zero to assure that the complete scan across the slow scan direction is initiated when operation of the system is started. The flip flop 502 remains set as long as the start push button is set and for the period required to complete a fast scan.

AUTOMATIC FOCUS

Figure 21:
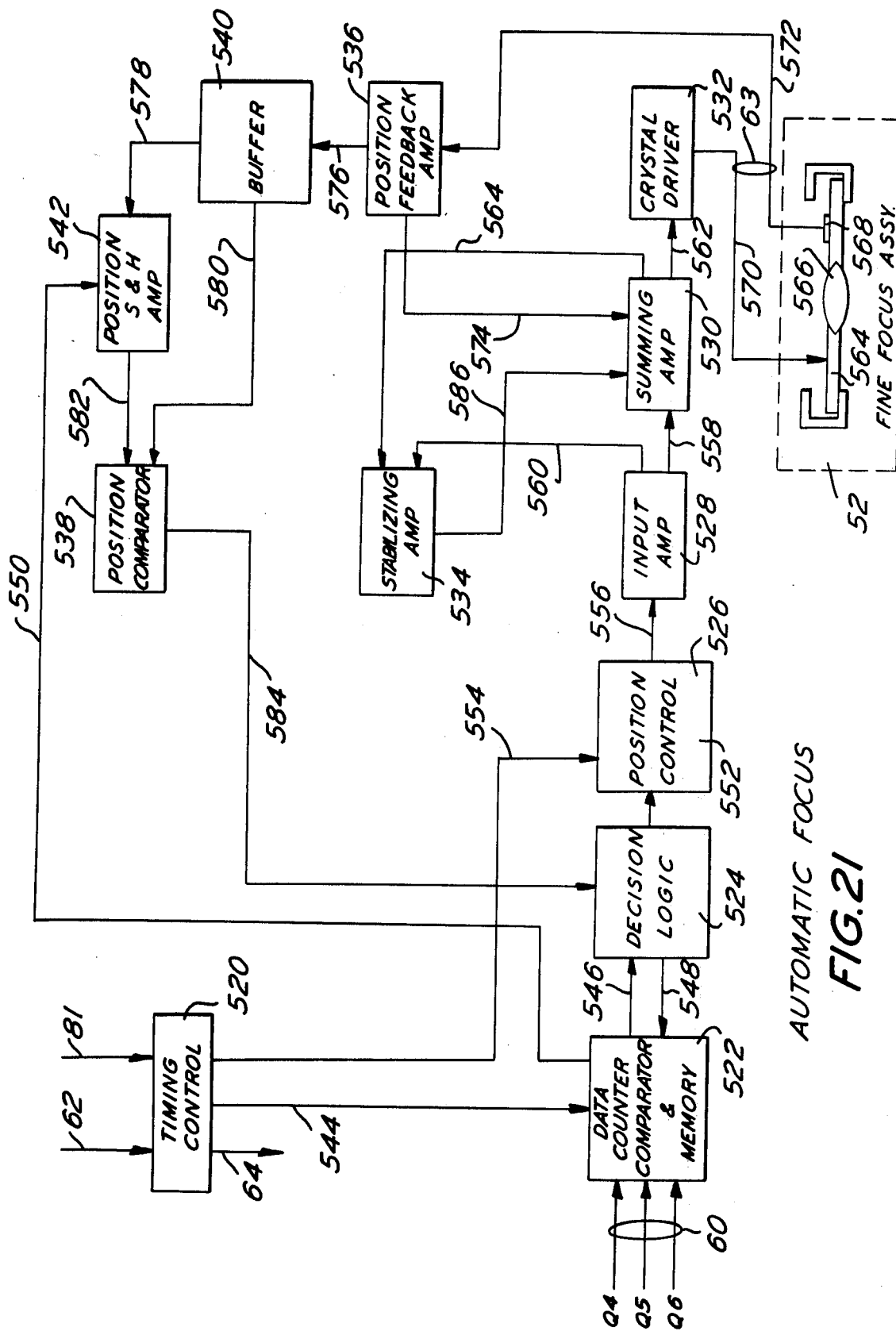
FIG. 21 is a schematic block diagram of the automatic focus circuitry.

The automatic focus system 28 is shown in schematic block diagram in FIG. 21. The automatic focus system includes timing control 520, data counter, comparator and memory 522, decision logic 524 and position control circuitry 526. Units 520, 522, 524 and 526 are the digital portions of the automatic focus system. In addition, the automatic focus system includes analog circuitry which includes input amplifier 528, summing amplifier 530, crystal driver 532, stabilizing amplifier 534, position feedback amplifier 536, position comparator 538, buffer amplifier 540 and position S and H (Sample and Hold) amplifier 542.

The timing control 520 includes inputs from lines 62 and 81. Line 62, as set forth above, is connected to the output of the pattern capture circuitry 36. The capture signal (CS) on line 62 initiates the timing control of the automatic focus system. In addition, the timing control 520 also receives signals on line 81 from the timing and mode control 42 from the fast scan counter as well as the rescan counter. The output signals from the timing control 520 are connected via lines 544 to the data counter, comparator and memory 522. In addition, the data counter comparator and memory 522 also includes signals from quantizers Q4, Q5 and Q6 of the color processor and quantizer 30 which are provided on lines 60. The data counter comparator and memory 522 is connected to decision logic 524 via lines 546 annd 548. The data counter comparator and memory unit 522 is connected to the position S and H amplifier 542 via line 550. The output of decision logic 524 is connected to position control 526 via lines 552. Also connected to the position control is the output of the timing control via lines 554. The output of position control 526 is connected via lines 556 to the input amplifier 528. The output of input amplifiers 528 is connected via line 558 to summing amplifier 530. Input amplifier 528 is also connected to stabilizing amplifier 534 via line 560. The output of the summing amplifier 530 is connected to the input of crystal driver 532 via line 562 and to the stabilizing amplifier via lines 564. The output of crystal driver 532 is connected via lines 63 to the fine focus assembly 52.

As shown schematically in FIG. 21, the fine focus assembly includes a Piezoelectric crystal assembly 564 which supports a lens assembly 566. Secured to the surface of the crystal assembly 564 is a strain gauge 568. As voltage is applied via the crystal driver 532, via lines 570 to the crystal, the crystal 564 bends along its longitudinal axis thereby lifting or lowering the lens assembly 566 in accordance with the amount of voltage applied on lines 570. The amount of bending is sensed by the strain gauge 568 (which, as will hereinafter be seen, is secured both to the top and bottom surfaces of the crystal) which is connected via line 572 to the input of position feedback amplifier 536. The output of position feedback amplifier 536 is connected via line 574 to the summing amplifier 530 and via line 576 to a buffer amplifier 540. The output of the buffer amplifier 540 is connected to the position S and H amplifier 542 via line 578 and to the position comparator via line 580. The output of the position S and H amplifier 542 is connected via line 582 to position comparator 538. The output of position comparator 538 is connected via line 584 to the decision logic 524.

The summing amplifier 530, in addition to receiving signals from the position feedback amplifier, also receives signals via line 586 from the stabilizing amplifier 534.

The operation of the automatic focus system is thus as follows:

The signal provided on line 62 to the timing control 520 is the CS or capture storage signal from the pattern capture circuitry shown in FIG. 16. The timing control 520 includes major and minor timing as will hereinafter be seen. The major timing is comprised of three cycles, the first cycle being for the immediate movement of the fine focus assembly 1 micron from its last position (i.e. the previous optimum focus position). The second cycle of the timing control is the period when weighted quantized data is accumulated in the data counter comparator and memory 552 for determining the position of optimum focus. The third cycle of the timing control is the period when the fine focus assembly is moved to the position of optimum focus. The timing control 520 thus causes, via lines 554, the position control to move the lens assembly 566 of the fine focus assembly one micron from its last position. After the movement to the position has been completed, the second cycle of operation of the timing control causes the data counter, comparator and memory 522 to accumulate or make a data count of weighted quantized data during successive positions as the lens assembly is moved in a reverse direction from that in which lens assembly was initially moved.

Decision logic 524 is responsive to the data counter comparator and memory 522 to determine the new position of optimum focus. After the decision logic determines this position, the third cycle of operation is provided to reverse again the direction of the lens assembly 566 to return the lens to the position of optimum focus. The position control 526 controls the position of the lens assembly. The position of the lens assembly is determined in the position counter and the signal representative of the count therein is transmitted to the input amplifier 528 which provides the input voltage via the summing amplifier to crystal driver 532 to cause the appropriate movement of the Piezoelectric crystal 564. The Piezoelectric crystal assembly 564 is caused to bend in accordance with the amount of voltage provided on lines 570 to the crystal assembly. The bending of the crystal assembly positions the lens assembly 566 and the strain gauges which form a strain bridge 568 are secured to the surface of the crystal assembly and provide a signal indication to the position feedback amplifier via lines 572 indicative of the position of the crystal assembly.

The position feedback amplifier 536 provides the signal of the present invention of the crystal to the position S and H amplifier 542 which samples the voltage from the position feedback amplifier and holds the voltage representative of the optimum focus position until it compares to the representative of the present voltage position of the lens assembly. When the positions are compared upon return to the optimum focus point, the signal from position comparator 538 is changed thereby causing the decision logic 524 to terminate the automatic focusing cycle.

FOCUS TIMING CONTROL

Figure 22:
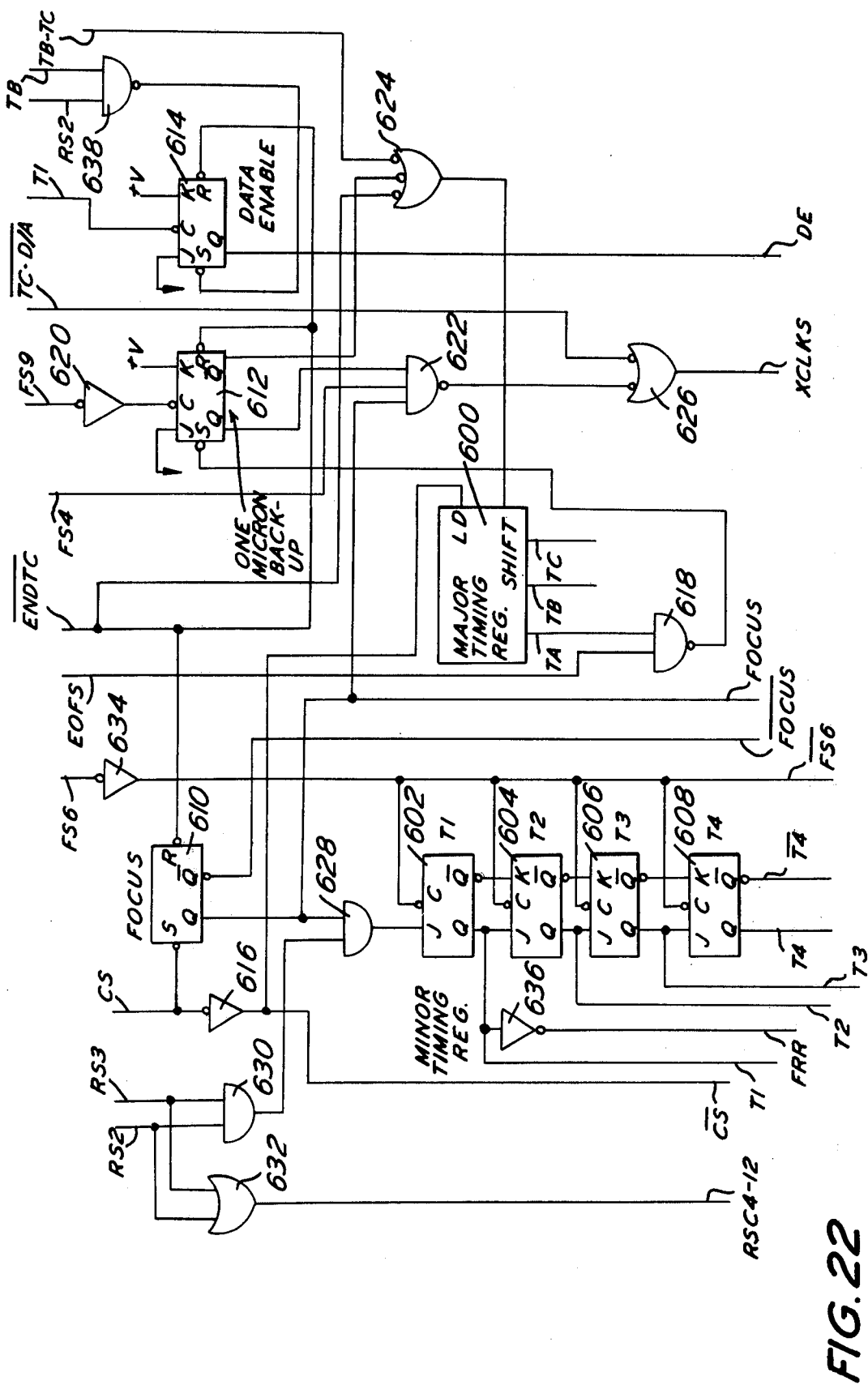
FIG. 22 is a schematic block diagram of the focus timing control circuitry.

The focus timing control is shown in FIG. 22. The focus timing control includes a major timing shift register 600 and a minor timing shift register comprised of flip flops 602, 604, 606 and 608. In addition, the circuitry includes a focus flip flop 610, a 1 micron back-up flip flop 612 and a data enable flip flop 614. The CS line from the $\overline{Q}$ output of the capture flip flop 368 in FIG. 16 is connected to set input of flip flop 610 and to the input of inverter 616. The output of inverter 616 is connected to the $\overline{CS}$ line and to the load input (LD) of shift register 600. The shift register 600 is a three stage shift register having output lines TA, TB and TC. When the input signal to the load input goes high, a one input is provided into the first stage of the shift register. The output line of the first stage of register 600 is TA. Each time a shift pulse is provided on the shift input line, the one moves from left to right. Thus, one pulse moves the one in the TA stage to the TB stage and two pulses move the one in the TA stage of the shift register 600 to the TC stage. The third shift pulse shifts the one out of the shift register 600.

The output of the TA line of the major timing shift register is connected to AND gate 618. The other input to AND gate 618 is the EOFS line from fast scan timing in FIG. 12. The output of AND gate 618 is connected to the set input of the 1 micron back-up flip flop 612. The clock input of flip flop 612 is connected to the output of inverter 620. The input to inverter 620 is the FS9 line which is the output of the $2^9$ line of the fast scan counter of FIG. 12. The J input of flip flop 612 is connected to ground, the K input is connected to +V and the R input of the 1 micron back-up flip flop is connected to the END TC line. The Q output line is connected to an input of AND gate 622 and the $\overline{Q}$ output is connected to an input of OR gate 624. A second input to AND gate 622 is connected to the FS4 line which is the output of the $2^4$ stage of the fast scan counter in FIG. 12. The third input line to AND gate 622 is the FOCUS line which is connected to the Q output of focus flip flop 610. The output of AND gate 622 is connected to one of the inputs of OR gate 626.

OR gate 624 has a second input connected to the END TC line and a third input is connected to the TB-TC line. The output of OR gate 624 is connected to the shift input of the major timing shift register 600. The output of OR gate 626 is connected to the XCLKS output line which, as will hereinafter be seen, is utitlized to move the lens assembly of the fine focus assembly.

The Q output of the focus flip flop 610 is connected also to an input of AND gate 628. The $\overline{Q}$ output line of the focus flip flop 610 is connected to the $\overline{FOCUS}$ line. The reset line of the focus flip flop 610 is connected to the $\overline{END\ TC}$ line. The remaining input to the AND gate 628 is the output of AND gate 630. The output of AND gate 628 is connected to the J input of flip flop 602 of the minor timing register. The inputs to AND gate 630 are the RS2 and RS3 lines from the $2^2$ and $2^3$ output lines of the rescan counter 204 in FIG. 13. The RS2 and RS3 lines are also connected to the inputs of an OR gate 632. The output of the OR gate 632 is the RSC4-12 line which indicates that the line is enabled during the rescan counts of 4 through 12. The output of AND gate 630 is enabled on the count of 12 in the rescan counter 204.

The flip flops 602, 604, 606 and 608 are connected in cascade as a shift register. That is, the Q output of flip flop 602 is connected to the J input of flip flop 604, the Q output of flip flop 604 is connected to the J input of flip flop 606 and the Q output of flip flop 606 is connected to the J input of flip flop 608. Similarly, the $\overline{Q}$ output of flip flop 602 is connected to the K input of flip flop 604, the $\overline{Q}$ output of flip flop 604 is connected to the K input of flip flop 606 and the $\overline{Q}$ output of flip flop 606 is connected to the K input of flip flop 608. The clock (C) input line of each of the flip flops 602, 604, 606 and 608 is connected to the output of inverter 634, the input of which is connected to the FS6 line of the fast scan counter. The output of the inverter is also connected to the $\overline{FS6}$ line.

The flip flops 602, 604, 606 and 608 are respectively referred to as T1, T2, T3 and T4 flip flops of the minor timing register. The Q output of flip flop 602 is connected to the T1 line as well as the inverter 636, the output of which is the FRR line which resets the rescan counter 204 in FIG. 13. The Q output of flip flop 604 is the T2 line, the Q output of flip flop 606 is connected to the T3 line, the $\overline{Q}$ output of flip flop 608 is connected to the $\overline{T4}$ line.

The data enable flip flop 614 has its Q output connected to the DE line, its set input connected to the output of AND gate 638, its reset input connected to the END TC line, its J input to ground and its K input to +V. The clock input of the data enable flip flop 614 is connected to the T1 line from flip flop 602 of the minor timing register. The AND gate 638 has its inputs connected to the RS2 line from the rescan counter 204 and the TB line from the output of the major timing register 600. Finally, the OR gate 626 has its second input connected to the $\overline{TC\ D/A}$ line.

In operation, the focus timing control is initiated by a low signal on the CS line from the pattern capture circuitry. That is, as soon as capture of a white cell is made, the focus flip flop 610 is set. In addition, a one is loaded into the first stage of major timing register 600 thereby causing the TA output line to go high. As soon as the first EOFS signal which is generated at the end of a fast scan is received after capture has been made, AND gate 618 is enabled which thereby causes the setting of the 1 micron back-up flip flop 612. The one micron back-up flip flop remains set until the $2^9$ stage of the fast scan count goes high which thereby causes a low signal to the clock input of the 1 micron back-up flip flop 612 and thereby causes the flip flop to be reset as a result of the +V signal on the K input thereof.

The AND gate 622 is thus enabled by the one micron back-up flip flop and the focus flip flop to pass 16 pulses from the FS4 line of the fast scan counter to OR gate 626. This results in the backing up of the lens assembly 1 micron from the position of the lens assembly at which the white cell was captured. Each pulse passed by AND gate 622 to OR gate 626 enables the lens assembly to be moved 1/16 micron by the crystal assembly 564. The 1 micron back-up flip flop 612 remains on long enough to enable the AND gate 622 to pass 16 FS4 pulses from the fast scan counter. After the 16th pulse has been passed by the AND gate 622, the $2^9$ stage of the fast scan counter goes high thereby causing the flip flop 612 to be reset.

When the one micron back-up flip flop 612 is reset, the OR gate 624 is enabled by the Q output line of flip flop 612 and thereby provides a pulse to the shift input of the data timing register 600 thereby causing the one in the first stage to be shifted to the second stage and thereby enabling the TB line of the register 600.

As will be remembered, upon receipt of the capture storage signal, the rescan counter is initiated and starts counting each fast scan sweep on the EOFS signal generated by the fast scan counter. When the rescan counter reaches a count of four, AND gate 638 is enabled. That is, since the major timing register 600 has the one in the second stage and TB is enabled, the AND gate 638 is enabled when the rescan counter is at a count of four. The enabling of gate 638 causes the data enable flip flop 614 to be set.

The high signal on the data enable line, as will hereinafter be seen, enables the quantization data count for each of the plurality of dispositions of the lens assembly 566. That is, the lens is moved through a series of positions and the quantization count is made until the optimum position is determined. During the TB cycle, the rescan counter is enabled to count to 12 a number of times. During the counts of 4 through 12 which correspond to the eight fast scan lines in the focus cycle, the quantization data is accumulated in the counter of the data counter, comparator and memory 522. After the eighth line has been completed, both RS2 and RS3 go high and the AND gate 630 is thereby enabled thereby causing the enabling of AND gate 628. The enabling of AND gate 628 primes the flip flop 602 to be set upon the next high pulse from the FS6 line of the fast scan counter.

The setting of the T1 flip flop enables the output line T1 to go high and the FRR output line to go low. The FRR line causes a resetting of the rescan back-up flip flop 206 and the rescan sweep flip flop 208 which in turn causes the resetting of the rescan counter 204 to zero.

The flip flop 602 is set for approximately 85 microseconds at which time the next pulse is provided on the FS6 line to shift the one from the flip flop 602 to flip flop 604. Upon the fall of the T1 signal, the data enable flip flop 614 is reset as a result of the +V voltage connected to the K input thereof. During the time that the T1 signal is high, the count in the data counter of the data counter, comparator and memory is compared to the count in the data register in FIG. 23. During the time that T2 goes high, the data register is updated with the count that was just made in the data counter. Again, the T2 signal lasts approximately 85 microseconds and then the next high pulse on line FS6 causes a shifting of the one from flip flop 604 to flip flop 606 thereby setting flip flop 606 and causing the T3 signal to go high.

The T3 time is dedicated to decision making in the decision logic 524 to determine whether optimum focus has been reached. After a single dat count has been made, it is not possible to determine whether optimum focus has been reached and therefore data counts continue.

During the time that the one in the minor timing register is shifted into the T4 flip flop 608, the signals on line T4 and $\overline{T4}$ are used by the decision logic to determine whether the data counting portion or the TB cycle of the major timing has been completed and for clearing the data counter in the data counter, comparator and memory unit 522.

The next quantized data accumulation then takes place on the count of four in the rescan counter. When the rescan counter reaches the count of four AND gate 638 is enabled thereby setting the data enable flip flop 614. When the data enable flip flop is set, the accumulation of quantized data is made during the counts 4 through 11 in the rescan counter. At the count of 12 in the rescan counter the AND gate 630 is enabled which thereby places a one in the first stage of the minor timing register. The minor timing cycle of T1 through T4 is then repeated. The rescan counter is again reset to zero, the data enable flip flop 614 is reset and is not set again until the rescan counter reaches the count of four.

It can therefore be seen that during the TB time of the major timing register the rescan counter enables a plurality of mini scans during each of which a quantized data accumulation is made. After each eight line focus scan is completed, the count of 12 in the rescan counter initiates the minor timing cycle of T1 through T4 during which the rescan counter is reset, the counts in the data counter and data register are compared, the decision logic is checked and a decision as to whether an optimum focus has been achieved is also made. After the last required focus scan is made, and the minor timing cycle thereafter is completed, a signal is provided on line TB-TC to indicate that TB has been completed which causes a shift pulse in shift register 600 which shifts the one from the TB stage to the TC stage. The lens assembly 566 is moved back to the position where optimum focus was found. When the lens assembly 566 is moved to the optimum position for optimum focus, the $\overline{\text{END TC}}$ line goes low thereby causing OR gate 624 to be enabled and thereby shifting the one out of the TC stage of the major timing register 600. Also, the focus flip flop 610, the 1 micron backup flip flop 612 and the data enable flip flop 614 are reset thereby ending the focusing cycle and causing a continuation of the rescan for classification purposes in the pattern recognition system.

FOCUS DATA COUNTER, COMPARATOR AND MEMORY

Figure 23:
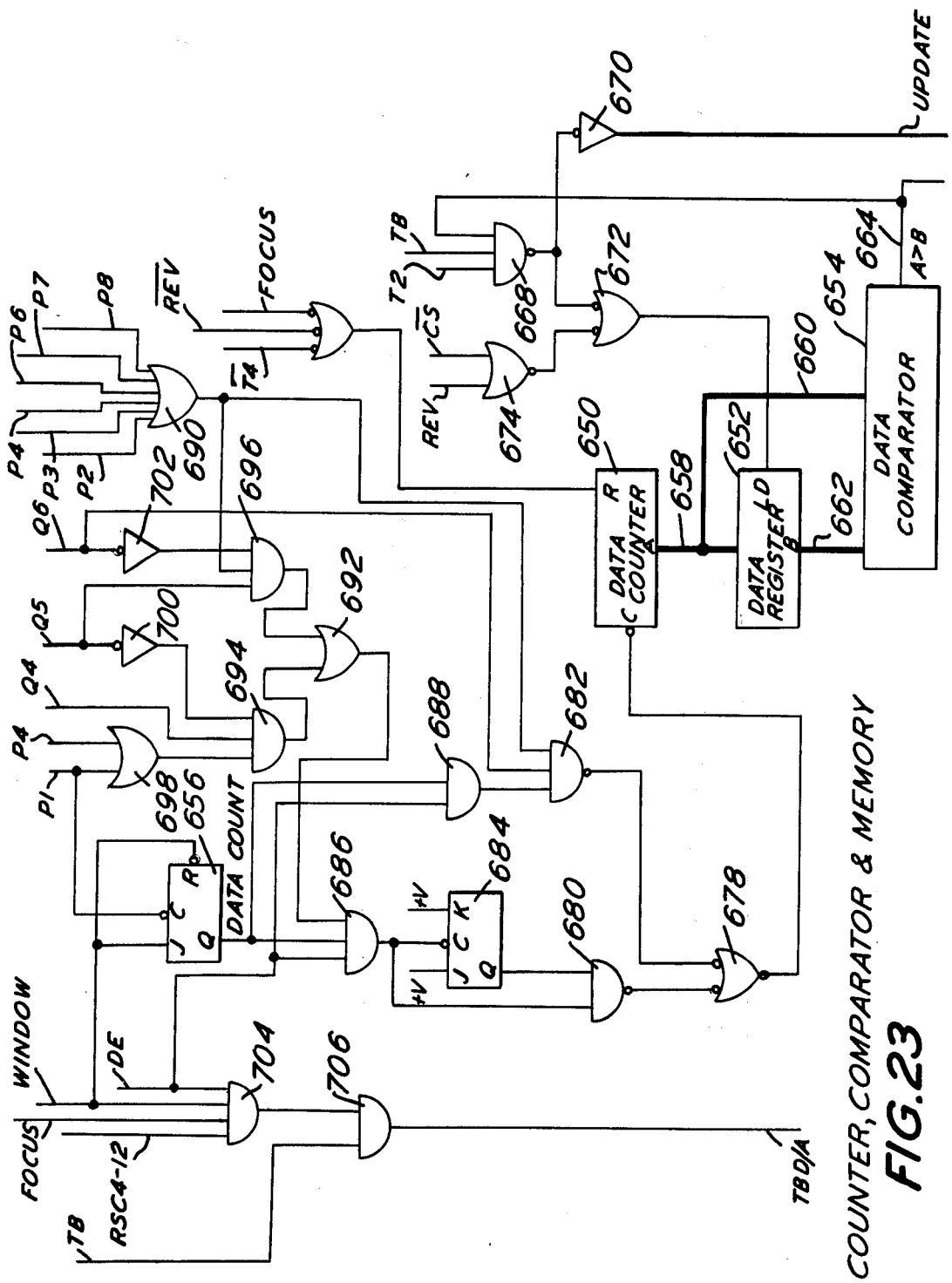
FIG. 23 is a schematic block diagram of the data counter comparator and memory circuitry.

The data counter, comparator and memory is shown in FIG. 23. The data counter, comparator and memory circuitry includes a data counter 650, a data register 652, a data comparator 654, data count flip flop 656 and associated gates, inverters and flip flops.

The data counter 650 basically comprises a conventional 12 bit binary counter. The stages of the data counter 650 are connected in parallel via lines 658 to the inputs to each of the stages of the data register 652. The data register 652 is basically a 12 stage data register for storing the counts of the data counter when a high signal is provided on the load input (LD) of the data register 652.

The output of the data counter 650 is also connected in parallel to data comparator 654 via lines 660. Similarly, the outputs of each of the stages of data register 652 are connected via output line 652 in parallel to the data comparator 654. For ease of reference, the counts or contents of the data counter 650 is hereinafter referred to as A. The contents of the data register 652 is hereinafter referred to as B.

The data comparator 654 is a conventional binary comparator which provides a high signal on output line 654 when A is larger than B. When B is equal to or smaller than A, the output signal on line 664 is low. The output line 664 of the data comparator is connected to a first input of AND gate 668. The remaining inputs of the AND gate 668 are connected to the TB and T2 output lines from the focus timing control. The output of AND gate 668 is connected to an inverter 670 and to one input of OR gate 672. The output of inverter 670 is the UPDATE line. The remaining input of OR gate 672 is connected to the output of OR gate 674. The output of the OR gate 672 is connected to the load input of data register 652. The inputs to OR gate 674 are the REV input and the $\overline{CS}$ input. The reset input to the data counter 650 is connected to the output of OR gate 676. The inputs to OR gate 676 are the $\overline{T4}$, $\overline{REV}$ and FOCUS lines. The clock input of data counter 650 is connected to the output of OR gate 678. The inputs to OR gate 678 are connected from the outputs of AND gate 680 and 682. The inputs to AND gate 680 are connected from the Q output of flip flop 684 and the output of AND gate 686. The output of AND gate 686 is connected to the clock input of flip flop 684 as well as to the input of AND gate 680. The J and K inputs of flip flop 680 are connected to +V.

The inputs to AND gate 682 are connected to the output of AND gate 688, the Q6 line and the output of OR gate 690. The inputs to AND gate 688 are the DE line and the Q output line of data count flip flop 656. The inputs to AND gate 686, in addition to the DE input line, also include the Q output line from data count flip flop 656 and the output of OR gate 692. The data count flip flop 656 has its clock input connected to the P1 line from decoder 184 in FIG. 11, its reset and J input to the window line from the window control in FIG. 17. The input lines to OR gate 690 are connected to the P2, P3, P4, P6, P7 and P8 lines of the docoder 184 in FIG. 11.

The inputs to OR gate 692 are connected from the outputs of AND gates 694 and 696. The inputs to AND gate 694 are connected to the output of AND gate 698, the Q4 line and the output of inverter 700. The input of inverter 700 is connected to the Q5 line. The inputs to AND gate 696 are connected to the Q5 line and the output of inverter 702. The DE and WINDOW line are also connected to the inputs of AND gate 704. In addition, the focus line and the RSC4-12 line are also connected to the input of AND gate 704. The output of AND gate 704 is connected to AND gate 706. The other input of AND gate 706 is connected to the TB line. The output of AND gate 706 is connected to the TBD/A line.

The operation of the data counter, comparator and memory circuitry is during the rescan lines 4 through 11. AND gate 704 is enabled by the RSC4-12 line, the focus line and the data enable line of the data enable flip flop 614 in FIG. 22 going high. The AND gate 704 is thus enabled during the window and provides a pulse during each fast scan line. The AND gate 706 is thus enabled eight times during the TB time for each focus scan to provide eight pulses to the position control for moving the lens assembly a half micron during the period that the quantization data is accumulated. Each pulse provided from the AND gate 706 to the position control effectively moves the objective lens 1/16 micron. Accordingly, eight pulses cause movement of the lens assembly a half micron.

It should be noted that although the RSC4-12 line is enabled during counts four through twelve of the rescan counter, the period of time that the rescan count is 12 is only a small portion of a fast scan line. That is, as soon as the count reaches twelve in the rescan counter, the AND gate 630 in the focus timing control in FIG. 22 enables the flip flop T1 to be set upon the first pulse on the FS6 line. Accordingly, as soon as T1 is set, the rescan counter is reset thereby providing a count of zero in the rescan counter. This disables the AND gate 704 and thus prevents the ninth pulse from the AND gate 706.

The data count flip flop 656 is set at the beginning of a window and is reset at the end of the window by the window line from the window control. AND gate 686 is thus enabled by the DE line which causes AND gate 686 to be enabled during the rescan lines four to eleven along with the flip flop 656 to pass quantization data pulses from the network of gates including OR gates 690, 692 and 698, AND gates 694 and 696 and inverters 700 and 702. The OR gate 690 provides six pulses during each fast scan count. That is, the six pulses from the decoder provided on lines P2, P3, P4, P6, P7 and P8 during each fast scan count enable OR gate 690 thereby providing six short pulses during each fast scan count to AND gate 696 and to AND gate 682.

The AND gate 688 is also enabled by the flip flop 656 and the DE line which means that AND gate 688 is enabled for eight lines during the rescan counts from 4 to 11.

Gate 682, which is also connected to the output of the OR gate 690, is additionally connected to the output of the quantizer Q6.

The data count and data enable flip flop act to gate the quantization data to the data counter 650. The gates are so connected that, whenever a quantization level of Q6 is present, six pulses are gated to the data counter 650. When a quantization level of Q5 is reached, three pulses are gated to the data counter 650 and when a quantization level of Q4 is reached, one pulse is gated to the data counter 650. It should be remembered that, whenever Q6 is high, both Q5 and Q4 are high. Thus, gate 696 is enabled when Q5 is high, but level Q6 has not been reached. Similarly, gate 694 is enabled only when Q4 is present but Q5 is not present.

The AND gate 682 is enabled when the Q6 level is reached and for each count of the fast scan counter that Q6 is present, six pulses are passed from the output of OR gate 690 through AND gate 682 which is enabled by Q6 during the window between rescan counts four through eleven. OR gate 678 thus passes six pulses to the data counter each time that Q6 is present during a fast scan count in the window.

When Q5 is present and level Q6 is not reached, AND gate 696 is enabled to pass six pulses from OR gate 690 for each fast scan count that Q5 is reached. When level Q4 is reached and Q5 has not been reached, AND gate 694 is enabled to pass two pulses during each fast scan count from OR gate 698 which is pulsed twice during each fast scan count, thereby passing two pulses to OR gate 692 which are passed to AND gate 686. Since only three pulses are required for a Q5 level and one pulse for a Q4 level, the flip flop 684 acts as a divided by two counter in combination with AND gates 686 and 680. That is, AND gate 686 passes six pulses for each fast scan count that Q5 is present and two fast scan pulses for each fast scan count in which Q4 is present.

This means that the AND gate 686 is passing twice as many pulses as are desired. Therefor, each time that flip flop 684 receives a pulse from AND gate 686, flip flop 684 is switched in state. That is, both the J and K inputs of flip flop 684 are connected to +V, thereby enabling the flip flop to change state each time a negative going pulse is provided at the clock input thereof. Thus, AND gate 680 is enabled by the flip flop 684 once for each two pulses provided by AND gate 686 to the clock input of flip flop 684.

Thus, AND gate 680 passes one half of the pulses to the OR gate 678 which are then passed to the data counter 650. Accordingly, the data counter 650 receives six pulses for each fast scan count in which the quantization level of Q6 has been reached, three pulses for each time the quantization level of Q5 has been reached and one pulse for each time that the quantization level Q4 has been reached.

During the first focus scan, the data counter 650 receives the weighted quantization data count. Because the data register 652 is cleared prior to the start of the focus cycle, during time T1, after the first weighted quantization count is made, A is larger than B. During time T2, data register 652 has the count in the counter 650 provided in parallel via line 658 as the AND gate 668 is enabled thereby providing an enabling pulse to the load input of the data register 652. The data register continues to be updated after each focus scan as long as A is larger than B. That is, the data count, as it continues to rise, is placed in the data register 652. The count in data register 652 is not updated as soon as it remains larger than the count put in data counter 650. That is, as soon as the B count stored in register 652 is larger that count A, line 664 goes low thereby disabling AND gate 668 and preventing the T2 pulse from updating the data register 652 by loading it with the newest count. Thus, the A total is constantly compared against the highest data count reached until the decision logic determines where the optimum focus is located.

When the decision logic determines that the lens assembly has been moved in the wrong direction and the direction must be reversed in order to obtain optimum focus, the last count in the data counter 650 is loaded into the data register by the enabling of the OR gate 674 by the REV signal being generated in the decision logic. During the T4 time after the data register 652 has been loaded, the data counter 650 is reset by the enabling of OR gate 676. The focus scans continue until the decision logic has determined whether the optimum focus has been passed.

FOCUS DECISION LOGIC

Figure 24:
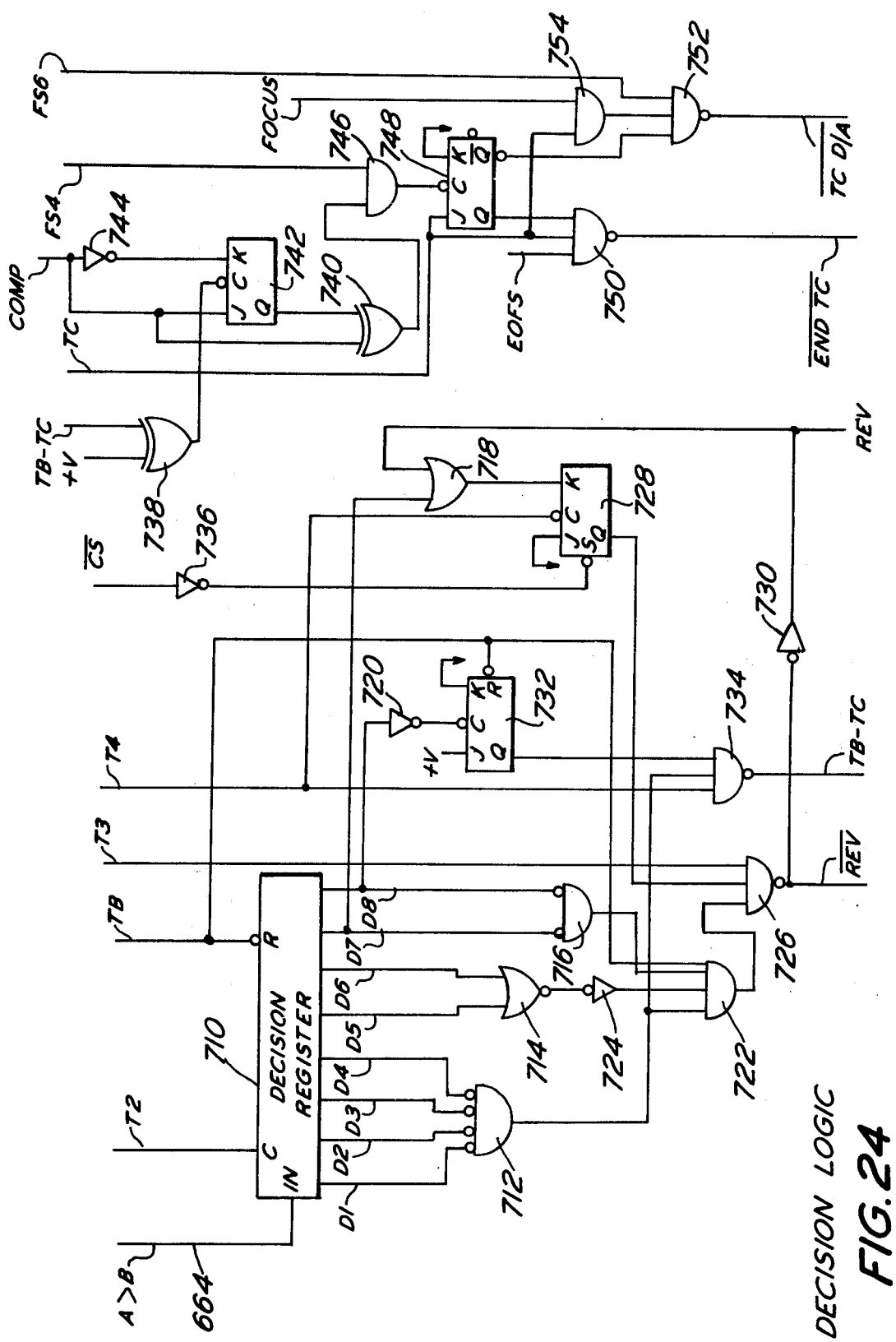
FIG. 24 is a schematic block diagram of the decision logic circuitry.

The decision logic is shown in FIG. 24 and includes a decision register 710 and associated gating and flip flops. The decision register 710 basically comprises an eight bit shift register. The input to the decision register is provided from the A>B line 664. The decision register is shifted by signals provided on the T2 line to the clock input. The reset of the decision register which clears the decision register is connected to the TB line which goes low at the end of the TB cycle and resets the register.

The decision register includes eight output lines D1 through D8, which represent the first through eighth stages of the decision register, respectively. The eight stages are hereinafter referred to as D1 through D8, respectively.

The output lines D1 through D4 of the decision register 710 are connected to the four inputs of AND gate 712. The D5 and D6 outputs of the decision register are connected to the inputs of OR gate 714 and the D7 and D8 output lines of the decision register 710 are connected to the inputs of OR gate 716. Output line D7 is also connected to an input of OR gate 718 and the output line D8 is also connected to the input of an inverter 720.

The output of AND gate 712 is connected to an input of AND gate 722 and an input of AND gate 734. The output of OR gate 714 is connected to another input of AND gate 722 via an inverter 724. The output of AND gate 716 is connected to a third input of AND gate 722. The fourth input of AND gate 722 is connected to the TB line. The output of AND gate 722 is connected to an input of AND gate 726, a second input to AND gate 726 is connected from the Q output line of flip flop 728 and the third input of AND gate 726 is connected to the T3 line. The output of AND gate 726 is connected to the REV line and to the input of inverter 730 which is in turn connected to the REV line and to an input of OR gate 718. The output of inverter 720 is connected to the clock input of flip flop 732. The J input of flip flop 732 is connected to +V, the K input is connected to ground and the Q input is connected to an input of AND gate 734. The remaining inputs to AND gate 734 are connected to the outputs of AND gate 712 and to line T4. The output of AND gate 734 is connected to the TB-TC line.

The reset input of flip flop 732 is also connected to the TB line. The output of OR gate 718 is connected to the K input of flip flop 728. The clock input of flip flop 728 is connected to the T4 line, the set input of flip flop 728 is connected to the output of inverter 736. As previously set forth, the Q output of flip flop 728 is connected to the second input of AND gate 726.

The inverter 736 has connected to its input, the $\overline{CS}$ line. This line goes high whenever the capture of a white cell is made and it stays high until the first EOFS signal at the end of the first fast scan line in which the capture is made.

The decision logic also includes an EXCLUSIVE OR gate 738 and an EXCLUSIVE OR gate 740. EXCLUSIVE OR gate 738 has one input connected to +V and the remaining input connected to the TB-TC line. The output of EXCLUSIVE OR gate 738 is connected to the clock input of flip flop 742. Gate 738, as a result of the +V connected to one input, acts as an inverter.

The J input of flip flop 742 is connected to the COMP line, the K input is connected to the output of the inverter 744 and the Q output is connected to an input of EXCLUSIVE OR gate 740. The COMP line is also connected to an input of EXCLUSIVE OR gate 740. The input to inverter 744 is the COMP line which is the output of the position comparator. The output of EXCLUSIVE OR gate 740 is connected to an input of AND gate 746. The second input of AND gae 746 is the FS4 line. The output of AND gate 746 is connected to the clock input of flip flop 748. The J input of flip flop 748 is connected to the TC line, the K input is connected to ground, the Q output line is connected to an input of AND gate 750 and the $\overline{Q}$ output line is connected to an input of AND gate 752.

A second input to AND gate 750 is the TC line and the third input of AND gate 750 is the EOFS line. The output of AND gate 750 is connected to the $\overline{\text{END TC}}$ line. In addition to being connected at its input to the $\overline{Q}$ output of flip flop 748, AND gate 750 is also connected to the output of AND gate 754 and to the FS6 line from the fast scan counter. The output of AND gate 752 is connected to the $\overline{\text{TCD/A}}$ line. The inputs to AND gate 754 are the TC line and the focus line.

The decision register 710, in combination with the associated gating circuitry, enables the determination of whether and when the optimum focus has been achieved when three ones are inserted into the decision register followed by four zeros. This means, effectively, that in the direction that the lens assembly is moved during TB time, the lens is initially out of focus and is moved to the optimum focus and then passes optimum focus by 2 microns. If less than three ones preceeds the four zeros, it is necessary that the direction of movement of the lens assembly be reversed and optimum focus be passed in the opposite direction in order to achieve the best or optimum focus.

Thus, in operation, if less than three ones are placed into the decision register, followed by the four zeros, the logic determines that a reversal is required. For example, if a single one is generated on the A>B line 664 followed by four zeros, then, when the first one reaches the fifth stage, D5 is high and D1, D2, D3 and D4 are low thereby causing the enabling of both OR gate 714 and AND gate 712. Since D7 and D8 are both zero, the output lines therefrom are low thereby causing the enabling of AND gate 716. Thus, since the data accumulation is done during the TB time, TB is also high and thereby causes the enabling of AND gate 722.

The enabling of AND gate 722 causes the AND gate 726 to be enabled during T3 time since flip flop 728 has been initially set by the receipt of the capture pulse. When AND gate 726 is enabled, it causes a reversal of the direction of the lens assembly.

If two ones are followed by four zeros after six focus scans, gate 714 is enabled by the two ones in position D5 and D6 and the four zeros in D1 through D4 enable AND gate 712. Since two zeros remain in positions D7 and D8 of the decision register 710, AND gate 716 is also enabled and thereby enables the AND gate 722 and then 726 during the T3 time. However, if, as often happens, at least three ones are provided in the decision register followed by four or more zeros, then the three ones are shifted to D5, D6 and D7 positions of the decision register 710 at the end of the seventh focus scan in that direction and the four zeros are then located in the D1 through D4 positions of the decision register.

It should be noted that because at least three ones are provided to the decision register, when the first one reaches the D6 position the third one is in the D4 position and thereby prevents the enabling of AND gate 712. As long as three ones are provided to the decision register by the output of the data comparator 654 in FIG. 23, the ones ultimately reach the seventh stage of the decision register and thereby cause the resetting of flip flop 728 via OR gate 718 which provides a high signal to the K input thereof and the flip flop is then reset at the end of the minor timing cycle by the T4 input to the clock input of flip flop 728. As soon as the flip flop 728 is reset, it prevents reversal of movement of the lens assembly to find optimum focus by lowering the output signal on the Q output line to AND gate 726.

When the next scan is completed and the one in the seventh stage of the decision register is shifted into the eighth stage, the high signal on the D8 line causes the flip flop 732 to be set and thereby causes the AND gate 734 to be conditioned for being enabled during the T4 time of the minor timing cycle. When AND gate 734 is enabled it indicates the end of the TB portion of the major timing cycle and a change into the TC portion of the cycle wherein the direction of the lens is reversed, but only for the purpose of returning to the point at which optimum focus was achieved. When TB-TC goes high, the EXCLUSIVE OR gate 738 is disabled thereby causing a low signal to the clock input of flip flop 742.

The changing of state of flip flop 742 causes the EXCLUSIVE OR gate to be disabled because the output from the Q output line 742 is made the same as the signal on the COMP line from position comparator 538. That is, whatever the signal is on the COMP line, the inverted signal thereof is applied to the K input of flip flop 742. Therefore, if the signal on the COMP line is high, the Q output of flip flop 742 goes high because the flip flop is set. If the COMP line has a low signal thereon, the flip flop is changed to or stays in the reset state. The Q output is then low. Thus, whatever the state of flip flop 742, after it receives the trigger pulse from the generator of the TB-TC pulse, the Q output line of flip flop 742 matches the remaining input to the EXCLUSIVE OR gate 740 and thereby disables the same.

When the TB-TC line becomes high, it also causes TC to go high, thereby causing flip flop 748 to have a positive voltage applied to the J input thereof. When the signal on the COMP line changes, it indicates that the objective lens has been moved back to the position of optimum focus which has been determined previously and which has been stored in the position S and H amplifier 542. The enabling of the EXCLUSIVE OR gate 740 provides an enabling signal to AND gate 746 so that the next pulse on the FS4 line causes the flip flop 748 to be set. When the FS4 pulse arrives and flip flop 748 is set, the AND gate 750 is primed to be enabled at the end of the fast scan by the high signal on the EOFS line. As the signal goes high on the EOFS line AND gate 750 is enabled and thereby generates the end of the TC portion of the major timing cycle by causing the $\overline{\text{ENDTC}}$ line to go low which acts to end the focus cycle.

Prior to the flip flop 748 being set, AND gate 752 is enabled by the $\overline{Q}$ output line of flip flop 748, the output of AND gate 754 which is enabled during the TC portion of the focus cycle and by each pulse on the FS6 line. These pulses on the FS6 line cause AND gate 756 to generate negative going output pulses on line $\overline{\text{TCD/A}}$ which are provided to the digital to analog converter in the position control which causes the position of the lens assembly to be moved 1/16 micron for each pulse generated on line $\overline{\text{TCD/A}}$.

POSITION CONTROL

Figure 25:
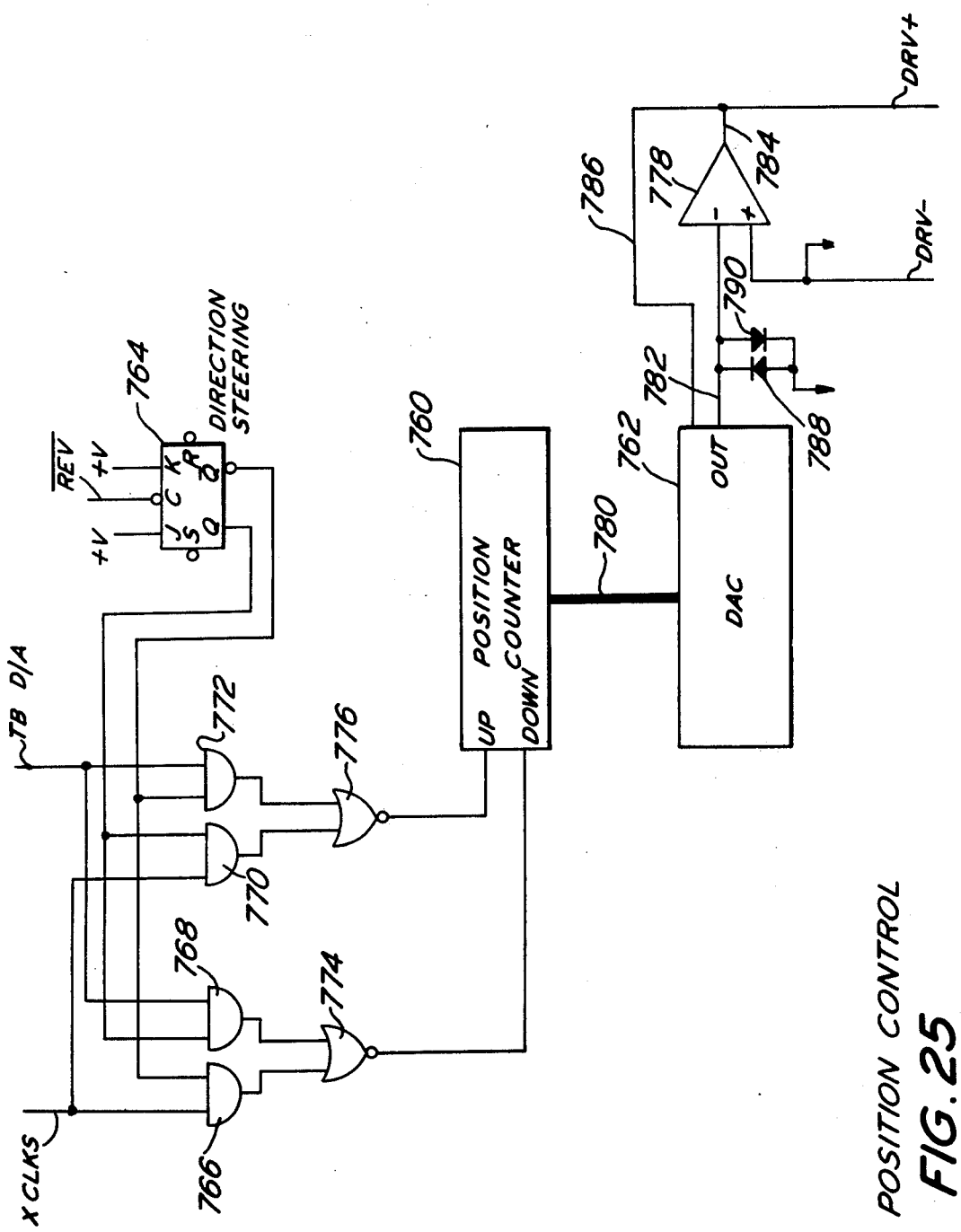
FIG. 25 is a schematic block diagram of the position control circuitry.

The position control is shown in schematic block diagram in FIG. 25. The position control includes a position counter 760, a digital to analog converter (DAC) 762, a direction steering flip flop 764, four AND gates 766, 768, 770 and 772, a pair of OR gates 774 and 776, and an output amplifier 778. The XCLKS line is connected to an input of AND gate 766 and to an input of AND gate 770. The TBD/A line is connected to an input of AND gate 768 and an input of AND gate 772.

The second inputs to AND gates 766 and 772 are connected to the $\overline{Q}$ output line of flip flop 764 and the second input of AND gates 768 and 770 are connected to the Q output line of flip flop 764. The flip flop 764 has its J and K inputs connected to +V and its clock input connected to the $\overline{REV}$ line.

The outputs of AND gates 766 and 768 are connected to the input of OR gate 774. The outputs of AND gates 770 and 772 are connected to the inputs of OR gate 776. The position counter 760 is preferably comprised of a conventional binary counter and has an up clock input and a down clock input. These inputs are respectively labeled up and down.

The OR gate 774 is connected to the down input of the position counter and the output OR gate 776 is connected to the up input of position counter 760. The output of the position counter 760 is connected in parallel to the input of the digital to analog converter 762. That is, each stage of the binary counter in position counter 760 is connected to an input to the DAC 762. DAC 762 is a conventional weighted resistor converter which converts the digital voltages on lines 780 to an analog signal on output line 782.

Output line 782 is connected to the inverting input of amplifier 778. Amplifier 778 is an operational amplifier having an output line 784 which is connected to the DRV (+) line and to a feed back line 786 which is connected to the output circuit of the digital to analog converter 762.

A pair of diodes 788 and 790 are connected between the output line 782 and ground in parallel but opposite directions. These diodes are provided to prevent a spike from damaging the output circuitry of the digital to analog converter. The noninverting input (+) of amplifier 778 is connected to ground as well as to the DRV line. The DRV+ and the DRV- lines are connected to the input amplifier 528.

In operation, the position control circuitry is utilized to control the movement of the lens assembly 566 of the fine focus assembly. The position counter 760 controls the location of the lens assembly 566 in accordance with the counts stored in the position counter 760. As the count in the position counter 760 is changed, the voltage applied by the digital to analog converter to the input amplifier controls the amount of voltage applied to the crystal assembly 564 which determines the amount of bend along its longitudinal axis which in turn determines the location of the lens assembly 566 in accordance with the amount of bend of the crystal assembly.

After a capture stored pulse is generated on line CS by the capture circuitry, the XCLKS line is pulsed sixteen times and thereby provides to the position counter 760 sixteen pulses via either OR gate 774 or 776 depending on the state of the direction steering flip flop 764. If the flip flop 764 is in the set position at the time that the capture stored pulse is generated, the OR gate provides 16 pulses to the up count input of the position counter 760 and thereby moves the lens assembly 1 micron up from the previous optimum focus.

If the direction steering flip flop 764 had been in the opposite state (reset) then the 16 pulses on the XCLKS line are provided to the down input of position counter 760 via OR gate 774 and AND gate 766. Thus, the fine focus assembly is moved 1 micron down if the direction steering flip flop is in the reset state.

After the position counter has been either stepped up or stepped down by 16 pulses, the TA period is ended and the TB period starts. During the TB period, the TBD/A line is pulsed one time for each fast scan line of a focus scan. Thus, during a focus scan, eight fast scan lines cause the generation of eight pulses on the TBD/A line which are provided to the position counter 760 to either the up input or the down input, depending on the direction steering flip flop 764 status. That is, if the flip flop 764 is in the set state, the clock pulses on the TBD/A line are provided to the down input of the position counter 760 via AND gate 768 and OR gate 774. If the flip flop 764 is in the reset state, the clock pulses are provided to the up input of the position counter 760 via AND gate 772 and OR gate 776.

It is sufficient, however, to remember that the pulses on the TBD/A line step the position counters 760 in a direction opposite to those pulses provided on the XCLKS line. Thus, if the direction steering flip flop 764 is in the set condition, then the X clocks during the TA time cause the position counter 760 to be stepped up 16 times via AND gate 770 and OR gate 776. During the TB time the clock pulses are then provided via AND gate 768 and OR gate 774 to step the position counter down eight steps during each focus scan, unless a reversal of movement of the lens assembly is required to obtain optimum focus.

After the TB cycle is completed, the lens assembly 566 is returned to the optimum focus position. Thus, the $\overline{TCD/A}$ clock pulses generated during the TC time by the decision logic cause these clock pulses to be provided to the position control via the XCLKS line which thereby causes the clock pulses to step the position counter up again to reach the optimum focus position during the TC cycle.

The direction steering flip flop 764 is changed in state each time a low pulse is provided on the $\overline{REV}$ line from the decision logic in FIG. 24. When the $\overline{REV}$ line is pulsed, it causes the change of state of flip flop 764 so that pulses on the TBD/A line cause the stepping of the position counter in the opposite direction as a result of the change in state of the direction steering flip flop. Accordingly, pluses on the XCLKS line during the TC cycle cause the position counter to step in the opposite direction from the direction of the last pulses on the TBD/A line cause stepping during the TB cycle.

FOCUS CONTROL OF MICROSCOPE FOCUS

Figure 26:
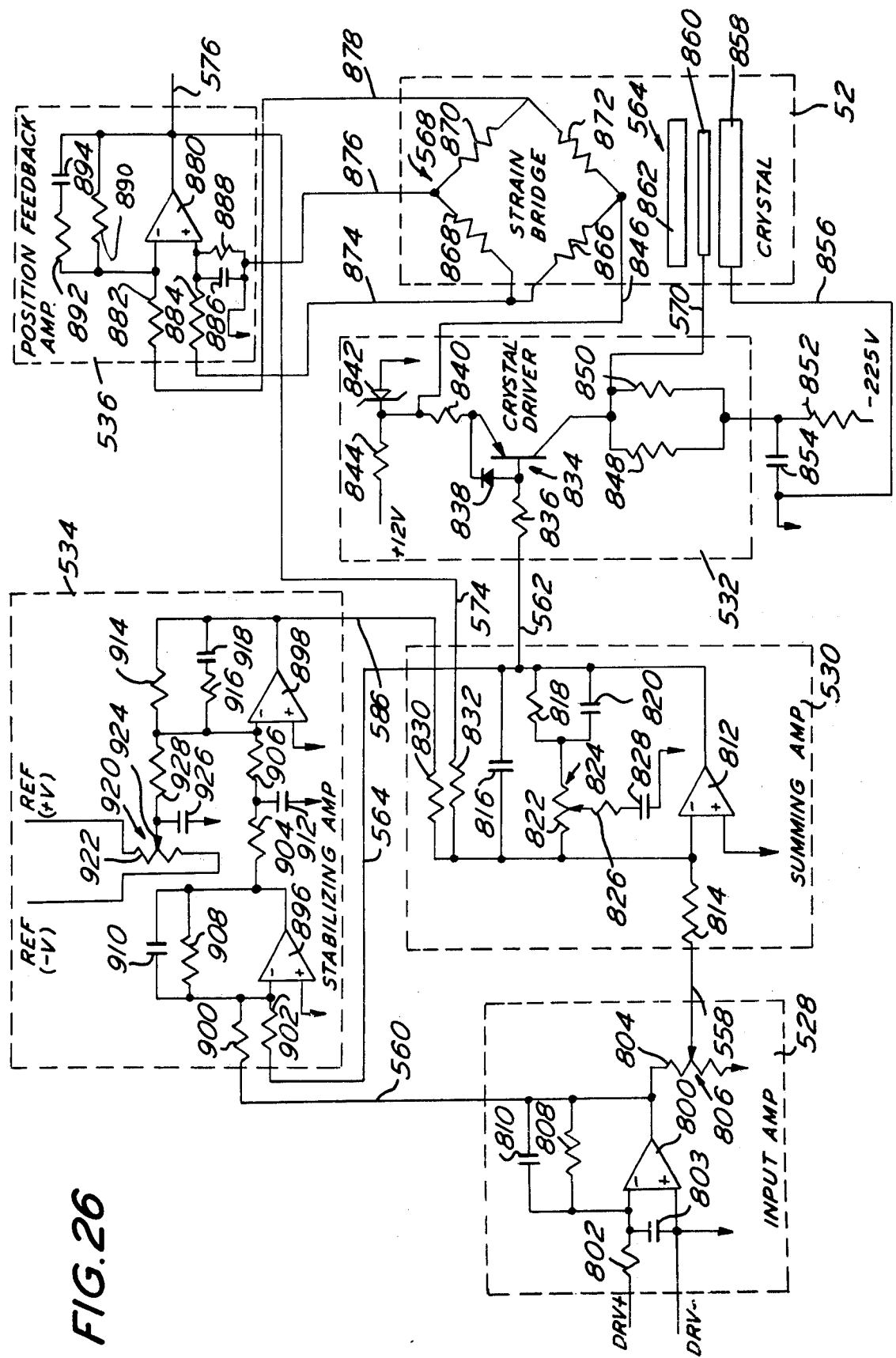
FIGS. 26 and 27 are schematics of the analog portion of the automatic focus circuitry and the interconnection with the fine focus assembly.
Figure 27:
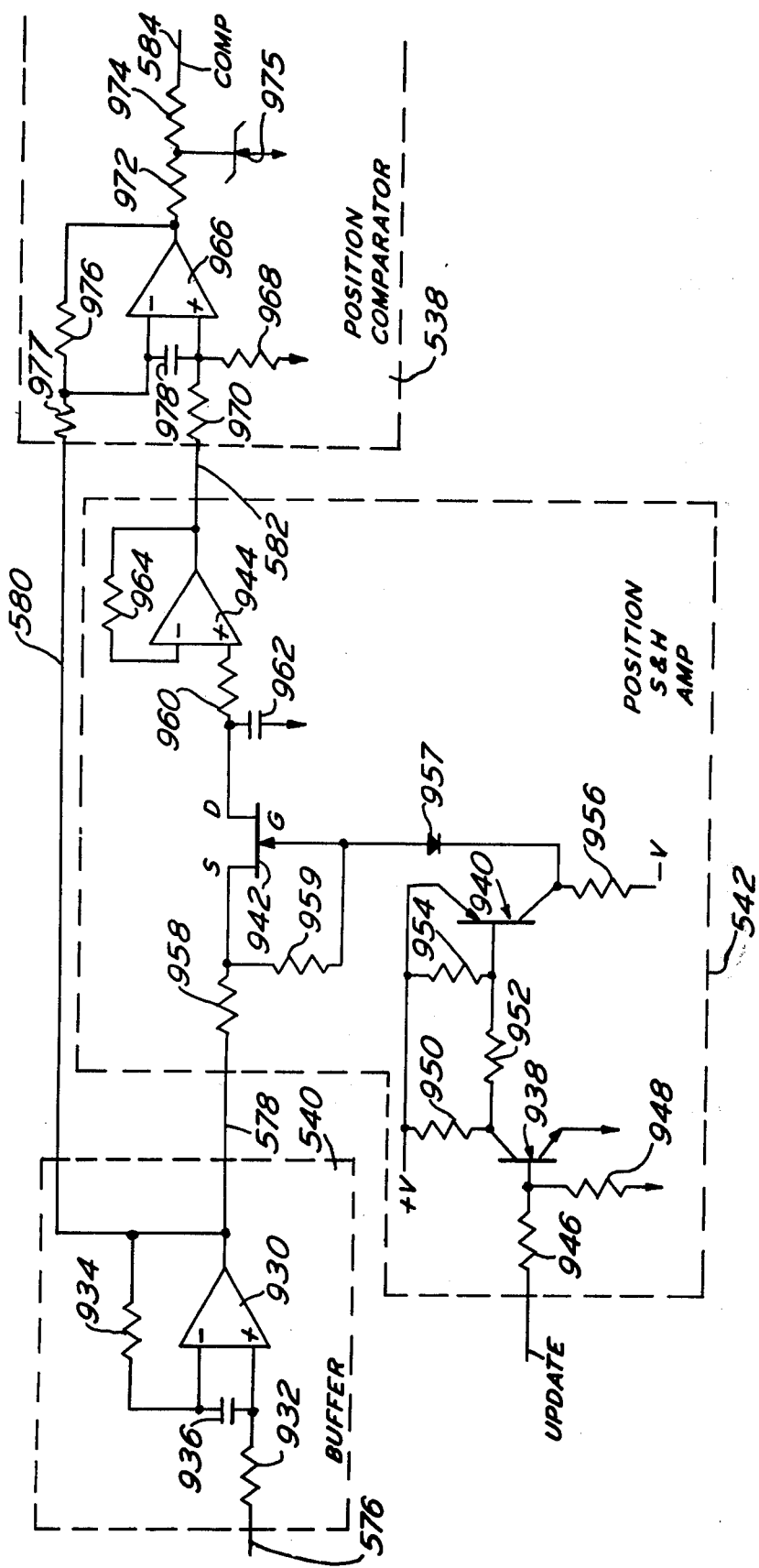

The focus control of the microscope focus is shown in FIGS. 26 and 27. The circuitry shown in FIGS. 26 and 27 is the analog portion of the automatic focus circuitry. In FIG. 26, the circuitry shown includes the input amplifier 528, the summing amplifier 530, the crystal driver 532, the stabilizing amplifier 534 and the position feedback amplifier 536. Also shown, schematically, in FIG. 26, is a portion of the fine focus assembly including the crystal assembly 564 and the strain bridge 568 which is formed of the resistive strain gauges secured to the outer surface of the crystal 564.

The input amplifier 528 includes an operational amplifier 800. The noninverting input (+) of amplifier 800 is connected to the DRV- line from the output amplifier 778 from the digital to analog converter 762. The inverting input (−) of amplifier 800 is connected to the DRV+ line from the output amplifier 788 of the digital to analog converter 762 via resistor 802. A capacitor 803 is connected between the inverting and noninverting inputs. The output of amplifier 800 is connected to a resistor 804 of potentiometer 806. The other end of resistor 804 is connected to ground. The wiper arm of potentiometer 806 is connected to output line 558 which is the input to the summing amplifier 530. The output of amplifier 800 is also connected via line 560 to the stabilizing amplifier 534. The operational amplifier 800 also includes a resister 808 and a capacator 810 which are connected in parallel between the output of amplifier 800 and the inverting input of amplifier 800.

The summing amplifier includes an operational amplifier 812 which has its noninverting input connected to ground and its inverting input connected to line 558 via a summing resistor 814. The output of operational amplifier 812 is connected to the stabilizing amplifier via line 564 and to the crystal driver via line 562. The output line of operational amplifier 812 is also connected to the noninverting input thereof via a feedback loop which includes a capacator 816 which is in parallel with a resistor 818 and a capacator 820 which are connected in parallel to each other from the output of amplifier 812 and in serial with a resistor 822 of a potentiometer 824 which is in turn connected to the inverting input of operational amplifier 812.

The wiper arm of potentiometer 824 is connected to a resistor 826 which is in turn connected to a capacitor 828 which is connected at its other side to ground. The noninverting input to the operational amplifier 812 is also connected via a resistor 830 to the output of the stabilizing amplifier via line 586. In addition, the noninverting input of operational amplifier 812 is connected via resistor 832 and output line 574 to the output of the position feedback amplifier 536.

The crystal driver 532 includes a transistor 834 which is preferably of the PNP type and which has its base connected to input line 562 via resistor 836. The base is also connected to the emitter of the transistor 834 via a diode 838 which acts to prevent breakdown of the base emitted junction of transistor 834. The emitter of transistor 834 is connected to ground via resistor 840 and zener diode 842. The emitter is connected to +12 volts via resistor 840 and resistor 844.

The emitter of transistor 834 is also connected via resistor 840 to output line 846 which is connected to the strain bridge at the fine focus assembly 52. The collector of transistor 834 is connected to a pair of parallel resistors 848 and 850 which are in turn connected to −225 volts via resistor 852 and to ground via capacitor 854. The ground at capacitor 854 is also connected via line 856 to the lower crystal layer 858 of crystal assembly 554. The collector of the transistor 834 is connected via output line 570 to the brass vane 860 of crystal assembly 564. The top crystal layer 862 of the crystal assembly 564 is not connected to a source of voltage or to ground.

The strain bridge 558 is basically connected as a Wheatstone bridge comprised of four resistor strain gauges, 866, 868, 870 and 872. The resistor 866 is connected to resistor 868 at one end and resistor 872 at its other end. Resistor 868 is connected at its other end to resistor 870, resistor 870 is connected at its other end to resistor 872 to form a Wheatstone bridge.

The point at which resistors 866 and 868 are joined is connected to line 874 which is in turn connected to the input of the position feedback amplifier 536. The junction between resistor strain gauges 868 and 870 is connected to line 876 which is connected to ground at the position feedback amplifier 536. The junction between resistive strain gauges 870 and 872 is connected via line 878 to the input of the position feedback amplifier 536.

The position feedback amplifier 536 includes an operational amplifier 880 which has its inverting input connected via resistor 882 to input line 878. The non-inverting input of operational amplifier 880 is connected via resistor 884 to input line 874. The noninverting input is also connected to ground via a capacitor 886 and a resistor 888 which are connected in parallel. The output of operational amplifier 880 is connected via a feedback loop to its inverting input via a resistor 890 which is in parallel with a serially connected resistor 892 and capacitor 894. The output of operational amplifier 880 is also connected to output line 576 which is connected to the input of the buffer amplifier 540 (FIG. 27).

The stabilizing amplifier 534 includes a first operational amplifier 896 and a second operational amplifier 898. The inverting input of amplifier 896 is connected via resistor 900 to input line 560 and to line 564 via resistor 902. The noninverting input of amplifier 896 is connected to ground. The output of amplifier 896 is connected to the noninverting input of amplifier 896 via a resistor 908 and a capacitor 910 which are connected in parallel. The junction between resistors 904 and 906 is connected to ground via a capacitor 912. The noninverting input of amplifier 898 is connected to ground.

The output of amplifier 898 is connected to output line 586 which is connected to summing resistor 830 of summing amplifier 530. The output of operational amplifier 898 is also connected to its noninverting input via resistor 914 which is connected in parallel with a serially connected resistor 916 and capacitor 918.

A reference voltage source is provided by a potentiometer 920 comprised of resistor 922 and a wiper arm 924. The wiper arm 924 is connected via capacitor 926 to ground and to the noninverting input of operational amplifier 898 via resistor 928. The resistor 922 of potentiometer 920 is connected at one end to a reference voltage of +V and at its other end to a reference voltage of −V.

The remainder of the circuitry comprising the voltage control for the microscope focus is shown in FIG. 27 wherein the buffer amplifier 540, the position S and H amplifier 542 and the position comparator 538 are shown. The buffer amplifier 540 includes an operational amplifier 930 which has its noninverting input connected via resistor 932 to input line 576 from the position feedback amplifier 536. The output of the amplifier 930 is connected to output line 578 which is connected to the position sample and hold (S and H) amplifier 542 and to the noninverting input of amplifier 930 via resistor 934. The inverting input and noninverting input are connected together by a capacitor 936, which acts to short out high frequency signals.

The position S and H amplifier 542 includes a pair of transistors 938 and 940, a field effect transistor 942 and an operational amplifier 944. The transistors 938 and 940, in combination with their associated circuitry from a digital control portion of the position S and H amplifier. Transistor 938 is preferably an NPN transistor having its base connected to the UPDATE line from the data counter, comparator and memory 522 via resistor 946. The base of transistor 938 is also connected to ground via resistor 948. The emitter of transistor 938 is connected to ground and the collector of transistor 938 is connected to +V via resistor 950 and to the base of transistor 940 via resistor 952.

Transistor 940 is preferably a PNP type of transistor which has its base connected to +V via a resistor 954 and to the collector of transistor 938 via resistor 952 and its emitter is connected to +V. The collector of transistor 940 is connected to −V via resistor 956 and to the gate input (G) of field effect transistor 942 via diode 957. The source (S) of transistor 942 is connected via resistor 958 to input line 578 from the buffer amplifier 540. The drain (D) of the field effect transistor 942 is connected to the noninverting input of operational amplifier 944 via resistor 960 and to ground via capacitor 962. The output of operational amplifier 944 is connected via output line 582 to the position comparator 538 and to its own inverting input via resistor 964.

The position comparator 538 includes an operational amplifier 966 which has its noninverting input connected to ground via resistor 968 and to input line 582 via resistor 970. The output of position comparator 966 is connected via a pair of serially connected resistors 972 and 974 to the output line 584 which is connected to the decision logic 524 and is also referred to as the COMP line. The junction of resistors 972 and 974 is connected to ground via zener diode 975.

The output of operational amplifier 966 is also connected via a feedback resistor 976 to the inverting input of the amplifier. The noninverting and inverting input of amplifier 966 is connected together via capacitor 978 which acts as a high frequency short circuit to prevent amplification of high frequency signals. The inverting input of operational amplifier 966 to also connected to line 580 via resistor 977 from the output of the buffer amplifier 540.

The function of the circuitry in FIGS. 26 and 27 is to act as a control of the focus position in the microscopic lens assembly. The input amplifier 528 functions as a buffer amplifier between the output of the digital to analog converter of the position control 526 and the summing and stabilizing amplifiers 530 and 534, respectively. Gain of the buffer amplifier is controllable by potentiometer 806.

The summing amplifier receives inputs not only from the input amplifier 528 which is basically a voltage level converter but also from stabilizing amplifier 534 via input line 586 and summing resistor 830 and from the position feedback amplifier 536 via resistor 832. The output of the summing amplifier is fed to the crystal driver 532 for controlling the voltage applied to the crystal and consequently the amount of movement imparted to the lens supported by the crystal assembly 564. The summing amplifier also includes a phase lead network which is comprised of potentiometer 824, resistor 826 and capacitor 828. The phase lead network actually provides a delay to the output of the summing amplifier which allows the time necessary for the mechanical portion of the fine focus assembly to catch up with the electronic portion of the focus control. The phase lead network thereby prevents oscillation in the Piezoelectric crystal.

The stabilizing amplifier 564 is provided to compensate for the temperature variance in the strain bridge. That is, the change of the ambient temperature in the fine focus assembly causes temperature drift in the resistances of the strain gauges used in the strain bridge 568. The stabilizing amplifier impedes temperature drift by maintaining the ratio between the voltage at the output of the input amplifier 528 and the output voltage at the summing amplifier. These output voltages from the input amplifier and summing amplifier are fed respectively on line 560 and 564 via resistors 900 and 902, to the inverting input of stabilizing amplifier 896. The output voltage of the operational amplifier 896 is fed to amplifier 898 which provides the voltage via line 586 to the input of the summing amplifier via summing resistor 830. However, it should be noted that the resistor 906 and capacitor 912 in combination act as a time delay of approximately one minute and forty seconds in order to prevent the stabilizing amplifier from changing the system in the summing amplifier during a focusing operation.

The crystal driver 532 has its transistor 834 connected as a common emitter amplifier for driving the crystal in accordance with the voltage provided on line 562 to the base of transistor 534. As the voltage from the summing amplifier is increased, the voltage applied to the collector of transistor 834 to the brass vane 860 causes a greater constriction of the lower crystal layer 858 with respect to brass vane 860 of the crystal assembly and therefore a movement of the lens assembly in an upward direction as the center of the crystal assembly moves upwardly with respect to its ends. When the voltage at the base of transistor 834 is decreased, the voltage differential between the brass vane and the crystal layer 858 decreases, thereby increasing the length of crystal layer 858 with respect to the brass vane 860 and causing the center of the crystal assembly to move downwardly with respect to its ends and thereby moving the objective lens downwardly. The bend of the crystal assembly along its longitudinal axis controls the vertical movement of the objective lens assembly. The position feedback amplifier 536 is a voltage amplifier which is responsive to the output of the strain bridge and generates on output line 576 a voltage corresponding to the amount of bend of the crystal assembly along its longitudinal axis and thus corresponds to the present position of the objective lens.

The present position voltage applied on line 576 by the position feedback amplifier is provided to the buffer amplifier 540 in FIG. 27 which acts as a buffer between the position feedback amplifier and the sample and hold amplifier 542 and position comparator 538. The buffer amplifier is a following amplifier which provides the present position voltage on line 578 to the source of field effect transistor 942 via coupling resistor 958. The present position is also provided simultaneously to the position comparator 538 via line 580.

The position S and H amplifier 542 enables the voltage on line 578 to be stored by capacator 962 when the field effect transistor is caused to be conductive between the source and drain thereof. That is, the transistor 938 and 940 and their associated circuitry, comprise a digital control for the field effect transistor. When the UPDATE line from data counter comparator and memory 522 goes high which is caused by A being larger than B when the test is made during the T2 period of the minor timing cycle, transistor 938 becomes conductive thereby causing the collector thereof to provide a low voltage to the base of transistor 940. Transistor 940 thus has its emitter-base junction forward biased thereby causing the voltage at the collector of transistor 940 to go high which in turn causes the field effect transistor 942 to become conductive and thus enables the voltage on line 578 to be stored in the capacator 962. At the end of the UPDATE pulse, the field effect transistor 942 is turned off and thereby causes the capacitor 962 to be isolated so that it stores the voltage provided to the field effect transistor 942 during the UPDATE pulse.

The UPDATE pulse is generated during the T2 portion of each minor timing cycle as long as the total in the data counter 650 (A) is greater than that in the data register 652 (B). Thus, as soon as the lens assembly passes the optimum focus point, the data counter produces a count that is less than the previously high stored total in data register 652. Therefore, the UPDATE pulse is not generated which causes the capacitor 962 to store the voltage representative of the position of the objective lens assembly at optimum focus. The voltage across capacitor 962 is provided to the noninverting input of operational amplifier 966 of the position comparator 538 by the operational amplifier 944 of the position S and H amplifier 542.

The position comparator 538 acts an an analog comparator of the voltage signal provided on line 580 (the present position voltage) and 582 (the optimum focus position voltage) to the operational amplifier 966. When the voltage on the input to line 582 exceeds the voltage on line 580, the operational amplifier provides a positive output signal on the COMP line 584. Depending on the direction of motion of the lens assembly, as the lens continues to move, the voltage on line 580 becomes increasingly larger or smaller than the voltage applied by line 582 from the operational amplifier 944 which is controlled by capacitor 962. Thus, if the voltage on line 576 to buffer 540 is constantly increasing as the objective lens moves in a first direction, then after the UPDATE pulses cease, the input voltage on line 580 continues to increase while the voltage on line 582 remains stable thereby causing the output of comparator 966 to stay at the lower level until the end of the TB time unless there is a reversal.

At the end of TB time, line 584 remains low. During the TC time, the direction of movement of the objective lens assembly is in the reverse direction which therefore causes a decreasing of the voltage on line 580 as the objective lens assembly approaches the optimum position. When the lens assembly reaches the optimum position, the voltage on line 580 equals the voltage on line 582 and then goes lower upon the next increment of movement. This causes the output of operational amplifier 966 to go high as a result of the voltage on line 580 going lower than on line 582 and thereby causes a change of voltage on output line 584. This change of voltage of the COMP line 584 acts to end the TC portion of the major timing cycle and also causes a termination of movement of the objective lens assembly at the optimum focus position.

Similarly, if the direction of movement of the objective lens assembly was in the direction during the TB time that the voltage on line 576 was decreasing after each increment, after the UPDATE pulses stop, the voltage on line 580 decreases below the voltage on line 582 to the operational amplifier 966 and thereby causes the COMP line 584 to remain high until the end of TB time. Thus, when the objective lens assembly is reversed at the beginning of TC time, the voltage on line 580 increases. When the voltage on line 580 exceeds the voltage provided on line 582 it causes the operational amplifier to change its output voltage to a low level at the point of optimum focus.

Both conditions which cause a change on the COMP output line 584 from a low level to a high level or from a high level to a low level is recognized by the decision logic as the optimum focus point and causes termination of movement of the objective lens assembly. This is accomplished by terminating the pulses to the digital to analog converter of position control 552 which controls the posiition of the objective lens assembly through the voltage applied to the crystal assembly.

Figure 28:
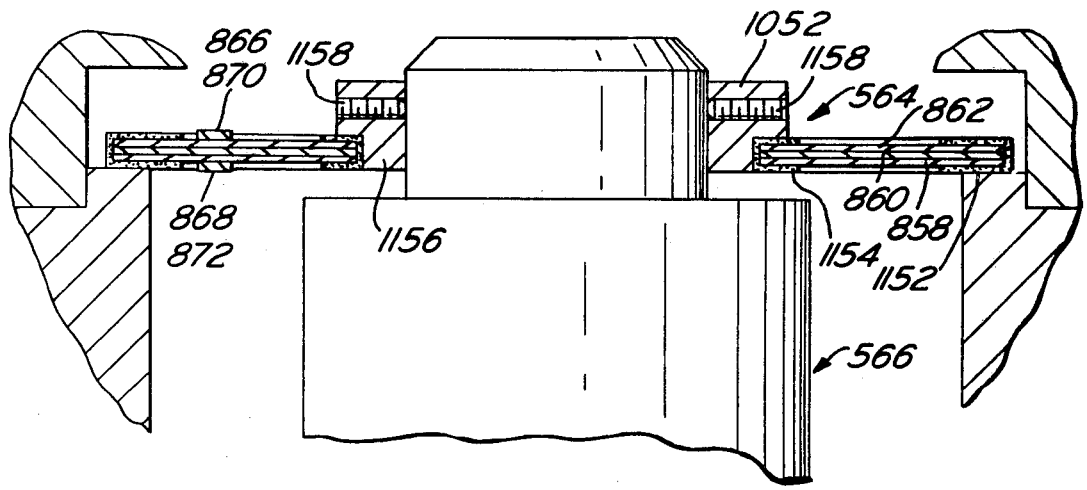
FIG. 28 is an enlarged vertical sectional view taken through the Piezoelectric crystal assembly with the objective lens assembly shown secured therein in full for purposes of clarity.

The fine focus assembly which is the subject matter of aforementioned U.S. Pat. No. 3,915,560, the details of which are incorporated by reference herein, is shown in FIGS. 28 to 31. In FIG. 28, the crystal assembly 564 is shown in vertical section and it includes a pair of piezoelectric crystal layers 858 and 862 which sandwich a brass vane 860. An epoxy coating is provided about the periphery of the crystal assembly 564 to seal the edges at 1152. Similarly, an epoxy coating is provided at 1154 about the periphery of opening 1144 (See FIG. 29) to seal the remaining edges of the crystal layers and brass vane.

A mounting ring 1052 is suitably secured in opening 1144 of the crystal assembly 564 to enable the mounting of a lens assembly 566 to the crystal assembly 564. The lens assembly 566 acts as the objective lens of the microscopic lens assembly 22. The mounting ring 1052 includes a pair of radially extending threaded openings in which are provided threaded fasteners 1158 which are provided to secure the ring to the lens assembly 566. As seen in FIG. 28, the crystal mounting ring is adhesively secured, preferably by an epoxy resin, to the crystal assembly within opening 1144. The mounting ring 1052 includes a depending boss 1156 which exends into the opening 1144 within the crystal assembly 1138.

As is also seen in FIG. 28, the strain gauges 866 and 870 are adhesively secured to the top surface of the crystal layer 862 and the strain gauges 868 and 872 are adhesively secured to the bottom surface of the crystal layer 858. The crystal assembly 564 is seen prior to the securement of the mounting ring 1052 in FIGS. 29 and 30. Cable 1160 from the automatic focus 31 includes a plurality of power wires 1164, 1166 and 1168 which provide the voltages to the layers of the crystal assembly which enable the crystal assembly to be bent in accordance with the amount of voltage applied thereto. The crystal assembly, as it is bent, acts as a translation means for moving the objective lens.

Figure 29:
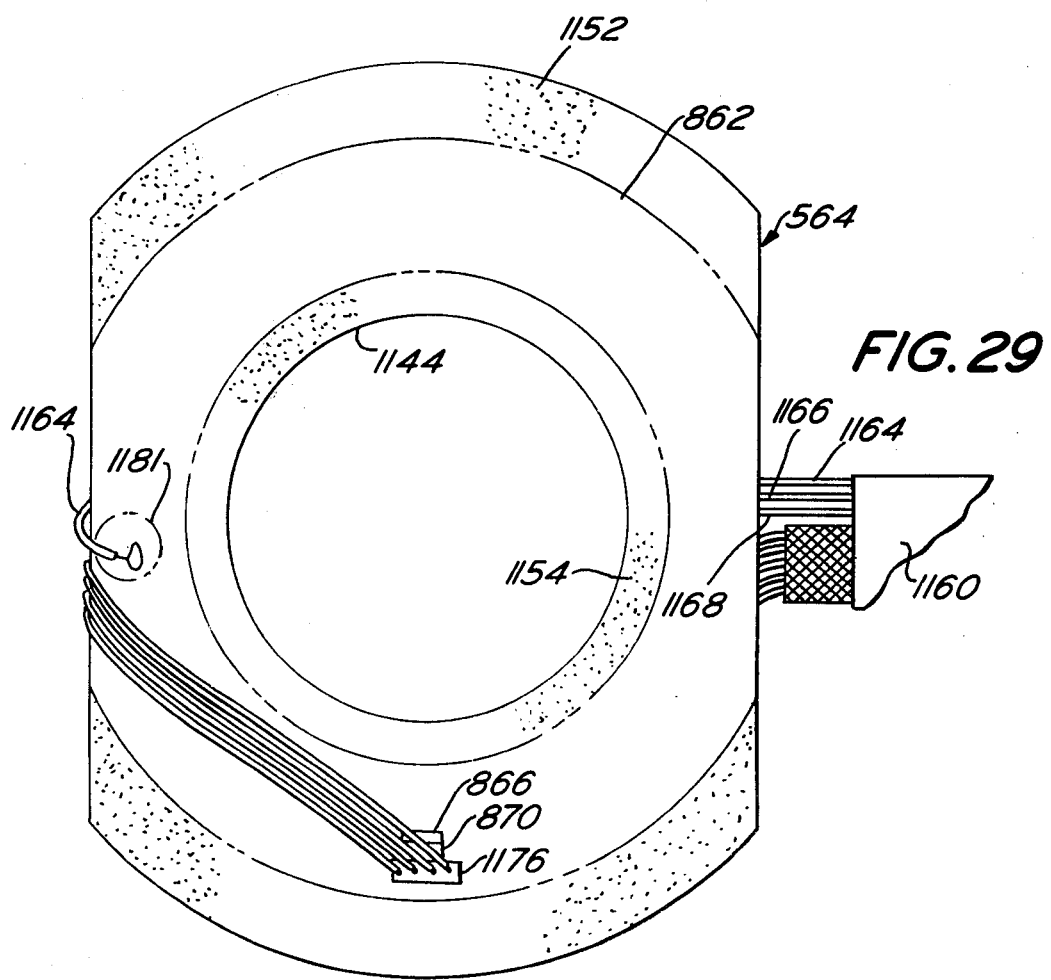
FIG. 29 is an enlarged top plan view of the crystal shown with its associated wiring attached thereto with the crystal mounting ring removed for purposes of clarity.
Figure 30:
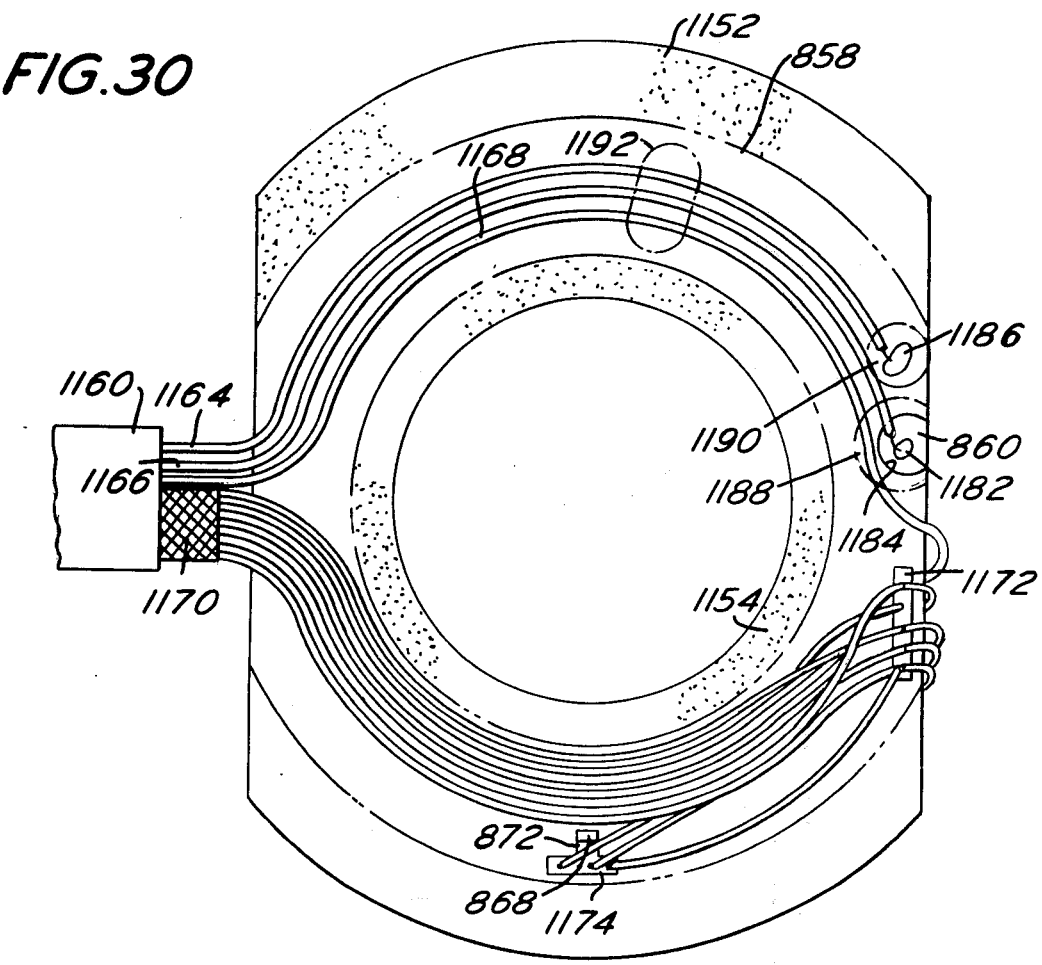
FIG. 30 is a bottom plan view of the crystal shown in FIG. 29.

Also provided within cable 1160 are a plurality of shielded leads 1170 which are connected to terminal strips 1172 and 1174, as seen in FIG. 30 and terminal strip 1176 as seen in FIG. 29. Adjacent terminal strip 1174 strain gauges 868 and 872 are secured to the crystal layer 858. The strain gauges are electrically connected to the various terminals of the terminal strip 1174. Adjacent terminal strip 1176, as seen in FIG. 29, a pair of strain gauges 866 and 870 are secured to crystal layer 862 which are electrically connected to the various terminal strips 1176. The terminal strips, as well as the strain gauges 866, 868, 870 and 872, are suitably adhered to the outer surface of the crystal layer 858 and 862.

Lead 1164 of the power leads is connected to the outer surface of crystal surface 862 by soldering the lead to the outer surface thereof. A thin layer of epoxy 1181 is applied over the solder and the exposed portion of lead 1164 so that the junction between the lead of 1164 and the outer surface of the crystal is suitably insulated. On the bottom side of the crystal, lead 1166 is soldered to the brass vane 860 at 1182. The brass vane 860 is exposed by an opening 1184 which is provided in the crystal layer 858.

Lead 1164 is soldered to the outer surface of the crystal layer 858 at 1186. Both the soldering connections at 1182 and 1186 are covered by a thin layer of epoxy 1188 and 1190, respectively, which act to insulate the soldered connections. In addition, the leads 1164, 1166 and 1168 are physically secured, though not electrically connected, to the crystal layer 858 by a thin layer of epoxy 1192.

The leads 1164, 1166 and 1168 carry the necessary signals discussed hereinabove to the crystal assembly for the purposes of controlling the voltage to the crystal assembly to control the motion of the crystal assembly as well as provide a voltage to the strain bridge formed of the strain gauges and providing leads for carrying the electrical signals from the strain bridge to the position feedback amplifier.

It should be remembered that as the voltage across crystal layer 858 and the brass vane changes, the crystal layer 858 contracts or expands with respect to the brass vane 860 and thereby causes a greater or smaller bending depending on the voltage differential between the brass vane and the crystal layer 858. In the preferred embodiment, voltage is not applied to the top layer 862 of the crystal. However, it should be understood that voltage can be applied in a required amount. The larger the magnitude of voltage to brass vane 860, the more the crystal layer 858 contracts and causes the central portion of the crystal assembly to move upwardly with respect to the ends of the crystal assembly.

Figure 31:
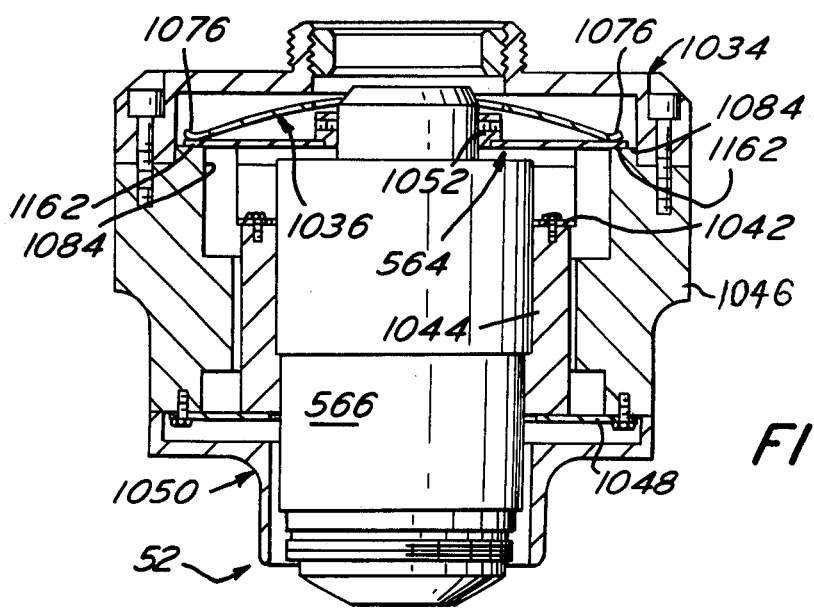
FIG. 31 is an elevational view with portions shown in vertical section of the fine focus assembly.

Referring to FIG. 31, which is a vertical sectional view of a preferred fine focus assembly 52, it can be seen that the fine focus assembly includes, in addition to the crystal assembly 564 and the objective lens assembly 566, a housing which comprises an upper portion 1034 and a lower portion 1046, an upper mounting leaf spring 1042, a lens holder 1044, a lower mounting leaf spring 1048, a lens shield 1050 and the crystal mounting ring 1052 which is secured to the crystal assembly 564.

As seen in FIG. 31, the housing is generally cylindrical and includes a somewhat cylindrical bore. The bore includes a pair of flanges 1084 on which the ends 1162 of the crystal assembly 564 rest. A leaf spring 1036 is provided which is secured to the upper portion 1034 of the housing and which has ends 1076 which are bent back up in a small U-shape which rest against the ends 1162 of the crystal assembly 564 to maintain the same against the top surface of the flanges 1084. The lens assembly 566 is suspended into a lens holder 1044. The lens holder 1044 is supported by a pair of mounting springs 1042 and 1048. The mounting springs are both leaf springs which are secured by fasteners at their ends to the lower portion 1046 of the housing and are secured at their centers to the lens holder 1044. Each of the leaf springs 1042 and 1048 include openings through which the objective lens assembly 566 passes. The securement of the center of spring 1048 to the bottom surface of lens holder 1044 is hidden in FIG. 31. Similarly, the securement of the ends of springs 1042 to the lower portion 1046 is also hidden by the lens assembly.

The springs 1042 and 1048 are provided to enable movement of the objective lens assembly along the optical path of the objective lens without frictional engagement since there is no sliding of the objective lens assembly 566 relative to another part of the fine focus assembly 52. That is, the objective lens assembly 566 moves with the holder 1044. In view of the fact that the weight of the lens assembly and holder 1044 provide a preloading force, the center of springs 1042 and 1048 is biased downwardly prior to the application of voltage to the crystal assembly. As long as the objective lens assembly moves with the holder 1044, there is no frictional engagement between the objective lens assembly and the lens holder 1044 because they move together as the springs 1042 and 1048 are deflected at their center.

This is explained in greater detail in the aforementioned U.S. Pat. No. 3,915,560 for a fine focus assembly.

The fine focus assembly 52 enables extremely accurate movement of the objective lens assembly 566 and the feedback of a signal which accurately identifies the location of the objective lens. When the magnitude of voltage applied to brass vane 860 of the crystal assembly 564 increases, the crystal layer 858 contracts with respect to the brass vane 860 and thereby causes the center of the crystal assembly to move up with respect to the ends 1062 thereof which support the crystal assembly on flanges 1084. The increased voltage magnitude across the brass vane thus lifts the lens assembly 566.

Similarly, when a smaller voltage is applied to brass vane 860, the crystal layer 858 increases in length with respect to the brass vane and the center of the crystal assembly is therefore lowered and thus lowers the lens assembly. As the crystal assembly is bent to lower or raise the lens assembly, the strain gauges are either stretched or compressed depending on the location of their position. When the gauges are compressed such as the gauges on the bottom surface when the center of the crystal assembly moves up or at the top when the center of the crystal assembly moves down, the resistance of the strain gauges goes down. When stretched by movement in the opposite direction, the resistances of the gauges goes down. The Wheatstone bridge connection of the strain gauges engages the signal provided from the strain bridge to correspond to the amount of bend of the crystal assembly and thus the position of the objective lens assembly.

OPERATION OF THE FINE FOCUS ASSEMBLY

The automatic focus circuitry is utilized after each white cell has been captured. Capture means that the white cell has been placed within the field of view of the microscopic lens system and is ready for classification.

In the instant system, the capturing of the white cell is indicated by the generation of the captured stored signal (CS). Thus, referring to the focus timing control in FIG. 22, the CS line goes low upon the generation of the captured stored signal. When the captured stored signal goes low, it causes the focus flip flop 610 to be set and thereby generate the high signal on the FOCUS line. It also causes the $\overline{Q}$ output of flip flop 610 to go low thereby providing a low signal on the $\overline{FOCUS}$ line.

Referring to FIG. 13, it can be seen that the high signal on the FOCUS line causes flip flop 206 to be primed for being set when the end of fast scan pulse is provided to the clock input of the flip flop 206. Since the $\overline{FOCUS}$ line goes low, it provides a disabling signal to the slow scan control in FIG. 19 to prevent the setting of rescan backup flip flop 206 to cause a seven micron backup until the end of the focus cycle.

Upon receipt of the EOFS pulse, rescan backup flip flop 206 is set which causes rescan counter 204 to be reset to zero and also enables the slow scan counter 202 to be stepped down once for each of the first four fast scan lines after capture has been made. This is enabled by the four line backup flip flop which is set by the CS pulse and thereby enables the gate 224 to pass four EOFS pulses to the C down input of slow scan counter 202 until the rescan counter reaches the count of four whereupon the four line backup flip flop 214 is reset and thereby prevents the slow scan counter from being changed in count during the remainder of the focus cycle as well as during the remainder of the rescan mode.

The occurence of the first EOFS pulse after the capture is made also causes the enabling of AND gate 618 in FIG. 22 which causes the one micron backup flip flop 612 to be set. The one micron backup flip flop controls the clock pulses to the position control counter 760 which enables the lens assembly to be moved one micron from the previous optimum focus. That is, the one micron backup flip flop, when it is set by the enabling of AND gate 618, causes the AND gate 622 to be enabled to pass the FS4 pulses to OR gate 626 and on to the position counter 760. The FS4 pulses go positive every 32 fast scan counts. Thus, after 16 pulses are provided on the FS4 line, and have passed via the OR gate 626 in FIG. 22 to the XCLKS line, and to FIG. 25, the position counter 760 is either stepped up or down depending on the last movement of the lens assembly to move the same to its previous optimum focus. Thus, assuming that the lens assembly was moving down to reach its previous optimum focus, the direction steering flip flop 64 was in the reset state. The direction steering flip flop is thus in the reset state when the 16 pulses passed by OR gate 626 are generated at the initiation of the next focus cycle. Thus, the sixteen pulses are provided to the down input of the position counter 760 and thereby step down the position counter by the count of 16 which causes a 1 micron total movement of the lens assembly down from the previous optimum focus.

As soon as the sixteen pulses have been fed to the position counter during the TA time portion of the focus cycle, the FS9 line from the output of the fast scan counter receives a pulse and on the leading edge causes the one micron backup flip flop to be reset since the K input is connected to +V.

When the one micron backup flip flop is reset, the $\overline{Q}$ output goes high thereby causing OR gate 624 to be disabled and the lowering of the signal at the output thereof causes the major timing register 600 to shift the one in the shift register to the TB state thereby causing the TB portion of the focus cycle.

When the rescan counter 204 in FIG. 13 receives the fourth EOFS pulse and switches from a count of three to four, the four line backup flip flop 214 is reset and thereby prevents any further pulses from stepping the slow scan counter 202. At the same time, the count of 4 in the rescan counter causes the RS2 line to go high thereby causing the data enable flip flop in FIG. 22 to be set via AND gate 638 which is also primed for enabling by the high signal on the output line TB of the major timing register 600. When the data enable flip flop 614 is set, the DE line goes high and thereby causes an enabling signal to And gate 704 in the data counter comparator and memory shown in FIG. 23. AND gate 704 is thus enabled during the TB time during the fourth through twelfth counts in the rescan counter during the period of time that the information provided from the color processors and quantizers correspond to the area of the field in which the white cell is captured. For each fast scan line, from rescan count four through eleven, the AND gate 704 is enabled to provide a pulse on the TB D/A line which is conencted to the position counter 760 via AND gate 768 and 772. Since it is assumed that the direction steering flip flop 764 was reset, AND gate 772 is enabled to transfer the TB D/A pulse via OR gate 776 to the up input of the position counter 760 and thereby causes the position counter 760 to be stepped up eight times during the count of four through eleven in the rescan counter.

Thus, each fast scan line during the period that the rescan counter goes from four to eleven causes the lens assembly to move up 1/16 micron during each fast scan line or a total of ½ micron during the focus cycle interval.

The window pulse which is high during the capture window causes the J input of the data count flip flop 656 in FIG. 23 to be primed to be set upon the next P1 pulse which occurs during each count of the fast scan counter. The data count flip flop 656, when it is set, enables AND gate 686 and AND gate 682 to pass weighted quantized data to the OR gate 678 which is counted by the data counter 650. Thus, during the first focus scan which takes place during the first cycle of the rescan counter from 4 to 12, the weighted quantized data count is provided to the counter 650. Since the data register 652 is cleared prior to taking a count during the first focus scan, the data comparator 654 determines that A is larger than B by providing a high signal on line 64.

As soon as the rescan counter reaches the count of twelve, the AND gate 630 in FIG. 22 is enabled and thereby causes the first minor timing cycle which follows each data counting interval during a focus scan. The enabling of AND gate 628 primes the J input of flip flop 602 (T1) to be set on the next pulse from the FS6 line of the fast scan counter. As soon as flip flop 602 is set, the Q output provides, via inverter 636, a signal on line FRR to AND gate 226 of the slow scan timing in FIG. 13 which causes the rescan backup flip flop 206 and the rescan sweep flip flop 208 to be reset and thereby causes the rescan counter to be reset.

Also, during the T1 interval of the minor timing, the comparison is made whether A is larger than B by data comparator 654 and, since during the first half micron interval of movement A is larger than B, a one is placed into the first stage of decision register 710 in FIG. 24.

When the next FS6 pulse is provided in FIG. 22, the one in flip flop 602 is shifted to the flip flop 604 which causes the generation of a high signal on the T2 line to enable the T2 portion of the minor timing cycle. During the T2 interval, if the count in data counter 650 is higher than the count in data register 652, And gate 668 is enabled. If A is larger than B, this causes the data register to have the data count in counter 650 stored in data register 652.

Also, at the shifting of the one from flip flop 602 to flip flop 604, as the T1 line goes low, the data enable flip flop 614 in FIG. 22 is reset and thereby prevents any further data counting or clock pulses to the position counter 760 until it is set again by the next enabling AND gate 638 when the rescan counter 204 reaches the next count of four.

When the data enable flip flop 614 is set again, it enables the next focus scan and data counting. The TB D/A clock pulses are again resumed during the second focus scan. Again, when the rescan counter 204 reaches the count of 12, the second focus scan is terminated and the second minor timing cycle is begun wherein the count in data counter 650 is compared with the count in data register 652 by the data comparator 654. If A is larger than B, it again indicates that the optimum focus is being approached and thereby causes the data register 652 to be updated to the new highest data count which is stored for the next focus scan. A second one is placed into the decision register 710 during the T2 time. During T3 time, AND gate 726 in FIG. 24 is sampled to determine whether the direction of movement of the lens assembly should be reversed and during T4 time the AND gate 734 in FIG. 24 is sampled to determine whether the TB portion of the major timing cycle has been completed.

Assuming that on the third focus scan the data count in data counter 650 is less than that in data register 652, the data comparator provides on line 664 a low signal which indicates that B is larger than A which causes the AND gate 668 to be disabled when the T2 pulse is generated thereby preventing the data counter 650 from having its contents stored in the data register 652. Thus, the highest count reached in the data counter 650 is the count that is stored in the data register 652 at optimum focus.

Since the optimum focus point is passed when the count in data counter 650 is smaller than the data register 652, the next focus scans also produce lower totals in the data counter 650 than is present in data register 652 and thereby cause the two ones placed in data register 710 to be followed by a group of zeros as the decision register 710 is shifted during the T2 time of each of the minor timing cycles after each of the weighted quantized data counts are taken.

Thus, when the first one of the two ones reaches stage D6 of decision register 710 in FIG. 24, OR gate 714 is enabled, the four zeros in stages D1 to D4 enable AND gate 712 and the AND gate 716 also remains enabled and thereby causes AND gate 722 to be enabled. When AND gate 722 is enabled it primes AND gate 726 to be enabled during the T3 interval of the minor timing cycle. When AND gate 726 is enabled the output goes low and thereby causes the direction steering flip flop in FIG. 25 to cause a reversal of the direction steering flip flop 764. When this happens, it causes the clock pulses on the TB D/A line to be directed to the down input of counter 760 and thereby causes during the succeeding focus scans the stepping down of the position counter 760 and the consequent moving down of the lens assembly 566.

It should be noted that the flip flop 728 (FIG. 24) was set as soon as the white cell was captured. Flip flop 728 is provided to prevent more than one reversal during the TB period when the data counts are taken. Thus, the Q output line of flip flop 728 is high to enable the AND gate 726 when it is determined that only two ones are placed into the decision register thereafter. The flip flop 728 is changed in state to the reset state when AND gate 726 is enabled via inverter 730 and OR gate 718, the output of which is connected to the K input and enables the flip flop 728 to be reset during the T4 interval of the minor timing cycle.

The flip flop 728 can also be reset without a reversal when at least three ones are initially placed in the decision register 710, the first of the three ones reach the D7 stage of the decision register and thereby cause the priming of the K input for reversal of the state of the flip flop 728 during the T4 time.

Upon reversal, the focus scans continue with the movement of the lens assembly reversed. In the instant example the reversal causes the lens assembly to move downwardly. Each weighted quantization data count is taken during an eight step or one half micron move of the lens assembly. That is, the focus scan is made with the focus at a different level for each of the eight fast scan lines of the focus scan. Prior to reversal of movement, the total in data counter 650 is loaded to data register 652 by the high signal on the REV line.

Since the optimum focus point was passed by at least two microns (which were the zeros required to fill the stages D1 through D4 of the decision register 710) at least three ones are caused by the data comparator 654 before the optimum focus has been passed again and the count in data counter 650 is lower than the highest stored count in data register 652.

When the first one reaches the D6 stage of the decision register 710 (FIG. 24), it should be noted that the AND gate 712 remains disabled in view of the fact that there is at least a one in the D4 stage of the decision register 710 which prevents the AND gate 722 from being enabled. Also, since the flip flop 728 has been reset by the first reversal, AND gate 726 cannot be enabled and thereby prevents a reversal signal from being generated.

The focus scans continue until the first one is placed in the D8 stage of the decision register 710 which causes flip flop 732 to be set. Thus, on the first T4 pulse after the focus scan which causes the first one to be placed in stage D8 of decision register 710, AND gate 734 is enabled and thereby generates a positive signal on the TB-TC line which indicates the end of the TB time of the major timing cycle. As seen in FIG. 22, the TB-TC line provides a pulse which enables the OR gate 624 and on the trailing edge causes the major timing register 600 to shift from TB to TC. The TB-TC line also causes the EXCLUSIVE OR gate 738 in FIG. 24 to load the COMP signal on the J input of flip flop 742. At the trailing edge of the T4 interval, T4 goes low and the TB-TC line again goes high thereby causing a negative going pulse to the clock input of flip flop 742 which causes the flip flop 742 to assume the same state as the signal on the COMP line. That is, if the COMP line has a positive signal thereon, the flip flop 742 is set. If the signal on the COMP line is low, the flip flop 742 is reset. In either event, the two lines to EXCLUSIVE OR gate 740 are at the same level thereby disabling the EXCLUSIVE OR gate 740.

During the data counting period, each time a data comparison was made and A was larger than B, AND gate 668 (FIG. 23) was enabled during the T2 time. The output of AND gate 668 is also connected by the UPDATE line to the position S and H amplifier 542 in FIG. 27. Each pulse on the UPDATE line causes the digital control transistors 938 and 940 to be turned on and thereby cause field effect transistor 942 to be conductive to store the voltage provided at the output of buffer amplifier 540 across capacitor 962. Thus, the position of the crystal at optimum focus, as sensed by the strain bridge 568, is stored by capacitor 962 until the lens assembly is returned to optimum focus. Thus, assuming that the present position voltage on line 580 from the buffer amplifier is higher than that provided on line 582 by amplifier 944 at the end of the TB time, the output of the position comparator on the COMP line is low thereby causing at the end of the TB time the resetting of flip flop 742 by EXCLUSIVE OR gate 738 in FIG. 24.

Both inputs to the EXCLUSIVE OR gate 740 are therefore low at the initiation of TC time. When the TC line goes high, the signal is fed to AND gate 750 and AND gate 754 in the decision logic of FIG. 24. AND gate 752 is thus enabled by the enabling of AND gate 754 and the $\overline{Q}$ output of flip flop 748 to pass pulses on the FS6 line to the $\overline{TCD/A}$ line which enables pulses to be passed via OR gate 626 in FIG. 22 to the XCLKS line which are provided to AND gate 766 and 770 in the position control of FIG. 25. Since the direction steering flip flop 764 was set by the reversal, the $\overline{TCD/A}$ pulses are thus provided to the position counter 760 via AND gate 770 and OR gate 776 during the TC time. Each of these pulses causes the movement of the lens assembly 1/16 micron in the upward direction and the lens assembly continues to move up until such time as the position of the crystal assembly 564 causes the signal on line 580 in FIG. 27 to go lower than the signal on line 582 which is representative of the position of optimum focus. As soon as the signal on line 580 goes below the signal on line 582, the amplifier 966 is turned on and thereby causes a high signal on the COMP line which causes the COMP line to go high and thereby causes the EXCLUSIVE OR gate 740 in FIG. 24 to enable AND gate 746 upon the next pulse on the FS4 line from the fast scan counter. As soon as the FS4 pulse is terminated, the flip flop 748 is set as a result of the positive voltage of the J input of flip flop 748 and thereby causes AND gate 750 to be primed to be enabled at the end of the present fast scan line by the EOFS pulse which enables AND gate 750. The enabling of AND gate 750 causes a low signal on the $\overline{ENDTC}$ line. The $\overline{ENDTC}$ line resets the focus flip flop 610, the 1 micron backup flip flop 612 and the data enable flip flop 614 in FIG. 22. In addition, the $\overline{ENDTC}$ line also causes the OR gate 624 to provide a pulse to shift the major timing register 600 to end the focus cycle by shifting out the one in the TC stage.

It should be noted that at the same time that the EOFS signal enables AND gate 750 to end the TC time, the EOFS signal also causes the rescan backup flip flop 206 in FIG. 13 to be set to initiate the classification cycle of the rescan mode. When the focus flip flop 610 is reset by the $\overline{ENDTC}$ pulse, the $\overline{FOCUS}$ line connected to the $\overline{Q}$ output of focus flip flop 610 goes high which enables the AND gate 472 in FIG. 19 which causes a low signal at the summing resistor 484 and thus causes the beam of the flying spot scanner to move back 7 microns during the classification cycle so that the edge of the window 126 (FIG. 4) is moved to a point to the left of the point at which capture is made.

It can therefore be seen that a new and improved automatic focusing system has been provided. The automatic focusing system utilizes the scanning system which is used for pattern recognition to enable a generation of quantization data which enables the circuitry to determine the optimum focus position of the lens assembly in the microscopic lens system.

The unique focusing system further facilitates the accurate classification of patterns scanned by the pattern recognition system in view of the fact that the transitions between light and dark areas are maximized.

Moreover, the automatic focusing system utilizes small focusing scans over the area which is known to contain sufficient quantization data to enable the determination of the optimum focus.

The automatic focusing system also enables focusing accuracies greater than that which can be accomplished with the human eye. The short focus scan also enables the system to change the focus to obtain the optimum focus, even where a reversal is required, in less than 150 milliseconds. The focusing time therefore does not take a major portion of the time needed in making an automatic blood cell differential count. Thus, in a 100 white cell differential count, the focusing required on each of the 100 cells would take a total time of less than 15 seconds, even if a reversal were required during every focus.

The system disclosed herein is capable of obtaining optimum focus as long as the change in optimum focus from one white cell to another does not prevent capture of the second cell. It is unusual, however, when adjacent white cells are each at an optimum focus which are more than 2 microns apart.

Another unique technique utilized in this system is that the control of the microscopic lens focus is not accomplished by movement of the platform stage or the slide, but rather, by moving the objective lens assembly with respect to the eyepiece in order to position the image of the scanned object on the image plane of the photomultiplier tubes in the color separation unit.

The fine focus assembly which is the subject of the aforementioned U.S. Pat. No. 3,915,560 also enables the system to utilize a servo system type of approach by enabling feedback of the position by means of a strain bridge secured to the crystal assembly which controls the position of the objective lens assembly to enable positioning accuracies within 1/16 of a micron. As seen above, the optimum focus point in the preferred embodiment is controlled within an accuracy of a half micron.

Without further elaboration, the foregoing will so fully illustrate our invention that others may, by applying current or future knowledge, readily adapt the same for use under various conditions of service.

We claim:

1. A pattern recognition system including scanning means for scanning a field including a plurality of patterns to be recognized and classified and an optical instrument for enabling scanning of said field, means responsive to said scanning means for generating a signal in accordance with the color density of the field scanned, means responsive to said signal for causing said scanning means to rescan an area of said field when one of said plurality of patterns is detected and means responsive to said signal during said rescan for moving said optical instrument to its optimum focus position before each one of said plurality of patterns is classified.

2. The system of claim 1 wherein said scanning system is a flying spot scanner and said optical instrument directs the light therefrom at said field.

3. The system of claim 2 wherein said optical instrument is a microscope and said field scanned is a whole blood smear on a slide.

4. The system of claim 3 wherein said light is passed through said blood smear and said means responsive to said scanning means is disposed on the side of said slide opposite said instrument for receiving said light directed through said slide and being responsive to said light to generate a signal in accordance with the intensity thereof.

5. In a pattern recognition system, means for scanning a field, an optical instrument to facilitate scanning of said field, said field having a plurality of classes of patterns therein, said means for scanning traversing said field in a first direction in a fast scan and in a second direction in a slow scan, means responsive to said scanning means for generating signals corresponding to the colors of said field at the positions scanned, detection means responsive to said signal for detecting when said means for scanning has reached the location of a pattern from one of said classes of patterns, said scanning means traversing said second direction at a first speed until said means responsive to said signals detects said pattern from one of said classes of patterns, and control means responsive to said detection for backing up said scanning means in said second direction and causing said scanning means to traverse said pattern at a second speed slower than said first speed and focus means responsive to said scanning means during said scan at said slower speed to move the position of focus of said optical instrument to its optimum focus position.

6. The system of claim 5 wherein the length of said scan in said fast direction is greater than the length of any of the patterns in said field, said system further including window control means responsive to said detection means to enable said focus means to receive only a portion of said signal when said pattern is detected, said portion of said signal corresponding to the area of said field immediately surrounding and including said pattern.

7. The system of claim 5 wherein said control means is responsive to said focus means to backup said scanning means in said second direction a plurality of times until said optimum focus position of said optical instrument is achieved.

8. A white blood cell classification system for detecting and classifying white blood cells in a peripheral blood smear, said system including means for scanning fields in the blood smear, a microscope for directing said scanning means at said fields, means responsive to said scanning means for generating a signal corresponding to the color of said field at the position scanned, color processing means responsive to said signal for providing a signal representative of the relative darkness of said area scanned, and detection means responsive to said signal, said detection means including a mask which is normally enabled by the nucleus of all the white cells, but which is not enabled by a platelet or foreign material in the blood smear and focus means responsive to said detection means for moving the position of focus of said microscope to optimum focus position after each white cell is detected.

9. The system of claim 8 wherein said scanning means is controlled by said detection means and said focus means, said scanning means being caused to rescan the area of said smear where a pattern is located which causes said mask to be enabled.

10. The system of claim 9 wherein said focus means causes said scanning means to scan the area of said smear a plurality of times, said focus position of said microscope being moved during each of said plurality of scans.

11. The system of claim 10 wherein each of said white cells are classified after the scanning means is optimally focused thereon.

* * * * *